US012763166B2

(12) United States Patent
Kagalwalla et al.

(10) Patent No.: US 12,763,166 B2
(45) Date of Patent: Oct. 13, 2026

(54) SPECIALIST SIGNAL PROFILERS FOR BASE CALLING

(71) Applicant: Illumina, Inc., San Diego, CA (US)

(72) Inventors: Abde Ali Hunaid Kagalwalla, San Diego, CA (US); Eric Jon Ojard, San Francisco, CA (US); Rami Mehio, San Diego, CA (US); Gavin Derek Parnaby, Laguna Niguel, CA (US); Nitin Udpa, San Diego, CA (US); John S. Vieceli, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 1158 days.

(21) Appl. No.: 17/839,353

(22) Filed: Jun. 13, 2022

(65) Prior Publication Data

US 2023/0018469 A1 Jan. 19, 2023

Related U.S. Application Data

(60) Provisional application No. 63/223,408, filed on Jul. 19, 2021.

(51) Int. Cl.
*G16B 30/00* (2019.01)
*G16B 20/40* (2019.01)
*G16B 40/10* (2019.01)

(52) U.S. Cl.
CPC ............. *G16B 30/00* (2019.02); *G16B 20/40* (2019.02); *G16B 40/10* (2019.02)

(58) Field of Classification Search
None
See application file for complete search history.

(56) References Cited

U.S. PATENT DOCUMENTS

| | | | |
|---|---|---|---|
| 5,528,050 | A | 6/1996 | Miller et al. |
| 5,641,658 | A | 6/1997 | Adams et al. |
| 5,719,391 | A | 2/1998 | Kain |
| 6,090,592 | A | 7/2000 | Adams et al. |
| 6,266,459 | B1 | 7/2001 | Walt et al. |
| 6,355,431 | B1 | 3/2002 | Chee et al. |
| 6,598,013 | B1 | 7/2003 | Domnisoru et al. |
| 6,770,441 | B2 | 8/2004 | Dickinson et al. |
| 6,778,692 | B1 | 8/2004 | Yazici |
| 6,859,570 | B2 | 2/2005 | Walt et al. |
| 6,865,301 | B1 | 3/2005 | Harris |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,595,882 | B1 | 9/2009 | Chen et al. |
| 7,622,294 | B2 | 11/2009 | Walt et al. |
| 8,158,926 | B2 | 4/2012 | Feng et al. |
| 8,241,573 | B2 | 8/2012 | Banerjee et al. |
| 8,563,477 | B2 | 10/2013 | Smith et al. |
| 8,612,161 | B2 | 12/2013 | Gordon et al. |
| 8,778,848 | B2 | 7/2014 | Lin et al. |
| 8,778,849 | B2 | 7/2014 | Bowen et al. |
| 8,895,249 | B2 | 11/2014 | Shen et al. |
| 8,965,076 | B2 | 2/2015 | Garcia et al. |
| 9,012,022 | B2 | 4/2015 | George et al. |
| 9,079,148 | B2 | 7/2015 | Rigatti et al. |
| 9,483,610 | B2 | 11/2016 | Mcmillen et al. |
| 9,512,422 | B2 | 12/2016 | Barnard et al. |
| 10,068,053 | B2 | 9/2018 | Kermani et al. |
| 10,378,053 | B2 | 8/2019 | Staker et al. |
| 10,691,775 | B2 | 6/2020 | Van Rooyen et al. |
| 11,188,778 | B1 | 11/2021 | Ojard et al. |
| 11,347,965 | B2 | 5/2022 | Dutta et al. |
| 11,455,487 | B1 | 9/2022 | Kagalwalla et al. |
| 11,972,583 | B2 | 4/2024 | Shen et al. |
| 11,989,265 | B2 | 5/2024 | Kagalwalla et al. |
| 12,211,589 | B2 | 1/2025 | Li et al. |
| 2002/0034337 | A1 | 3/2002 | Shekter |

(Continued)

FOREIGN PATENT DOCUMENTS

| | | | |
|---|---|---|---|
| CN | 102676657 | B | 1/2015 |
| CN | 112203648 | A | 1/2021 |

(Continued)

OTHER PUBLICATIONS

Wang et al "An adaptive decorrelation method removes Illumina DNA base-calling errors caused by crosstalk between adjacent clusters" Scientific Reports vol. 7, Article No. 41348 (2017) (Year: 2017).
Wikipedia, Least Squares, 13 pages, retrieved on Mar. 7, 2022, retrieved from the internet [URL: https://en.wikipedia.org/w/index.php?title=Least_squares&oldid=951737821 ].
Wikipedia, Ordinary Least Squares, 16 pages, retrieved on Mar. 7, 2022, retrieved from the internet [URL: https://en. Wikipedia .org/w/index. php?title=Ordinary _least_squares&oldid=951770366 ].
Dressman et al., Transforming single DNA molecules into fluorescent magnetic particles for detection and enumeration of genetic variations, Proceedings of the National Academy of Science, vol. 100, No. 15, pp. 8817-8822, dated Jul. 22, 2003, 6 pages.
Rakocevic et al., Fast and Accurate Genomic Analyses using Genome Graphs, biorxiv URL [https://www.biorxiv.org/content/biorxiv/early/2018/03/20/194530.full.pdf], dated Mar. 20, 2018, 104 pages.

(Continued)

*Primary Examiner* — Kaitlyn L Minchella
*Assistant Examiner* — Jonathan Edward Hayes
(74) *Attorney, Agent, or Firm* — Keller Preece PLLC

(57) ABSTRACT

The disclosed system comprises a memory and a runtime logic. The memory stores a plurality of specialist signal profilers. Each specialist signal profiler in the plurality of specialist signal profilers is trained to maximize signal-to-noise ratio of sequenced signals in a particular signal profile detected for analytes in a particular analyte class and characterized in a particular training data set. The runtime logic, having access to the memory, is configured to execute a base calling operation by applying respective specialist signal profilers in the plurality of specialist signal profilers to sequenced signals in respective signal profiles detected for analytes in respective analyte classes during the base calling operation.

31 Claims, 37 Drawing Sheets
(16 of 37 Drawing Sheet(s) Filed in Color)

(56) References Cited

U.S. PATENT DOCUMENTS

| | | | |
|---|---|---|---|
| 2002/0055100 | A1 | 5/2002 | Kawashima et al. |
| 2002/0150909 | A1 | 10/2002 | Stuelpnagel et al. |
| 2003/0087289 | A1 | 5/2003 | Zuzan et al. |
| 2004/0002090 | A1 | 1/2004 | Mayer et al. |
| 2004/0096853 | A1 | 5/2004 | Mayer |
| 2005/0064460 | A1 | 3/2005 | Holliger et al. |
| 2005/0130173 | A1 | 6/2005 | Leamon et al. |
| 2006/0020203 | A1 | 1/2006 | Tamura |
| 2007/0128624 | A1 | 6/2007 | Gormley et al. |
| 2007/0177799 | A1 | 8/2007 | Tyurina |
| 2007/0194249 | A1 | 8/2007 | Gavrilov et al. |
| 2008/0009420 | A1 | 1/2008 | Schroth et al. |
| 2008/0108082 | A1 | 5/2008 | Rank et al. |
| 2008/0234136 | A1 | 9/2008 | Drmanac et al. |
| 2008/0242560 | A1 | 10/2008 | Gunderson et al. |
| 2009/0024331 | A1 | 1/2009 | Tomaney et al. |
| 2009/0035779 | A1 | 2/2009 | Kurnik et al. |
| 2009/0088327 | A1 | 4/2009 | Rigatti et al. |
| 2010/0034444 | A1 | 2/2010 | Emhoff et al. |
| 2010/0160172 | A1 | 6/2010 | Erlich et al. |
| 2011/0059865 | A1 | 3/2011 | Smith et al. |
| 2011/0256631 | A1 | 10/2011 | Tomaney et al. |
| 2012/0015825 | A1 | 1/2012 | Zhong et al. |
| 2012/0020537 | A1 | 1/2012 | Garcia et al. |
| 2012/0270305 | A1 | 10/2012 | Reed et al. |
| 2012/0316086 | A1 | 12/2012 | Lin et al. |
| 2013/0023422 | A1 | 1/2013 | Feng et al. |
| 2013/0079232 | A1 | 3/2013 | Kain et al. |
| 2013/0109577 | A1 | 5/2013 | Korlach et al. |
| 2013/0116153 | A1 | 5/2013 | Bowen et al. |
| 2013/0137091 | A1 | 5/2013 | Gordon et al. |
| 2013/0184796 | A1 | 7/2013 | Marzano et al. |
| 2013/0260372 | A1 | 10/2013 | Buermann et al. |
| 2014/0153801 | A1 | 6/2014 | Sárközy et al. |
| 2014/0221216 | A1 | 8/2014 | Cope et al. |
| 2014/0228223 | A1 | 8/2014 | Gnirke et al. |
| 2014/0243224 | A1 | 8/2014 | Barnard et al. |
| 2015/0057167 | A1 | 2/2015 | Kaiser et al. |
| 2015/0065353 | A1 | 3/2015 | Turner et al. |
| 2015/0079596 | A1 | 3/2015 | Eltoukhy et al. |
| 2015/0125053 | A1 | 5/2015 | Vieceli et al. |
| 2015/0169824 | A1 | 6/2015 | Kermani et al. |
| 2017/0152554 | A1 | 6/2017 | Drmanac et al. |
| 2017/0318240 | A1 | 11/2017 | Yu |
| 2018/0101951 | A1 | 4/2018 | Xu et al. |
| 2018/0195953 | A1 | 7/2018 | Langlois et al. |
| 2018/0260940 | A1 | 9/2018 | Langlois et al. |
| 2018/0274023 | A1 | 9/2018 | Belitz et al. |
| 2019/0259137 | A1 | 8/2019 | Zerfass et al. |
| 2019/0385699 | A1 | 12/2019 | Garcia et al. |
| 2020/0097701 | A1 | 3/2020 | Chukka et al. |
| 2020/0224243 | A1 | 7/2020 | Desai et al. |
| 2020/0234099 | A1 | 7/2020 | Wang et al. |
| 2020/0234124 | A1 | 7/2020 | Park |
| 2020/0302223 | A1 | 9/2020 | Dutta et al. |
| 2020/0302224 | A1 | 9/2020 | Jaganathan et al. |
| 2020/0302225 | A1 | 9/2020 | Dutta et al. |
| 2020/0350037 | A1 | 11/2020 | Mishra |
| 2020/0364496 | A1 | 11/2020 | Kostem |
| 2020/0364565 | A1 | 11/2020 | Kostem |
| 2021/0011896 | A1 | 1/2021 | Huang et al. |
| 2021/0118110 | A1 | 4/2021 | Langlois et al. |
| 2021/0158512 | A1 | 5/2021 | Sun et al. |
| 2021/0217171 | A1 | 7/2021 | Li et al. |
| 2021/0264232 | A1 | 8/2021 | Kim |
| 2021/0350163 | A1 | 11/2021 | Ojard et al. |

FOREIGN PATENT DOCUMENTS

| | | | |
|---|---|---|---|
| EP | 3306566 | A1 | 4/2018 |
| JP | 2020-056677 | A | 2/2021 |
| RU | 2291197 | C2 | 1/2007 |
| RU | 2565550 | C2 | 10/2015 |
| WO | WO 91/06678 | A1 | 5/1991 |
| WO | WO 00/63437 | A1 | 1/2002 |
| WO | WO 2004/018493 | A1 | 3/2004 |
| WO | WO 2004/018497 | A3 | 6/2004 |
| WO | WO 2005/024010 | A1 | 3/2005 |
| WO | WO 2005/065814 | A1 | 7/2005 |
| WO | WO 2005/010145 | A3 | 8/2005 |
| WO | WO 2006/120433 | A1 | 11/2006 |
| WO | WO 2007/010251 | A2 | 1/2007 |
| WO | WO 2007/010252 | A1 | 1/2007 |
| WO | WO 2008/041002 | A2 | 4/2008 |
| WO | WO 2007/123744 | A3 | 11/2008 |
| WO | WO 2012/058096 | A1 | 5/2012 |
| WO | WO 2015/002813 | A1 | 8/2015 |
| WO | WO 2016/066586 | A1 | 6/2016 |
| WO | 2017/098013 | A1 | 6/2017 |
| WO | 2018/068600 | A1 | 4/2019 |
| WO | 2020/037571 | A1 | 2/2020 |
| WO | 2020/037574 | A1 | 2/2020 |
| WO | WO 2020/236945 | A1 | 11/2020 |

OTHER PUBLICATIONS

PCT/US2021/030965—Second Written Opinion, dated Mar. 16, 2022, 7 pages.

PCT/US2021/030965—Response to Second Written Opinion, dated Mar. 16, 2022, filed Apr. 25, 2022, 7 pages.

Wolowski, Vincent Roman "High-quality, high-throughput measurement of protein-DNA binding using HiTS-FLIP", Munich, Mar. 2, 2016, 251 pages.

Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet [URL: https://media.nature.com/original/natureassets/nature/journal/v4567/n218/extref/nature07517-s1.pdf].

U.S. Appl. No. 17/511,483—Response to Office Action dated Feb. 3, 2022, filed Apr. 25, 2022, 17 pages.

Weissleder Ralph et al: "Automated molecular-image cytometry and analysis in modern oncology", Nature Reviews Materials, Nature Publishing Group UK, London, vol. 5, No. 6, Mar. 5, 2020 (Mar. 5, 2020), pp. 409-422, XP037159302, DOI: 10.1038/S41578-020-0180-6 [retrieved on Mar. 5, 2020].

U.S. Appl. No. 17/308,035, filed Jul. 27, 2021, Notice of Allowance.

U.S. Appl. No. 17/522,864, filed Nov. 2, 2022, Notice of Allowance.

U.S. Appl. No. 17/511,483, filed Feb. 3, 2022, Office Action.

U.S. Appl. No. 17/511,483, filed May 16, 2022, Notice of Allowance.

Whiteford et al., Swift: Primary data analysis for the Illumina Solexa sequencing platform, Bioinformatics, vol. 25, No. 17, 2009, pp. 2194-2199, 7 pages.

Abbaszadegan M., "An Encoder-Decoder Based Basecaller for Nanopore DNA Sequencing", York Space Institutional Repository, Feb. 1, 2019, 112 Pages.

Boza , et al., "DeepNano: Deep recurrent neural networks for base calling in MinION nanopore reads", PLOS one, Mar. 30, 2016, 12 pages.

Cacho , et al., "A Comparison of Base-calling Algorithms for Illumina Sequencing Technology", Briefings in Bioinformatics, Oct. 5, 2015, 786-795.

Genome Analysis Wiki , "Base Caller Summaries", Mar. 12, 2010, 4 pages.

Huang N., et al., "SACall: a neural network basecaller for Oxford Nanopore sequencing data based on self-attention mechanism Publisher: IEEE Cite This PDF", IEEE/ACM Transactions on Computational Biology and Bioinformatics,, Nov. 19, 2020, 10 pages.

Kao , et al., "BayesCall: A model-based basecalling algorithm for high-throughput short-read sequencing", Genome Research, 2009, 1884-1895.

Kircher , et al., "Improved base calling for the Illumina Genome Analyzer using machine learning strategies", Genome Biology, Aug. 14, 2009, 9 pages.

Konishi H., et al., "Halcyon: an accurate basecaller exploiting an encoder-decoder model with monotonic attention", Bioinformatics, Nov. 9, 2020, 1211-1217.

(56) References Cited

OTHER PUBLICATIONS

Miculinic N., et al., "MinCall—MinION end2end convolutional deep learning basecaller", Cornell University, Apr. 22, 2019, 8 pages.
Peresini P., et al., "Nanopore base calling on the edge", Bioinformatics, Dec. 15, 2021, 4661-4667.
Ratkovic M., "Deep learning model for base calling of MinION Nanopore Reads", Diss. Ph. D. thesis, Fakultet Elektrotehnike i Racunarstva, Sveuilite u Zagrebu,, Mar. 3, 2017, 48 pages.
Raza S., "Artificial intelligence for genomic medicine.", Cambridge: PHG Foundation, University of Cambridge, May 1, 2020, 63 pages.
Thornley D., et al., "Machine Learning in Basecalling—Decoding Trace Peak Behaviour", Oct. 1, 2006, 9 pages.
Wang S., et al., "WaveNano: a signal-level nanopore base-caller via simultaneous prediction of nucleotide labels and move labels through bi-directional WaveNets", Quant Biol (6), Dec. 1, 2018, 10 pages.
Wick R., et al., "Performance of neural network basecalling tools for Oxford Nanopore sequencing", Genome Biology, Jun. 24, 2019, 10 pages.
Xuan L., et al., "An End-to-end Oxford Nanopore Basecaller Using Convolution-augmented Transformer", 2020 IEEE International Conference on Bioinformatics and Biomedicine (BIBM), Dec. 16, 2020, 6 pages.
Zeng J., et al., "Causalcall: Nanopore Basecalling Using a Temporal Convolutional Network",Jan. 20, 2020, 11 pages.
J. Shen, X. Tang, X. Dong and L. Shao, "Visual Object Tracking by Hierarchical Attention Siamese Network", in IEEE Transactions on Cybernetics, vol. 50, No. 7, pp. 3068-3080, Jul. 2020, DOI: 10.1109/TCYB.2019.2936503.

Top Surface 402
Lane Group 502a
Lane Group 502b
Lane Group 502c
Lane 508a
Lane 508b
Lane 508l
Section Swatch 506a
Swatch 506b
Tiles 512a, b, t
Tile 512t Sub-Tile 518a
Sub-Tile 518b
Sub-Tile 518c
Sub-Tile 518d
. . .
Sub-Tile 518s

| Cluster Classes 602 | Specialist Signal Profilers 604 |
|---|---|
| Top Surface 402 | Specialist Signal Profiler 604a |
| Bottom Surface 412 | Specialist Signal Profiler 604b |

Fig. 7A

| Cluster Classes 702 | Specialist Signal Profilers 704 |
|---|---|
| Lane Group 502a | Specialist Signal Profiler 704a |
| Lane Group 502b | Specialist Signal Profiler 704b |
| Lane Group 502c | Specialist Signal Profiler 704c |

Fig. 7B

| Cluster Classes 712 | Specialist Signal Profilers 714 |
|---|---|
| Lane 508a | Specialist Signal Profiler 714a |
| Lane 508b | Specialist Signal Profiler 714b |
| . . . | . . . |
| Lane 508l | Specialist Signal Profiler 714l |

Fig. 7C

| Cluster Classes 722 | Specialist Signal Profilers 724 |
|---|---|
| Swatch 506a | Specialist Signal Profiler 724a |
| Swatch 506b | Specialist Signal Profiler 724b |

Fig. 7D

| Cluster Classes 732 | Specialist Signal Profilers 734 |
|---|---|
| Tile 512a | Specialist Signal Profiler 734a |
| Tile 512b | Specialist Signal Profiler 734b |
| . . . | . . . |
| Tile 512t | Specialist Signal Profiler 734t |

Fig. 7E

| Cluster Classes 742 | Specialist Signal Profilers 744 |
|---|---|
| Sub-Tile 518a | Specialist Signal Profiler 744a |
| Sub-Tile 518b | Specialist Signal Profiler 744b |
| Sub-Tile 518c | Specialist Signal Profiler 744c |
| Sub-Tile 518d | Specialist Signal Profiler 744d |
| . . . | . . . |
| Sub-Tile 518s | Specialist Signal Profiler 744s |

| Signal Distributions 1902 | Cluster Sets 1904 | Specialist Signal Profilers 1908 |
|---|---|---|
| Signal Distribution 1 | Cluster Set 1 | Specialist Signal Profiler 1 |
| Signal Distribution 2 | Cluster Set 2 | Specialist Signal Profiler 2 |
| Signal Distribution 3 | Cluster Set 3 | Specialist Signal Profiler 3 |
| Signal Distribution N | Cluster Set N | Specialist Signal Profiler N |

Fig. 19

| Method | Error Rate | % Pass Filter | % Aligned | %>= Q30 |
|---|---|---|---|---|
| Adaptive+Spatial | 0.331603 | 79.300003 | 1.3 | 89.884804 |
| Current RTA | 0.352007 | 79.300003 | 1.3 | 89.338310 |

SPECIALIST SIGNAL PROFILERS FOR BASE CALLING

PRIORITY APPLICATION

This application claims the benefit of U.S. Provisional Patent Application No. 63/223,408, titled, "SPECIALIST SIGNAL PROFILERS FOR BASE CALLING," filed Jul. 19, 2021. The provisional application is hereby incorporated by reference for all purposes.

FIELD OF THE TECHNOLOGY DISCLOSED

The technology disclosed relates to apparatus and corresponding methods for the automated analysis of an image or recognition of a pattern. Included herein are systems that transform an image for the purpose of (a) enhancing its visual quality prior to recognition, (b) locating and registering the image relative to a sensor or stored prototype, or reducing the amount of image data by discarding irrelevant data, and (c) measuring significant characteristics of the image. In particular, the technology disclosed relates to removing spatial crosstalk from sensor pixels using equalization-based image processing techniques.

INCORPORATIONS

The following are incorporated by reference for all purposes as if fully set forth herein:

U.S. Nonprovisional patent application Ser. No. 17/308,035, titled "EQUALIZATION-BASED IMAGE PROCESSING AND SPATIAL CROSSTALK ATTENUATOR," filed May 4, 2021;

U.S. Provisional Patent Application No. 63/106,256, titled "SYSTEMS AND METHODS FOR PER-CLUSTER INTENSITY CORRECTION AND BASE CALLING," filed on Oct. 27, 2020;

U.S. Nonprovisional patent application Ser. No. 15/909,437, titled "OPTICAL DISTORTION CORRECTION FOR IMAGED SAMPLES," filed on Mar. 1, 2018;

U.S. Nonprovisional patent application Ser. No. 14/530,299, titled "IMAGE ANALYSIS USEFUL FOR PATTERNED OBJECTS," filed on Oct. 31, 2014;

U.S. Nonprovisional patent application Ser. No. 15/153,953, titled "METHODS AND SYSTEMS FOR ANALYZING IMAGE DATA," filed on Dec. 3, 2014;

U.S. Nonprovisional patent application Ser. No. 15/863,241, titled "PHASING CORRECTION," filed on Jan. 5, 2018;

U.S. Nonprovisional patent application Ser. No. 14/020,570, titled "CENTROID MARKERS FOR IMAGE ANALYSIS OF HIGH DENSITY CLUSTERS IN COMPLEX POLYNUCLEOTIDE SEQUENCING," filed on Sep. 6, 2013;

U.S. Nonprovisional patent application Ser. No. 12/565,341, titled "METHOD AND SYSTEM FOR DETERMINING THE ACCURACY OF DNA BASE IDENTIFICATIONS," filed on Sep. 23, 2009;

U.S. Nonprovisional patent application Ser. No. 12/295,337, titled "SYSTEMS AND DEVICES FOR SEQUENCE BY SYNTHESIS ANALYSIS," filed on Mar. 30, 2007;

U.S. Nonprovisional patent application Ser. No. 12/020,739, titled "IMAGE DATA EFFICIENT GENETIC SEQUENCING METHOD AND SYSTEM," filed on Jan. 28, 2008;

U.S. Nonprovisional patent application Ser. No. 13/833,619, titled "BIOSENSORS FOR BIOLOGICAL OR CHEMICAL ANALYSIS AND SYSTEMS AND METHODS FOR SAME," filed on Mar. 15, 2013;

U.S. Nonprovisional patent application Ser. No. 15/175,489, titled "BIOSENSORS FOR BIOLOGICAL OR CHEMICAL ANALYSIS AND METHODS OF MANUFACTURING THE SAME," filed on Jun. 7, 2016;

U.S. Nonprovisional patent application Ser. No. 13/882,088, titled "MICRODEVICES AND BIOSENSOR CARTRIDGES FOR BIOLOGICAL OR CHEMICAL ANALYSIS AND SYSTEMS AND METHODS FOR THE SAME," filed on Apr. 26, 2013;

U.S. Nonprovisional patent application Ser. No. 13/624,200, titled "METHODS AND COMPOSITIONS FOR NUCLEIC ACID SEQUENCING," filed on Sep. 21, 2012;

U.S. Nonprovisional patent application Ser. No. 13/006,206, titled "DATA PROCESSING SYSTEM AND METHODS," filed on Jan. 13, 2011;

U.S. Nonprovisional patent application Ser. No. 15/936,365, titled "DETECTION APPARATUS HAVING A MICROFLUOROMETER, A FLUIDIC SYSTEM, AND A FLOW CELL LATCH CLAMP MODULE," filed on Mar. 26, 2018;

U.S. Nonprovisional patent application Ser. No. 16/567,224, titled "FLOW CELLS AND METHODS RELATED TO SAME," filed on Sep. 11, 2019;

U.S. Nonprovisional patent application Ser. No. 16/439,635, titled "DEVICE FOR LUMINESCENT IMAGING," filed on Jun. 12, 2019;

U.S. Nonprovisional patent application Ser. No. 15/594,413, titled "INTEGRATED OPTOELECTRONIC READ HEAD AND FLUIDIC CARTRIDGE USEFUL FOR NUCLEIC ACID SEQUENCING," filed on May 12, 2017;

U.S. Nonprovisional patent application Ser. No. 16/351,193, titled "ILLUMINATION FOR FLUORESCENCE IMAGING USING OBJECTIVE LENS," filed on Mar. 12, 2019;

U.S. Nonprovisional patent application Ser. No. 12/638,770, titled "DYNAMIC AUTOFOCUS METHOD AND SYSTEM FOR ASSAY IMAGER," filed on Dec. 15, 2009;

U.S. Nonprovisional patent application Ser. No. 13/783,043, titled "KINETIC EXCLUSION AMPLIFICATION OF NUCLEIC ACID LIBRARIES," filed on Mar. 1, 2013; and U.S. Nonprovisional patent application Ser. No. 16/826,168, titled "ARTIFICIAL INTELLIGENCE-BASED SEQUENCING," filed 21 Mar. 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Base calling accuracy is crucial for high-throughput sequencing and downstream analysis such as read mapping and genome assembly. This disclosure relates to optimizing image data to accurately base call clusters during a sequencing run. One challenge with the optimization of image data is variation in intensity profiles (or intensity distributions) of clusters in a cluster population being base called. This is particularly detrimental for multi-cycle imaging of substrates (e.g., flow cells) having a large number (e.g., thousands, millions, billions, etc.) of clusters, as it makes the scale of variation unmanageable, thereby causing a drop in data throughput and an increase in error rate.

Intensity profiles of millions of clusters on a flow cell can vary between respective clusters or between subpopulations of clusters. There are many potential reasons for this variation. It may result from differences in cluster brightness, caused by fragment length distribution in the cluster population or unwanted light emissions from adjacent clusters (spatial crosstalk). It may result from phase error, which occurs when a molecule in a cluster does not incorporate a nucleotide in some sequencing cycle and lags behind other molecules, or when a molecule incorporates more than one nucleotide in a single sequencing cycle. It may result from fading, i.e., an exponential decay in signal intensity of clusters as a function of sequencing cycle number due to excessive washing and laser exposure as the sequencing run progresses. It may result from underdeveloped cluster colonies, i.e., small cluster sizes that produce empty or partially filled wells on a patterned flow cell. It may result from overlapping cluster colonies caused by unexclusive amplification. It may result from under-illumination or uneven-illumination, for example, due to clusters being located on edges of a flow cell. It may result from impurities (e.g., bubbles) on a flow cell that obfuscate emitted signal. It may result from polyclonal clusters, i.e., when multiple clusters are deposited in the same well. It may result from different types of distortion in the image induced by the geometry of the optical lens. Such distortions may include, for example, magnification distortion, skew distortion, translation distortion, and nonlinear distortions such as barrel distortion and pincushion distortion.

This variation can be corrected in a coarse way by training an intensity corrector for the entire cluster population. Different than this would be to train respective intensity correctors for respective subpopulations of clusters, where the subpopulations are segmented in a way that minimizes sequencing errors and maximizes base calling accuracy within the bounds of available compute. This disclosure relates to the latter more granular approach. More details follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 7A shows one implementation of training respective lane group-specific specialist signal profilers for respective cluster classes.

FIG. 7B shows one implementation of training respective lane-specific specialist signal profilers for respective cluster classes.

FIG. 7C shows one implementation of training respective swath-specific specialist signal profilers for respective cluster classes.

FIG. 7D shows one implementation of training respective tile-specific specialist signal profilers for respective cluster classes.

FIG. 7E shows one implementation of training respective sub-tile-specific specialist signal profilers for respective cluster classes.

FIG. 19 shows one implementation of training respective/separate/different/independent specialist signal profilers for respective signal distributions observed in sequenced data.

DETAILED DESCRIPTION

Figure 1:
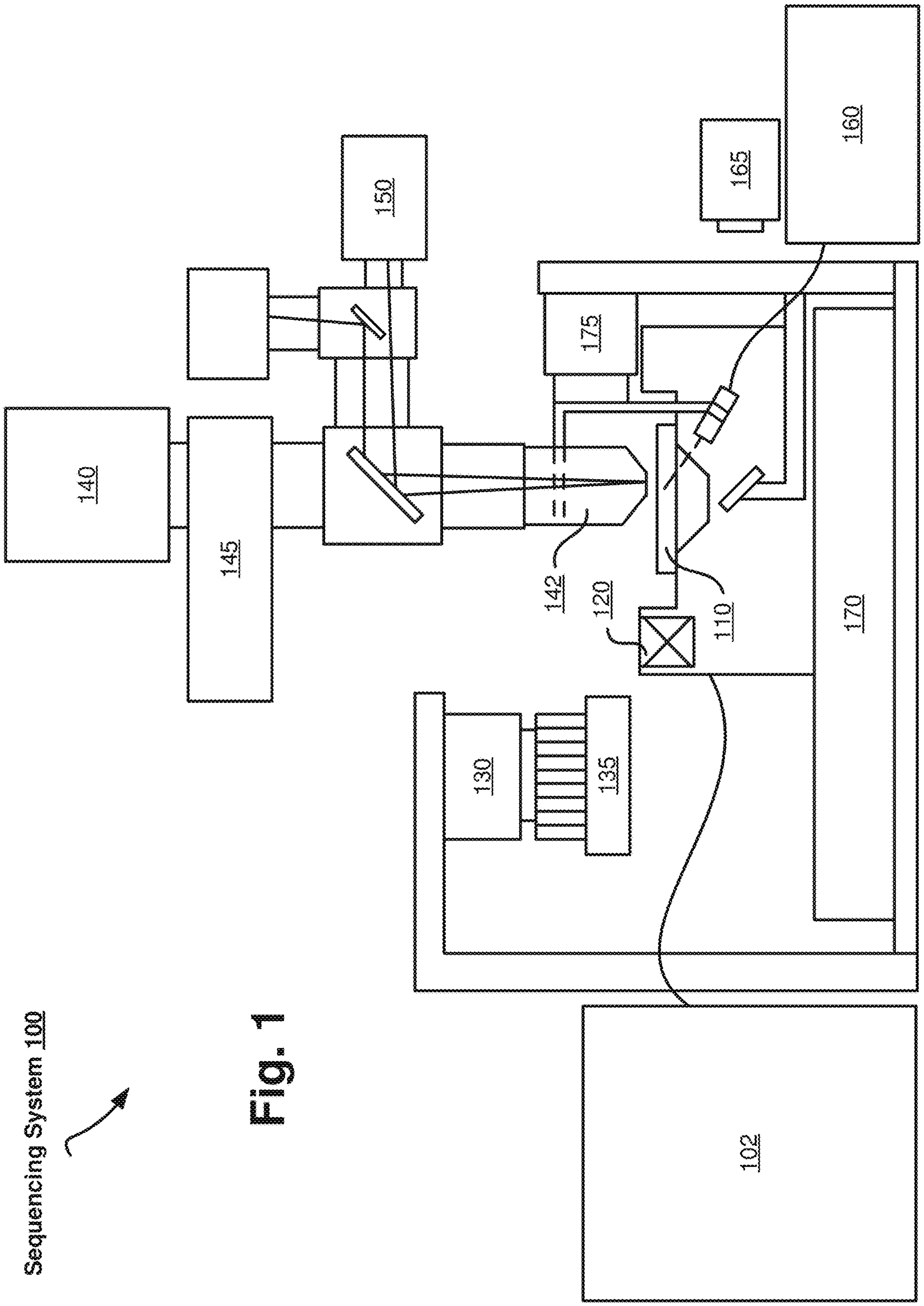
FIG. 1 shows an example sequencing environment with an imaging system.

The following discussion is presented to enable any person skilled in the art to make and use the technology disclosed and is provided in the context of a particular application and its requirements. Various modifications to the disclosed implementations will be readily apparent to those skilled in the art, and the general principles defined herein can be applied to other implementations and applications without departing from the spirit and scope of the technology disclosed. Thus, the technology disclosed is not intended to be limited to the implementations shown but is to be accorded the widest scope consistent with the principles and features disclosed herein.

We first describe signal profilers and then the disclosed specialist signal profilers.

Signal Profilers

As used herein, a "signal profiler" maximizes the signal-to-noise ratio of a signal that is disturbed by noise. A signal profiler can be a value or function that is applied to data to modify the data in a desired way. For example, the data can be modified to increase its accuracy, relevance, or applicability with regard to a particular situation. The signal profiler can be applied to the data by any of a variety of mathematical manipulations including, but not limited to addition, subtraction, division, multiplication, or a combination thereof. The signal profiler can be a mathematical formula, logic function, computer implemented algorithm, or the like. The data can be image data, electrical data, or a combination thereof.

In one implementation, the signal profiler is an equalizer (e.g., a spatial equalizer). The equalizer can be trained (e.g., using least square estimation, adaptive equalization algorithm) to maximize the signal-to-noise ratio of cluster intensity data in sequencing images. In some implementations, the equalizer is a lookup table (LUT) bank with a plurality of LUTs with subpixel resolution, also referred to as "equalizer filters" or "convolution kernels." In one implementation, the number of LUTs in the equalizer depends on the number of subpixels into which pixels of the sequencing images can be divided. For example, if the pixels are divisible into n by n subpixels (e.g., 5×5 subpixels), then the equalizer generates $n^2$ LUTs (e.g., 25 LUTs).

In one implementation of training the equalizer, data from the sequencing images is binned by well subpixel location. For example, for a 5×5 LUT, approximately 1/25th of the wells have a center that is in bin (1,1) (e.g., the upper left corner of a sensor pixel), 1/25th of the wells are in bin (1,2), and so on. In one implementation, the equalizer coefficients for each bin are determined using least squares estimation on the subset of data from the wells corresponding to the respective bins. This way the resulting estimated equalizer coefficients are different for each bin.

Each LUT/equalizer filter/convolution kernel has a plurality of coefficients that are learned from the training. In one implementation, the number of coefficients in a LUT corresponds to the number of pixels that are used for base calling a cluster. For example, if a local grid of pixels (image or pixel patch) that is used to base call a cluster is of size p×p (e.g., 9×9 pixel patch), then each LUT has $p^2$ coefficients (e.g., 81 coefficients).

In one implementation, the training produces equalizer coefficients that are configured to mix/combine intensity values of pixels that depict intensity emissions from a target cluster being base called and intensity emissions from one or more adjacent clusters in a manner that maximizes the signal-to-noise ratio. The signal maximized in the signal-to-noise ratio is the intensity emissions from the target cluster, and the noise minimized in the signal-to-noise ratio is the intensity emissions from the adjacent clusters, i.e., spatial crosstalk, plus some random noise (e.g., to account for background intensity emissions). The equalizer coefficients are used as weights and the mixing/combining includes executing element-wise multiplication between the equalizer coefficients and the intensity values of the pixels to calculate a weighted sum of the intensity values of the pixels, i.e., a convolution operation. Furthermore, in cases the image data spans across multiple color channels, a set of equalizer coefficients is generated for each color channel (e.g., one channel, three channels, four channels, etc.).

Figure 22:
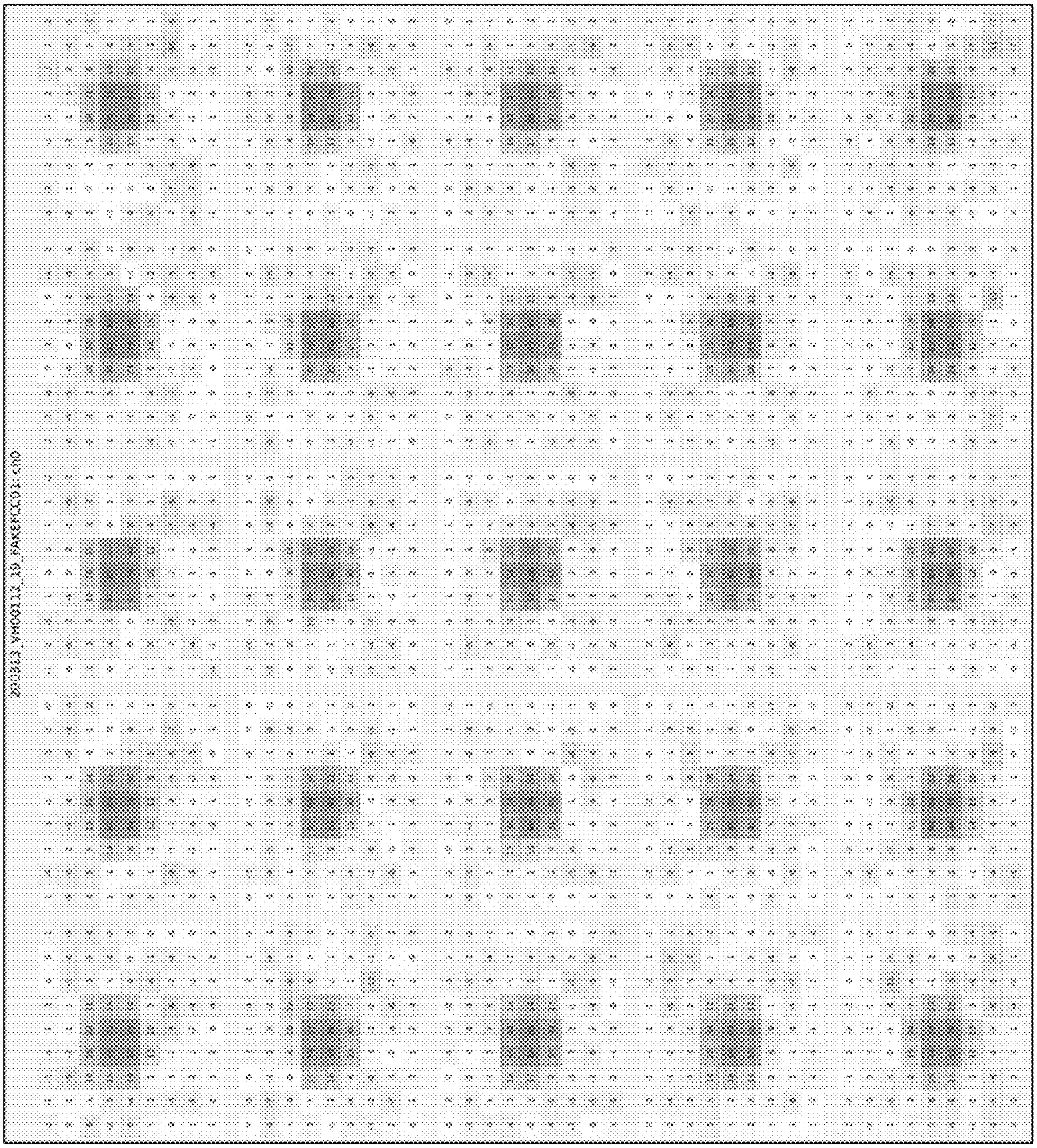
FIG. 22 shows equalizer coefficient sets of an example spatial equalizer.

FIG. 22 shows equalizer coefficient sets of an example spatial equalizer. As indicated by the heat maps, the different equalizer coefficient sets are configured to differently attenuate and augment signals of pixels depending on locations of the pixels.

Figure 23:
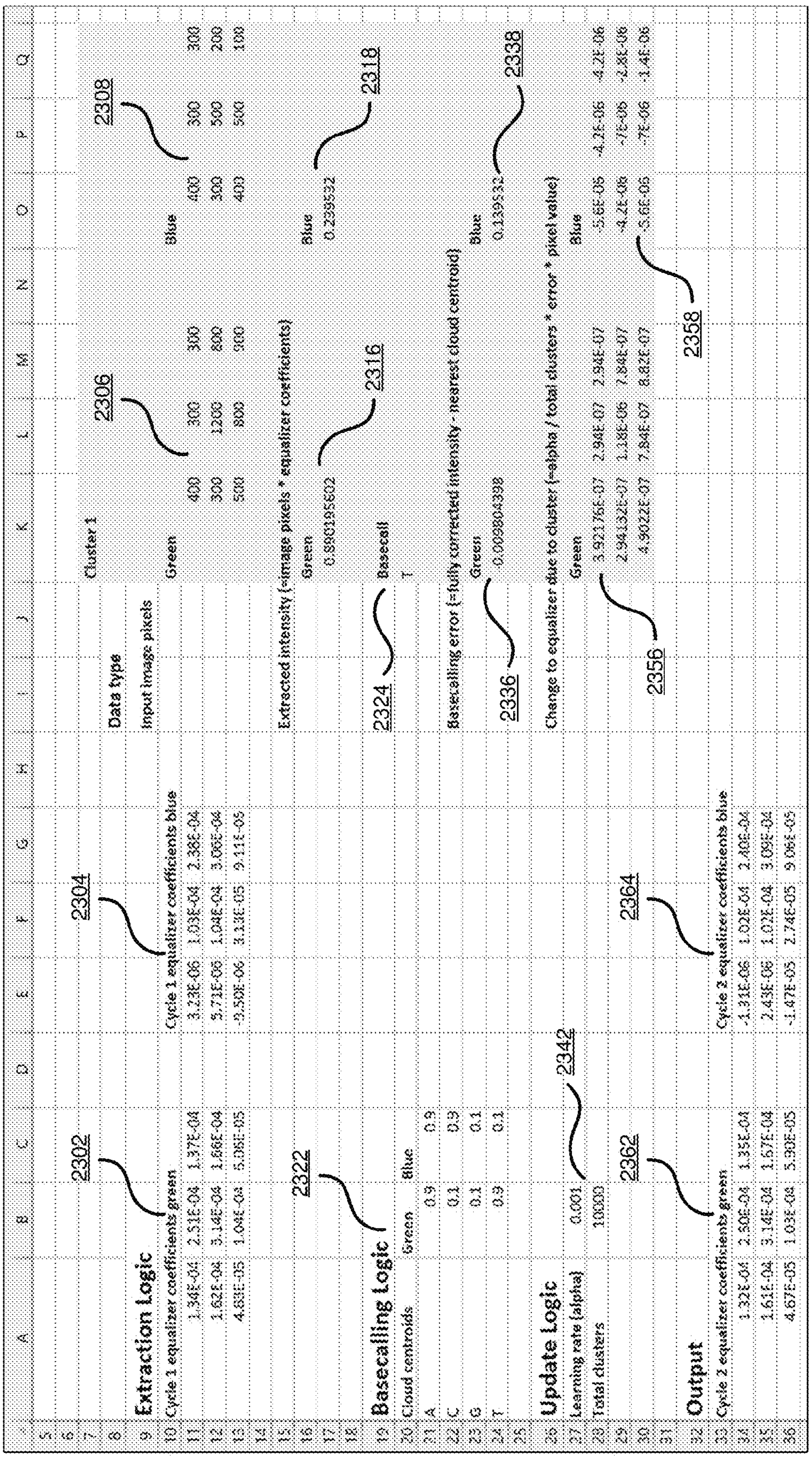
FIGS. 23-31 show one implementation of training an equalizer.

FIG. 23 shows one implementation of training an equalizer. For a first sequencing cycle (cycle 1), the equalizer in FIG. 23 has a first set of equalizer coefficients 2302 for the green color channel, and a second set of equalizer coefficients 2304 for the blue color channel. Also, for the first sequencing cycle (cycle 1), a first cluster (cluster 1) has input image pixels 2306 for the green color channel and input image pixels 2308 for the blue color channel.

Figure 24:
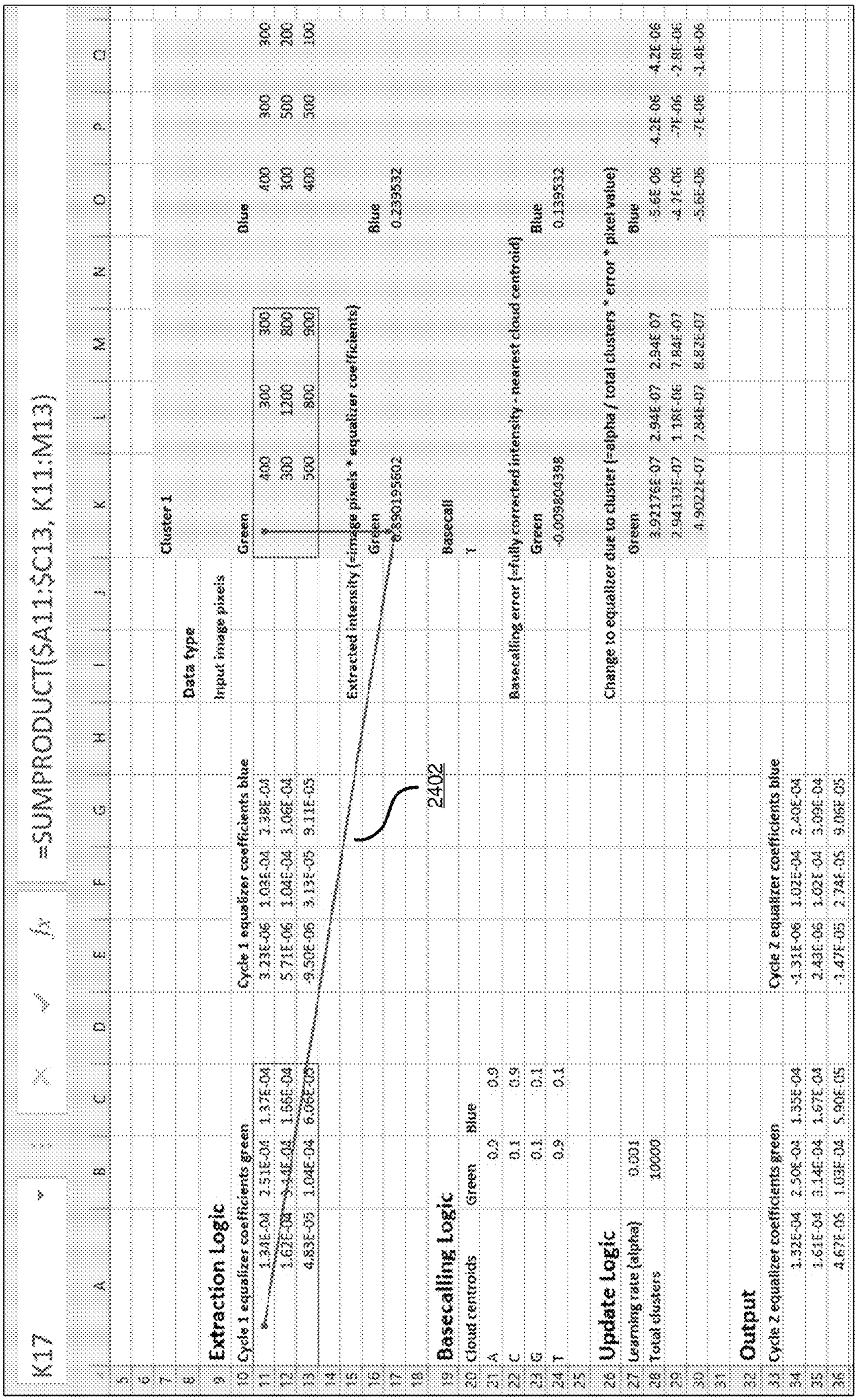
Figure 25:
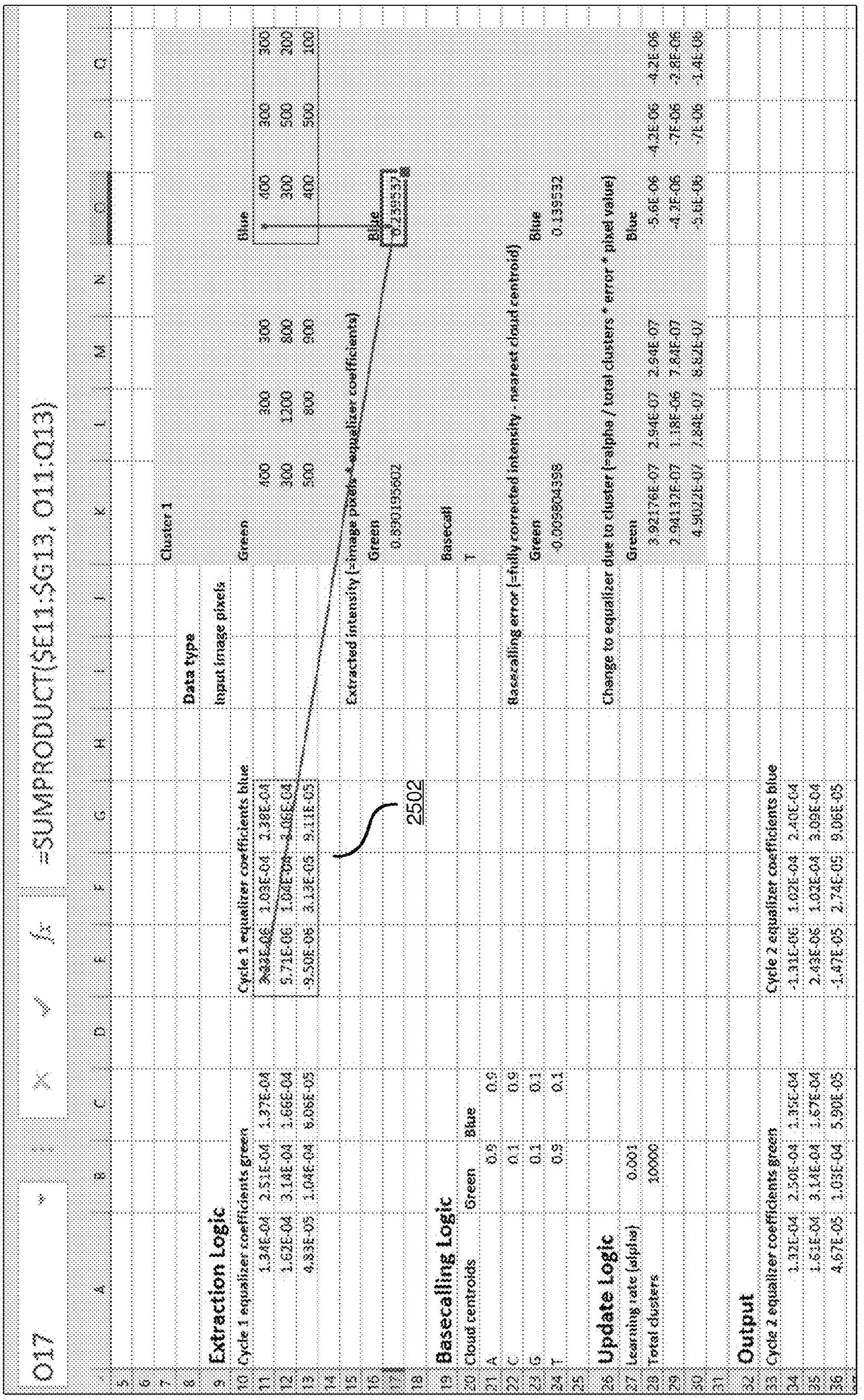

In FIG. 24, the first set of equalizer coefficients 2302 are element-wise multiplied 2402 with the input image pixels 2306 to generate a weighted sum 2316 for the green color channel. In FIG. 25, the second set of equalizer coefficients 2304 are element-wise multiplied 2502 with the input image pixels 2308 to generate a weighted sum 2318 for the blue color channel.

Figure 26:
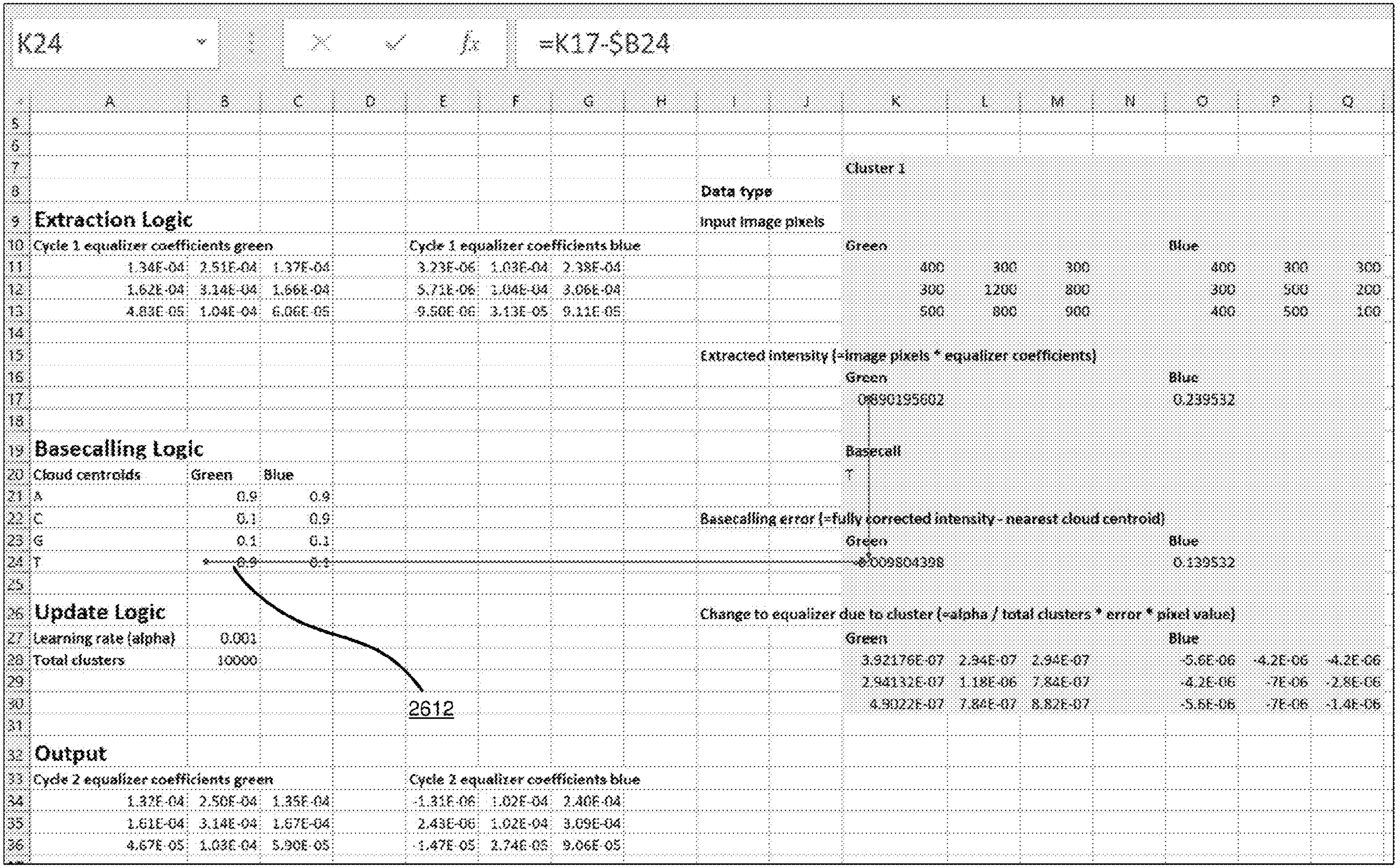
Figure 27:
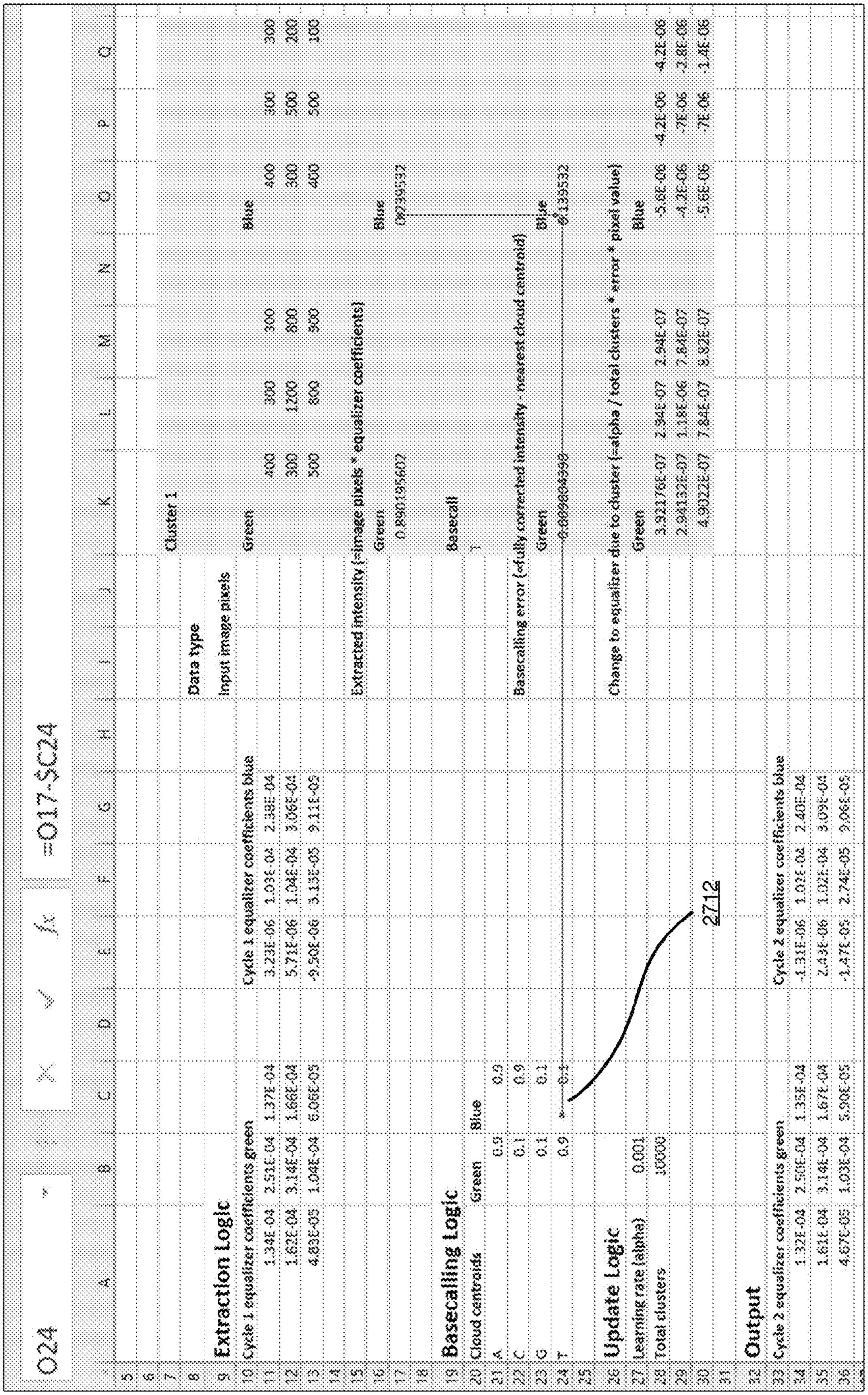

Then, a base calling logic 2322 uses the expectation maximization (EM) algorithm discussed above to predict a base call 2324 based on the weighted sums 2316, 2318. In FIG. 26, based on the predicted base call 2324, the weighted sum 2316 for the green color channel is compared against the centroid value 2612 of the called base for the green color channel with the base calling logic 2322. The comparison yields a base calling error 2336 for the green color channel. Also in FIG. 26, based on the predicted base call 2324, the weighted sum 2318 for the blue color channel is compared against the centroid value 2712 of the called base for the blue color channel with the base calling logic 2322. The comparison yields a base calling error 2338 for the blue color channel.

Figure 28:
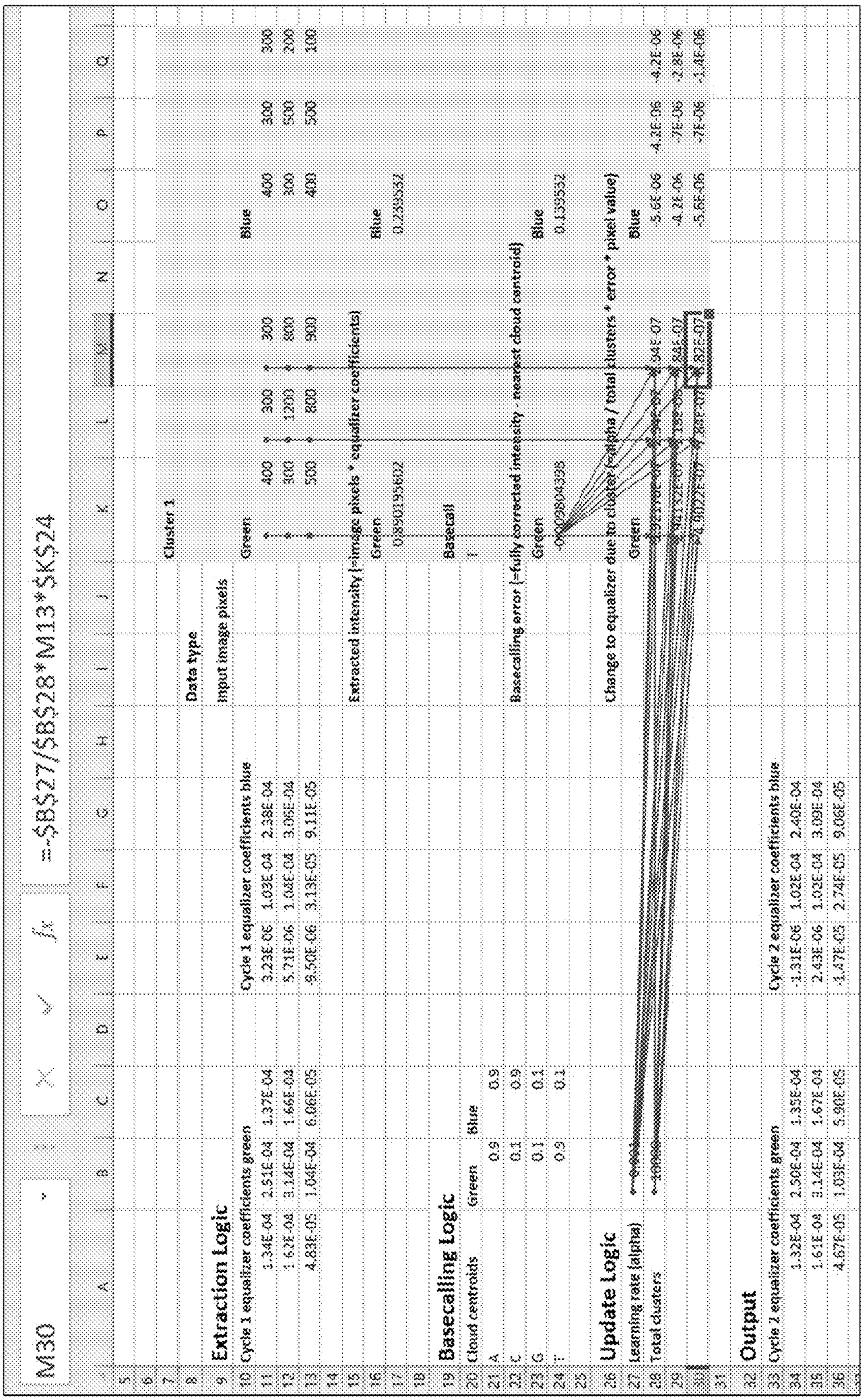
Figure 29:
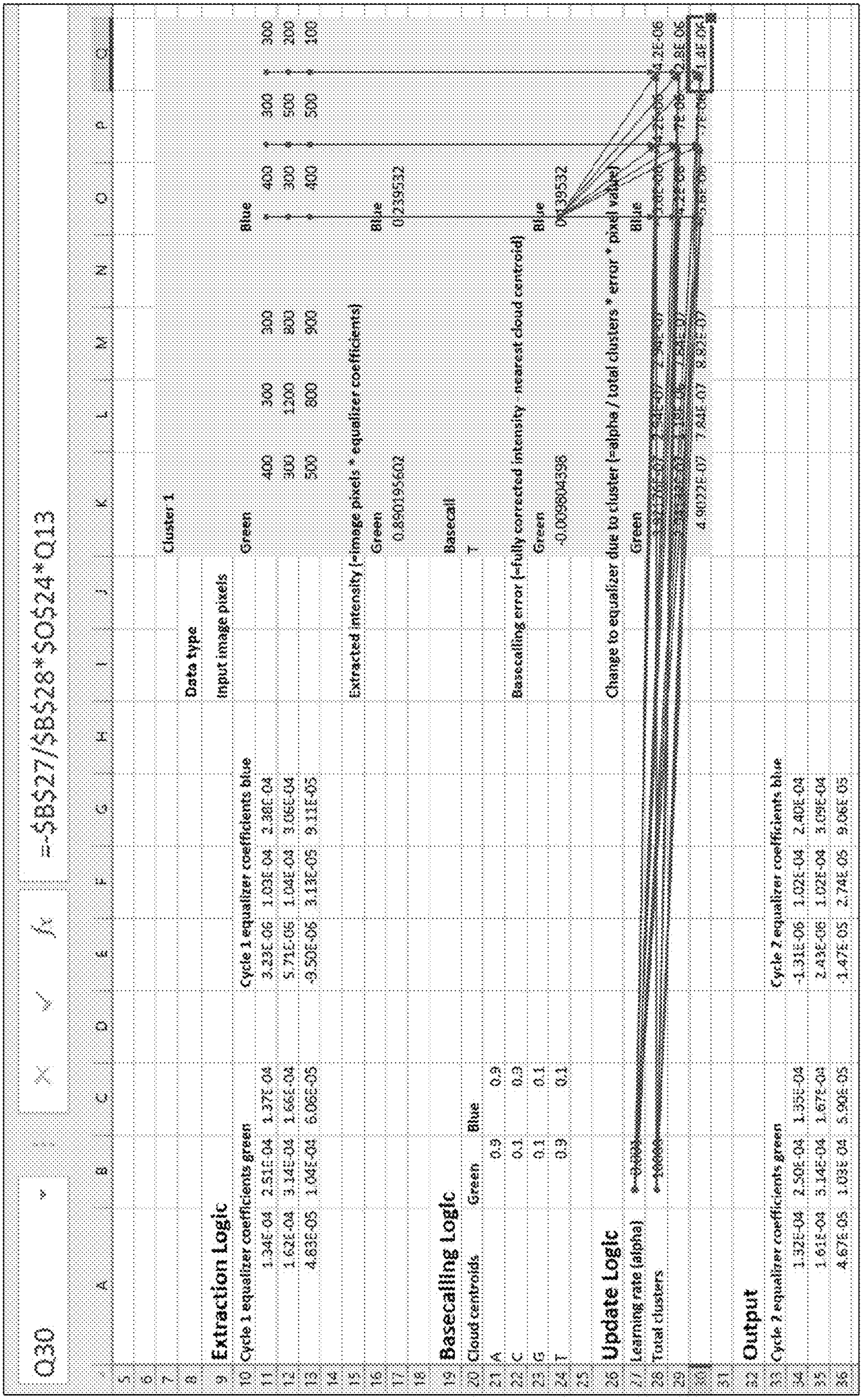

In FIGS. 28 and 29, the base calling errors 2336, 2338 are used by an update logic 2342 to produce an updated first set of equalizer coefficients 2356 for the green color channel, and an updated second set of equalizer coefficients 2358 for the blue color channel.

Figure 30:
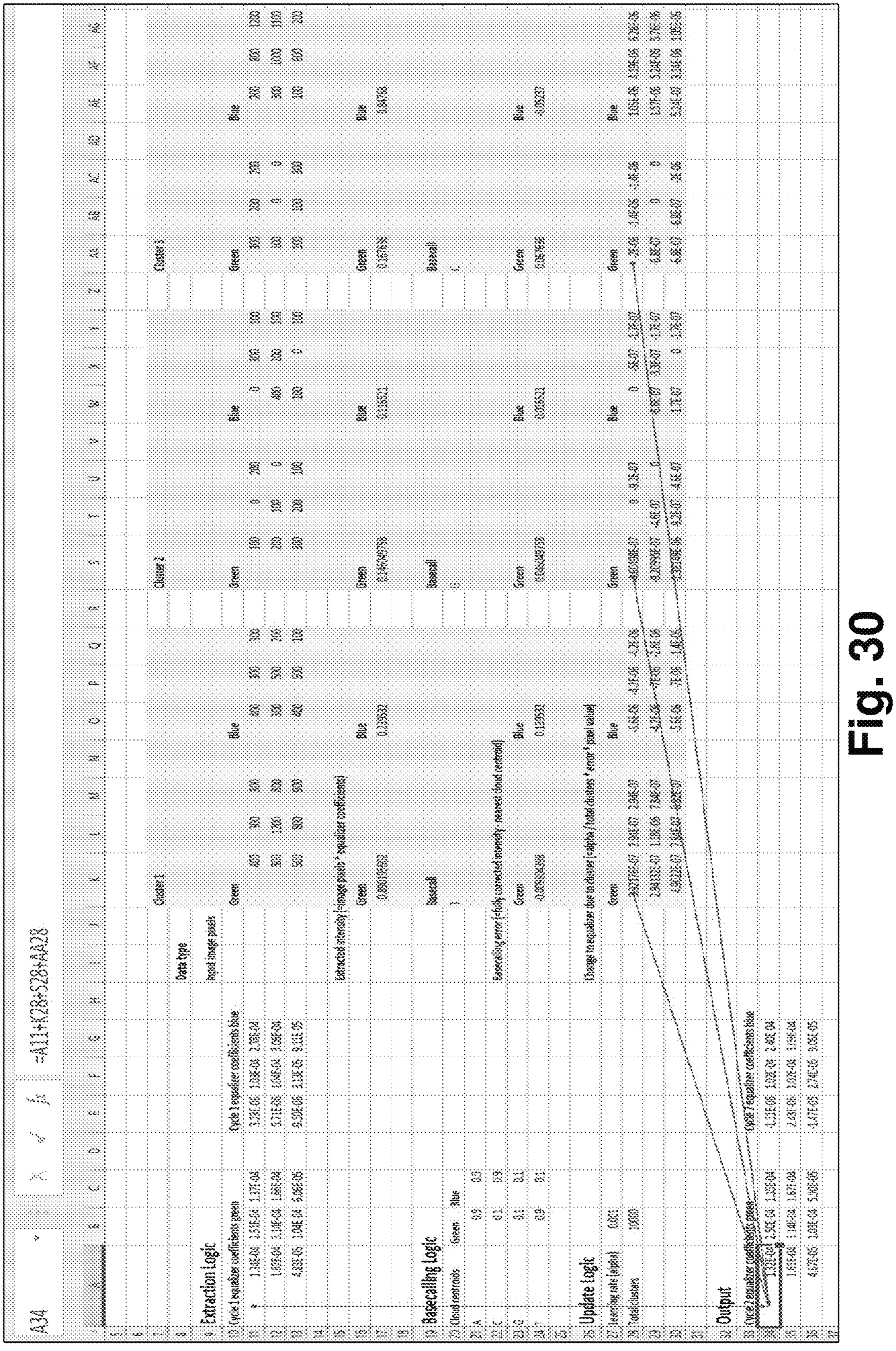
Figure 31:
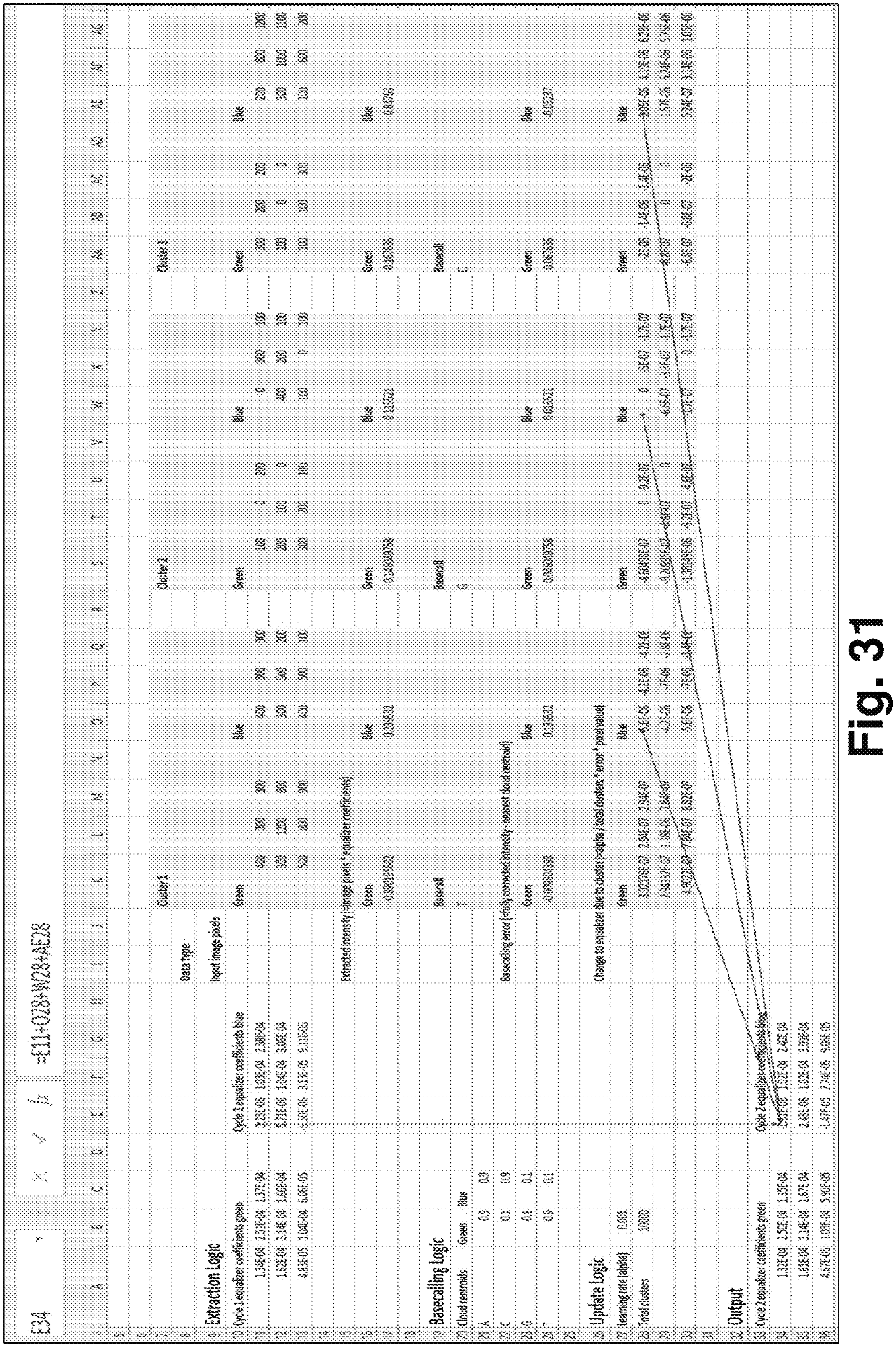

In some implementations, the above steps are executed for a plurality of clusters. For example, in the case of three clusters depicted in FIGS. 30 and 31, three updated versions of the first set of equalizer coefficients for the green color channel, and three updated versions of the second set of equalizer coefficients for the blue color channel are generated. The three updated versions are used to calculate, for a second sequencing cycle (cycle 2), a first set of equalizer coefficients 2362 for the green color channel, and a second set of equalizer coefficients 2364 for the blue color channel.

Figure 32B:
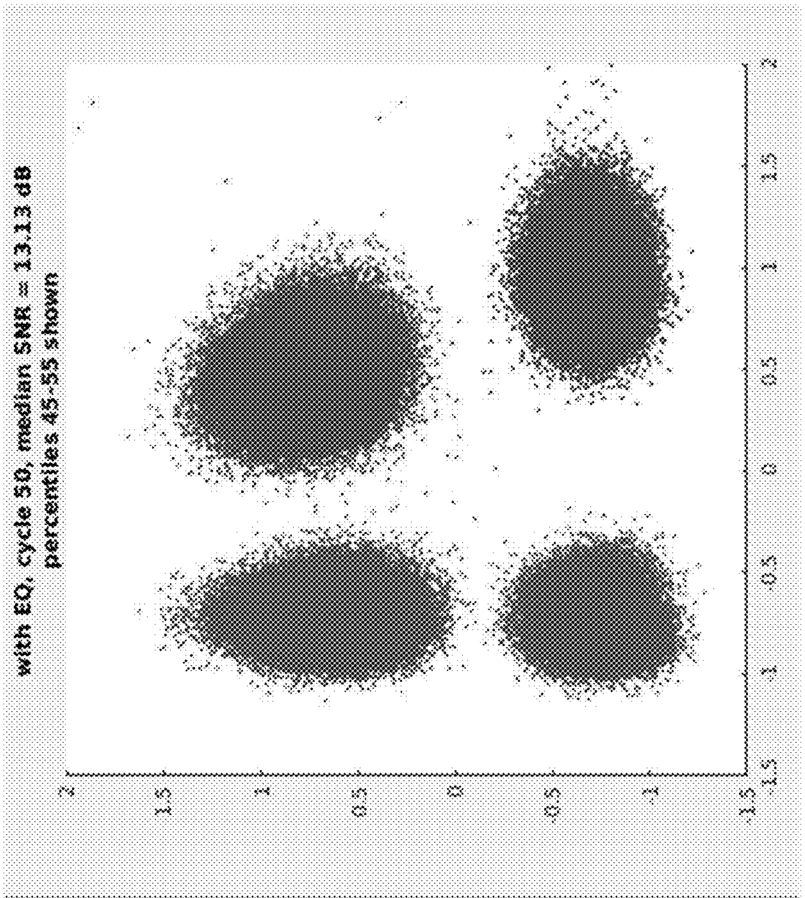
FIG. 32B shows the base-wise signal distributions of the same cluster population with the use of an equalizer, and with an improvement in the signal-to-noise ratio to 13.13 dBs.
Figure 32A:
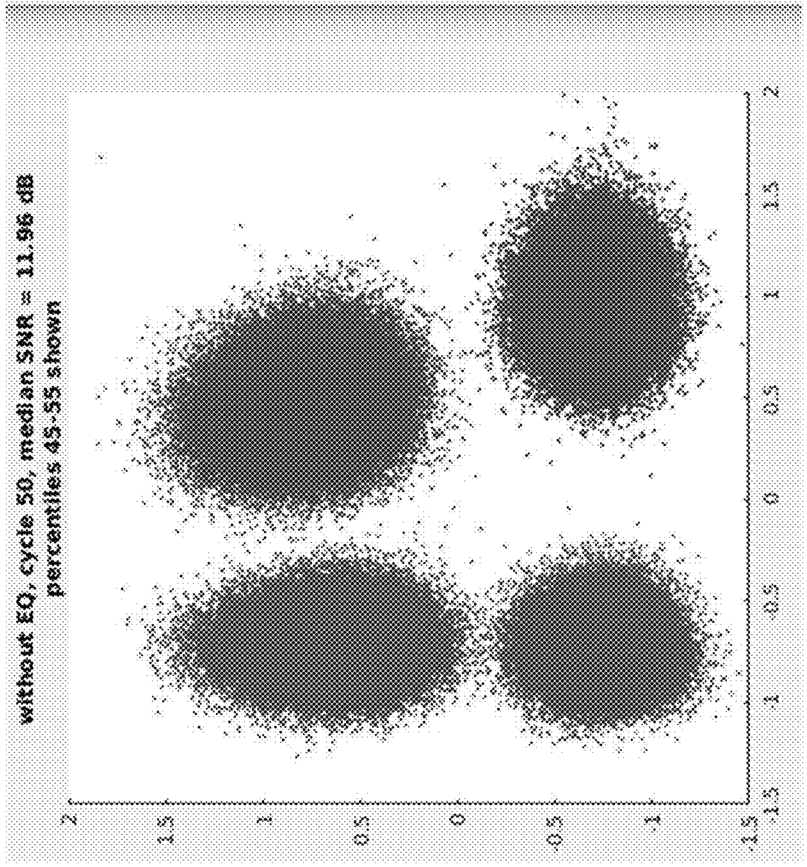
FIG. 32A shows base-wise signal distributions of a cluster population without use of an equalizer, and with a signal-to-noise ratio of 11.96 decibels (dBs).

FIG. 32A shows base-wise signal distributions of a cluster population without use of an equalizer, and with a signal-to-noise ratio of 11.96 decibels (dBs). FIG. 32B shows the base-wise signal distributions of the same cluster population with the use of an equalizer, and with an improvement in the signal-to-noise ratio to 13.13 dBs. The improvement in the signal-to-noise ratio is also visually observable by tighter/more discrete base-wise clouds/distributions in FIG. 32B compared to the base-wise clouds in FIG. 32A.

Additional details about the equalizer can be found in U.S. Nonprovisional patent application Ser. No. 17/308,035, titled "EQUALIZATION-BASED IMAGE PROCESSING AND SPATIAL CROSSTALK ATTENUATOR," filed May 4, 2021, which is incorporated by reference as if fully set forth herein.

The discussion now turns to the specialist signal profilers.

Specialist Signal Profilers

A global intensity correction applied at a pan-flow cell level or a pan-sequencing run level fails to consider a variety of noises in the image data. For example, non-linear distortion and noise can be induced by the shape of the optical lens that captures the image data. In addition, the imaged flow cell can also introduce distortion in the well pattern due to the manufacturing process, e.g., a 3D bathtub effect introduced by bonding or movement of the wells due to non-rigidity of the substrate. Finally, the tilt of the flow cell within the holder is not accounted for by the global intensity correction.

As used herein, a "specialist signal profiler" is a signal profiler that is configured to/trained to maximize the signal-to-noise ratio of a particular category/type/configuration/characteristic/class/bin of data. We disclose a variety of specialist signal profilers. For example, a "surface-specific specialist signal profiler" is configured to/trained to maximize the signal-to-noise ratio of sequencing data of clusters located on a particular surface or a particular surface-type/category/class (e.g., top surfaces or bottom surfaces or surfaces 1 to N of a flow cell). Similarly, a "lane-specific specialist signal profiler" is configured to/trained to maximize the signal-to-noise ratio of sequencing data of clusters located on a particular lane or a particular lane-type/category/class (e.g., central lanes or peripheral lanes or lanes 1 to N of a flow cell). Also, a "tile-specific specialist signal profiler" is configured to/trained to maximize the signal-to-noise ratio of sequencing data of clusters located on a particular tile or a particular tile-type/category/class (e.g., central tiles or peripheral tiles or tiles 1 to N of a flow cell). Also, a "sub-tile-specific specialist signal profiler" is configured to/trained to maximize the signal-to-noise ratio of sequencing data of clusters located on a particular sub-tile or a particular sub-tile-type/category/class (e.g., central sub-tiles or peripheral sub-tiles or sub-tiles 1 to N of a flow cell). More examples and details of the disclosed specialist signal profilers follow.

In some implementations, a single signal profiler can comprise a plurality of specialist coefficient sets, such that each specialist coefficient set is configured to/trained to maximize the signal-to-noise ratio of a particular category/type/configuration/characteristic/class/bin of data. In some implementations, the single signal profiler can comprise a variety of specialist coefficient sets. For example, a "surface-specific specialist coefficient set" is configured to/trained to maximize the signal-to-noise ratio of sequencing data of clusters located on a particular surface or a particular surface-type/category/class (e.g., top surfaces or bottom surfaces or surfaces 1 to N of a flow cell). Similarly, a "lane-specific specialist coefficient set" is configured to/trained to maximize the signal-to-noise ratio of sequencing data of clusters located on a particular lane or a particular lane-type/category/class (e.g., central lanes or peripheral lanes or lanes 1 to N of a flow cell). Also, a "tile-specific specialist coefficient set" is configured to/trained to maximize the signal-to-noise ratio of sequencing data of clusters located on a particular tile or a particular tile-type/category/class (e.g., central tiles or peripheral tiles or tiles 1 to N of a flow cell). Also, a "sub-tile-specific specialist coefficient set" is configured to/trained to maximize the signal-to-noise ratio of sequencing data of clusters located on a particular sub-tile or a particular sub-tile-type/category/class (e.g., central sub-tiles or peripheral sub-tiles or sub-tiles 1 to N of a flow cell). More examples and details of the disclosed specialist coefficient sets follow.

The disclosed specialist signal profilers are applicable to clusters located on both patterned and unpatterned surfaces of a flow cell. With unpatterned surfaces, the clusters are randomly distributed on the flow cell. The randomly distributed clusters and data therefor (e.g., images) can be binned spatially, temporally, signal-wise, or by any combination thereof. Accordingly, the specialist signal profilers can be configured and trained for different configurations of the differently binned randomly distributed clusters. With patterned surfaces, the clusters are located on patterned wells with fixed locations. The patterned wells and the constituent clusters can be binned spatially, temporally, signal-wise, or by any combination thereof. Accordingly, the specialist signal profilers can be configured and trained for different configurations of the differently binned patterned clusters.

The disclosed specialist signal profilers are configuration-specific signal profilers that are trained to maximize the signal-to-noise ratio of image data generated for different configurations of a sequencing run. These configurations can be spatial configurations relating to different regions on a flow cell, temporal configurations relating to different sequencing/imaging cycles of the sequencing run, signal distribution configurations relating to different distributions/patterns of signal profiles observed/encoded in the imaged data, or a combination thereof. Before describing various implementations of the systems and methods disclosed herein in greater detail, it is useful to describe an example environment with which the technology disclosed herein can be implemented.

Sequencing Environment

FIG. 1 shows an example sequencing environment with an imaging system 100. The example imaging system 100 can include a device for obtaining or producing an image of a sample. The example outlined in FIG. 1 shows an example imaging configuration of a backlight design implementation. It should be noted that although systems and methods can be described herein from time to time in the context of example imaging system 100, these are only examples with which implementations of the specialist signal profilers disclosed herein can be implemented.

As can be seen in the example of FIG. 1, subject samples are located on sample container 110 (e.g., a flow cell as described herein), which is positioned on a sample stage 170 under an objective lens 142. Light source 160 and associated optics direct a beam of light, such as laser light, to a chosen sample location on the sample container 110. The sample fluoresces and the resultant light is collected by the objective lens 142 and directed to an image sensor of camera system 140 to detect the florescence. Sample stage 170 is moved relative to objective lens 142 to position the next sample location on sample container 110 at the focal point of the objective lens 142. Movement of sample stage 110 relative to objective lens 142 can be achieved by moving the sample stage itself, the objective lens, some other component of the imaging system 100, or any combination of the foregoing. Further implementations can also include moving the entire imaging system 100 over a stationary sample.

Fluid delivery module or device 102 directs the flow of reagents (e.g., fluorescently labeled nucleotides, buffers, enzymes, cleavage reagents, etc.) to (and through) sample container 110 and waste valve 120. Sample container 110 can include one or more substrates upon which the samples are provided. For example, in the case of a system to analyze a large number of different nucleic acid sequences, sample container 110 can include one or more substrates on which nucleic acids to be sequenced are bound, attached, or associated. In various implementations, the substrate can include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the sample container 110.

In some implementations, the sample container 110 can include a biological sample that is imaged using one or more fluorescent dyes. For example, in a particular implementation, the sample container 110 can be implemented as a patterned flow cell including a translucent cover plate, a substrate, and a liquid sandwiched therebetween, and a biological sample can be located at an inside surface of the translucent cover plate or an inside surface of the substrate. The flow cell can include a large number (e.g., thousands, millions, or billions) of wells or regions that are patterned into a defined array (e.g., a hexagonal array, rectangular array, etc.) into the substrate. Each region can form a cluster (e.g., a monoclonal cluster) of a biological sample such as DNA, RNA, or another genomic material which can be sequenced, for example, using sequencing by synthesis. The flow cell can be further divided into a number of spaced apart lanes (e.g., eight lanes), each lane including a hexagonal array of clusters. Example flow cells that can be used in implementations disclosed herein are described in U.S. Pat. No. 8,778,848.

The system also comprises temperature station actuator 130 and heater/cooler 135 that can optionally regulate the temperature of conditions of the fluids within the sample container 110. Camera system 140 can be included to monitor and track the sequencing of sample container 110. Camera system 140 can be implemented, for example, as a charge-coupled device (CCD) camera (e.g., a time delay integration (TDI) CCD camera), which can interact with various filters within filter switching assembly 145, objective lens 142, and focusing laser/focusing laser assembly 150. Camera system 140 is not limited to a CCD camera and other cameras and image sensor technologies can be used. In particular implementations, the camera sensor can have a pixel size between about 5 and about 15 μm.

Output data from the sensors of camera system 140 can be communicated to a real time analysis module (not shown) that can be implemented as a software application that analyzes the image data (e.g., image quality scoring), reports or displays the characteristics of the laser beam (e.g., focus, shape, intensity, power, brightness, position) to a graphical user interface (GUI), and, as further described below, dynamically corrects intensity noise in the image data.

Light source 160 (e.g., an excitation laser within an assembly optionally comprising multiple lasers) or other light source can be included to illuminate fluorescent sequencing reactions within the samples via illumination through a fiber optic interface (which can optionally comprise one or more re-imaging lenses, a fiber optic mounting, etc.). Low watt lamp 165, focusing laser 150, and reverse dichroic are also presented in the example shown. In some implementations focusing laser 150 can be turned off during imaging. In other implementations, an alternative focus configuration can include a second focusing camera (not shown), which can be a quadrant detector, a Position Sensitive Detector (PSD), or similar detector to measure the location of the scattered beam reflected from the surface concurrent with data collection.

Although illustrated as a backlit device, other examples can include a light from a laser or other light source that is directed through the objective lens 142 onto the samples on sample container 110. Sample container 110 can be ultimately mounted on a sample stage 170 to provide movement and alignment of the sample container 110 relative to the objective lens 142. The sample stage can have one or more actuators to allow it to move in any of three dimensions. For example, in terms of the Cartesian coordinate system, actuators can be provided to allow the stage to move in the X, Y, and Z directions relative to the objective lens. This can allow one or more sample locations on sample container 110 to be positioned in optical alignment with objective lens 142.

A focus (z-axis) component 175 is shown in this example as being included to control positioning of the optical components relative to the sample container 110 in the focus direction (typically referred to as the z axis, or z direction). Focus component 175 can include one or more actuators physically coupled to the optical stage or the sample stage, or both, to move sample container 110 on sample stage 170 relative to the optical components (e.g., the objective lens 142) to provide proper focusing for the imaging operation. For example, the actuator can be physically coupled to the respective stage such as, for example, by mechanical, magnetic, fluidic, or other attachment or contact directly or indirectly to or with the stage. The one or more actuators can be configured to move the stage in the z-direction while maintaining the sample stage in the same plane (e.g., maintaining a level or horizontal attitude, perpendicular to the optical axis). The one or more actuators can also be configured to tilt the stage. This can be done, for example, so that sample container 110 can be leveled dynamically to account for any slope in its surfaces.

Focusing of the system generally refers to aligning the focal plane of the objective lens with the sample to be imaged at the chosen sample location. However, focusing can also refer to adjustments to the system to obtain a desired characteristic for a representation of the sample such as, for example, a desired level of sharpness or contrast for an image of a test sample. Because the usable depth of field of the focal plane of the objective lens can be small (sometimes on the order of 1 μm or less), focus component 175 closely follows the surface being imaged. Because the sample container is not perfectly flat as fixtured in the instrument, focus component 175 can be set up to follow this profile while moving along in the scanning direction (herein referred to as the y-axis).

The light emanating from a test sample at a sample location being imaged can be directed to one or more detectors of camera system 140. An aperture can be included and positioned to allow only light emanating from the focus area to pass to the detector. The aperture can be included to improve image quality by filtering out components of the light that emanate from areas that are outside of the focus area. Emission filters can be included in filter switching assembly 145, which can be selected to record a determined emission wavelength and to cut out any stray laser light.

Although not illustrated, a controller can be provided to control the operation of the scanning system. The controller can be implemented to control aspects of system operation such as, for example, focusing, stage movement, and imaging operations. In various implementations, the controller can be implemented using hardware, algorithms (e.g., machine executable instructions), or a combination of the foregoing. For example, in some implementations the controller can include one or more CPUs or processors with associated memory. As another example, the controller can comprise hardware or other circuitry to control the operation, such as a computer processor and a non-transitory computer readable medium with machine-readable instructions stored thereon. For example, this circuitry can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. As yet another example, the controller can comprise a combination of this circuitry with one or more processors.

Figure 2:
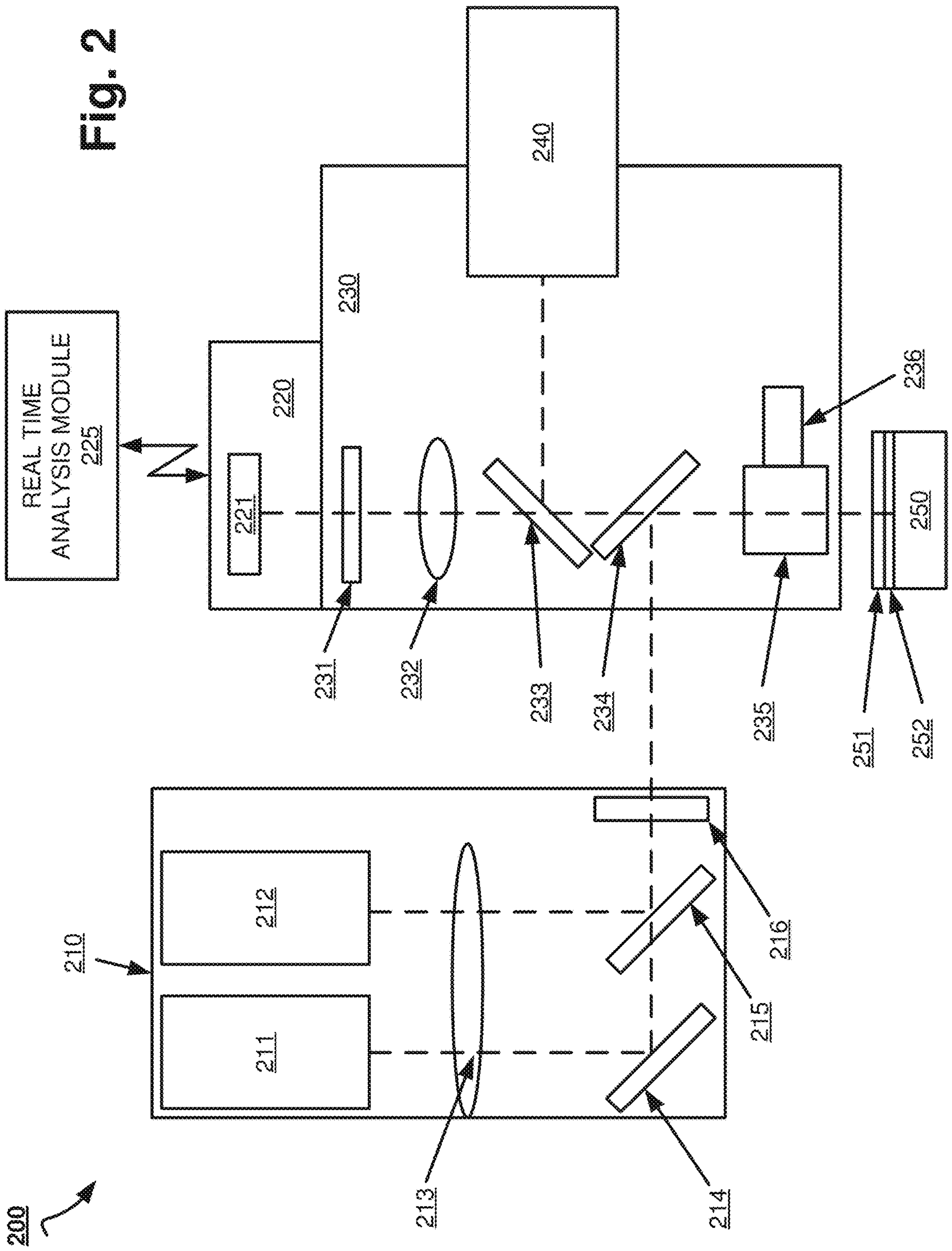
FIG. 2 is a block diagram illustrating an example two-channel, line-scanning modular optical imaging system that can be implemented in particular implementations.

FIG. 2 is a block diagram illustrating an example two-channel, line-scanning modular optical imaging system 200 that can be implemented in particular implementations. It should be noted that although systems and methods can be described herein from time to time in the context of example imaging system 200, these are only examples with which implementations of the technology disclosed herein can be implemented.

In some implementations, system 200 can be used for the sequencing of nucleic acids. Applicable techniques include those where nucleic acids are attached at fixed locations in an array (e.g., the wells of a flow cell) and the array is imaged repeatedly. In such implementations, system 200 can obtain images in two different color channels, which can be used to distinguish a particular nucleotide base type from another. More particularly, system 200 can implement a process referred to as "base calling," which generally refers to a process of a determining a base call (e.g., adenine (A), cytosine (C), guanine (G), or thymine (T)) for a given spot location of an image at an imaging cycle. During two-channel base calling, image data extracted from two images can be used to determine the presence of one of four base types by encoding base identity as a combination of the intensities of the two images. For a given spot or location in each of the two images, base identity can be determined based on whether the combination of signal identities is [on, on], [on, off], [off, on], or [off, off].

Referring again to imaging system 200, the system includes a line generation module (LGM) 210 with two light sources, 211 and 212, disposed therein. Light sources 211 and 212 can be coherent light sources such as laser diodes which output laser beams. Light source 211 can emit light in a first wavelength (e.g., a red color wavelength), and light source 212 can emit light in a second wavelength (e.g., a green color wavelength). The light beams output from laser sources 211 and 212 can be directed through a beam shaping lens or lenses 213. In some implementations, a single light shaping lens can be used to shape the light beams output from both light sources. In other implementations, a separate beam shaping lens can be used for each light beam. In some examples, the beam shaping lens is a Powell lens, such that the light beams are shaped into line patterns. The beam shaping lenses of LGM 210 or other optical components imaging system 200 be configured to shape the light emitted by light sources 211 and 212 into a line patterns (e.g., by using one or more Powel lenses, or other beam shaping lenses, diffractive or scattering components).

LGM 210 can further include mirror 214 and semi-reflective mirror 215 configured to direct the light beams through a single interface port to an emission optics module (EOM) 230. The light beams can pass through a shutter element 216. EOM 230 can include objective 235 and a z-stage 236 which moves objective 235 longitudinally closer to or further away from a target 250. For example, target 250 can include a liquid layer 252 and a translucent cover plate 251, and a biological sample can be located at an inside surface of the translucent cover plate as well an inside surface of the substrate layer located below the liquid layer. The z-stage can then move the objective as to focus the light beams onto either inside surface of the flow cell (e.g., focused on the biological sample). The biological sample can be DNA, RNA, proteins, or other biological materials responsive to optical sequencing as known in the art.

EOM 230 can include semi-reflective mirror 233 to reflect a focus tracking light beam emitted from a focus tracking module (FTM) 240 onto target 250, and then to reflect light returned from target 250 back into FTM 240. FTM 240 can include a focus tracking optical sensor to detect characteristics of the returned focus tracking light beam and generate a feedback signal to optimize focus of objective 235 on target 250.

EOM 230 can also include semi-reflective mirror 234 to direct light through objective 235, while allowing light returned from target 250 to pass through. In some implementations, EOM 230 can include a tube lens 232. Light transmitted through tube lens 232 can pass through filter element 231 and into camera module (CAM) 220. CAM 220 can include one or more optical sensors 221 to detect light emitted from the biological sample in response to the incident light beams (e.g., fluorescence in response to red and green light received from light sources 211 and 212).

Output data from the sensors of CAM 220 can be communicated to a real time analysis module 225. Real time analysis module, in various implementations, executes computer readable instructions for analyzing the image data (e.g., image quality scoring, base calling, etc.), reporting or displaying the characteristics of the beam (e.g., focus, shape, intensity, power, brightness, position) to a graphical user interface (GUI), etc. These operations can be performed in real-time during imaging cycles to minimize downstream analysis time and provide real time feedback and troubleshooting during an imaging run. In implementations, real time analysis module can be a computing device that is communicatively coupled to and controls imaging system 200. In implementations further described below, real time analysis module 225 can additionally execute computer readable instructions for maximizing the signal-to-noise ratio of the output image data received from CAM 220.

Sequencing produces m sequencing images per sequencing cycle for corresponding m image channels. That is, each of the sequencing images has one or more image (or intensity) channels (analogous to the red, green, blue (RGB) channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4. In other implementations, the images can be in blue and violet color channels instead of or in addition to the red and green channels.

Spatial Configuration-Specific Specialist Signal Profilers

Figure 3:
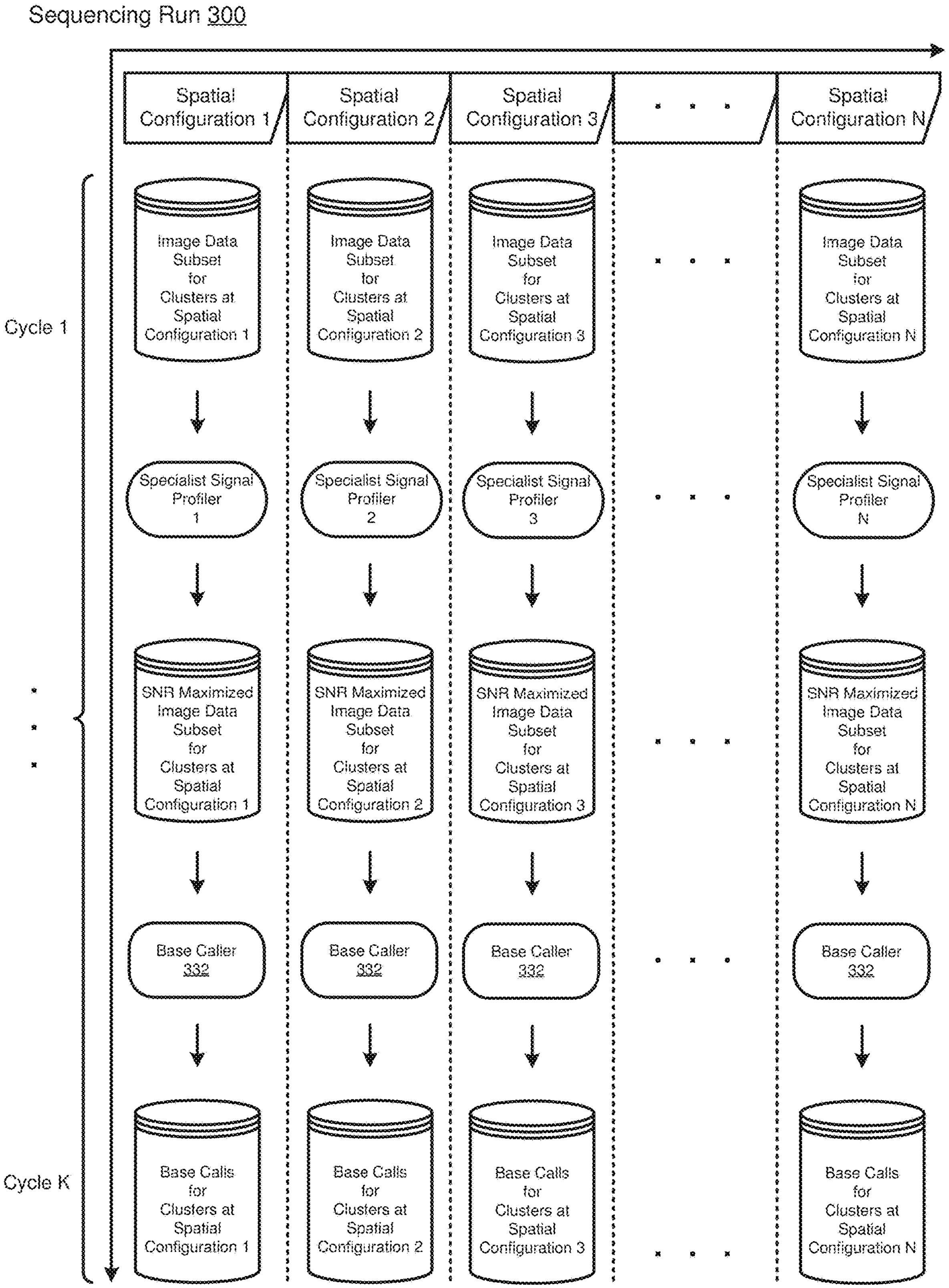
FIG. 3 shows one implementation of respective signal profilers 1 to N trained to maximize signal-to-noise ratio of respective image data subsets 1 to N generated for respective classes 1 to N of clusters located on a flow cell in respective spatial configurations 1 to N.

FIG. 3 shows one implementation of respective/separate/different/independent specialist signal profilers 1 to N trained to maximize signal-to-noise ratio of respective image data subsets 1 to N generated for respective classes 1 to N of clusters located on a flow cell in respective spatial configurations 1 to N. Sequencing run 300 sequences a population of clusters over a plurality of sequencing cycles/imaging cycles 1 to K and generates image data that depicts intensity emissions of the population of clusters.

Regarding the image data generated during the sequencing run 300, imaging cycle of the flow cell is performed such that the image data can be collected for the entire flow cell by scanning the flow cell area (e.g., using a line scanner), with one or more coherent sources of light. By way of example, the imaging system 200 can use LGM 210 in coordination with the optics of the system to line scan the flow cell with light having wavelengths within the red color spectrum and to line scan the sample with light having wavelengths within the green color spectrum. In response to line scanning, fluorescent dyes situated at the different clusters of the flow cell fluoresce and the resultant light can be collected by the objective lens 235 and directed to an image sensor of CAM 220 to detect the florescence. For example, fluorescence of each cluster can be detected by a few pixels of CAM 220. Image data output from CAM 220 can then be communicated to the real time analysis module 225 for image noise correction and base calling.

The population of clusters is spatially distributed across the flow cell. The flow cell, and therefore the population of clusters and the image data, is partitionable into different spatial configurations defined by different regions of the flow cell. So, for example, if the flow cell is partitionable into three rectangular regions, this would result in three spatial configurations of the flow cell, three sub-populations or classes of the clusters, three subsets of the image data, and three specialist signal profilers. At the next granular scale, each of the three rectangular regions of the flow cell can be further divided into three squares, resulting in a total of nine squares. This would in turn result in nine spatial configurations of the flow cell, nine sub-populations or classes of the clusters, nine subsets of the image data, and nine specialist signal profilers.

Regarding the segmentation of the image data, the image data is divided into a plurality of image data subsets corresponding to a respective region of the flow cell. In various implementations, the size of the image data subsets can be determined using the placement of fiducial markers or fiducials in the field of view of the imaging system 200, in the flow cell, or on the flow cell. The image data subsets can be divided such that the pixels of each image data subset have a predetermined number of fiducials (e.g., at least three fiducials, four fiducials, six fiducials, eight fiducials, etc.). For example, the total number of pixels of the image data subset may be predetermined based on predetermined pixel distances between the boundaries of the image data subset and the fiducials.

Furthermore, intensity data in each subset of image data can span across multiple color channels (e.g., red, blue, green, and/or violet image channels). Accordingly, each specialist signal profiler has a respective set of coefficients trained to maximize the signal-to-noise ratio of intensity data in a corresponding color channel.

During inference, new/unseen/wild image data is segmented on the same basis as the spatial configurations defined and used to generate the respective/separate/different/independent specialist signal profilers at training. The respective/separate/different/independent specialist signal profilers are applied to segmented new image data subsets in a way that the application of a particular specialist signal profiler is confined only to a corresponding new image data subset.

The application of the specialist signal profilers 1 to N to the image data subsets 1 to N generates signal-to-noise ratio maximized image data subsets 1 to N, additional details about which can be found in U.S. Nonprovisional patent application Ser. No. 17/308,035, titled "EQUALIZATION-BASED IMAGE PROCESSING AND SPATIAL CROSS-TALK ATTENUATOR," filed May 4, 2021. Other corrections for channel, spatial, or phasing noise can be applied in advance to the unprocessed image data, or subsequently to the signal-to-noise ratio maximized image data subsets 1 to N.

The output of the specialist signal profilers 1 to N, i.e., the signal-to-noise ratio maximized image data subsets 1 to N, are provided as input to a base caller 332 to produce base calls 1 to N for the population of clusters. Base calling may be performed by fitting a mathematical model to the intensity data. Suitable mathematical models that can be used include, for example, a k-means clustering algorithm, a k-means-like clustering algorithm, expectation maximization clustering algorithm, a histogram based method, and the like. Four Gaussian distributions may be fit to the set of two-channel intensity data such that one distribution is applied for each of the four nucleotides represented in the data set. In one particular implementation, an expectation maximization (EM) algorithm may be applied. As a result of the EM algorithm, for each X, Y value (referring to each of the two channel intensities respectively) a value can be generated which represents the likelihood that a certain X, Y intensity value belongs to one of four Gaussian distributions to which the data is fitted. Where four bases give four separate distributions, each X, Y intensity value will also have four associated likelihood values, one for each of the four bases. The maximum of the four likelihood values indicates the base call. For example, if a cluster is "off" in both channels, the base call is G. If the cluster is "off" in one channel and "on" in another channel the base call is either C or T (depending on which channel is on), and if the cluster is "on" in both channels the base call is A.

Figure 4:
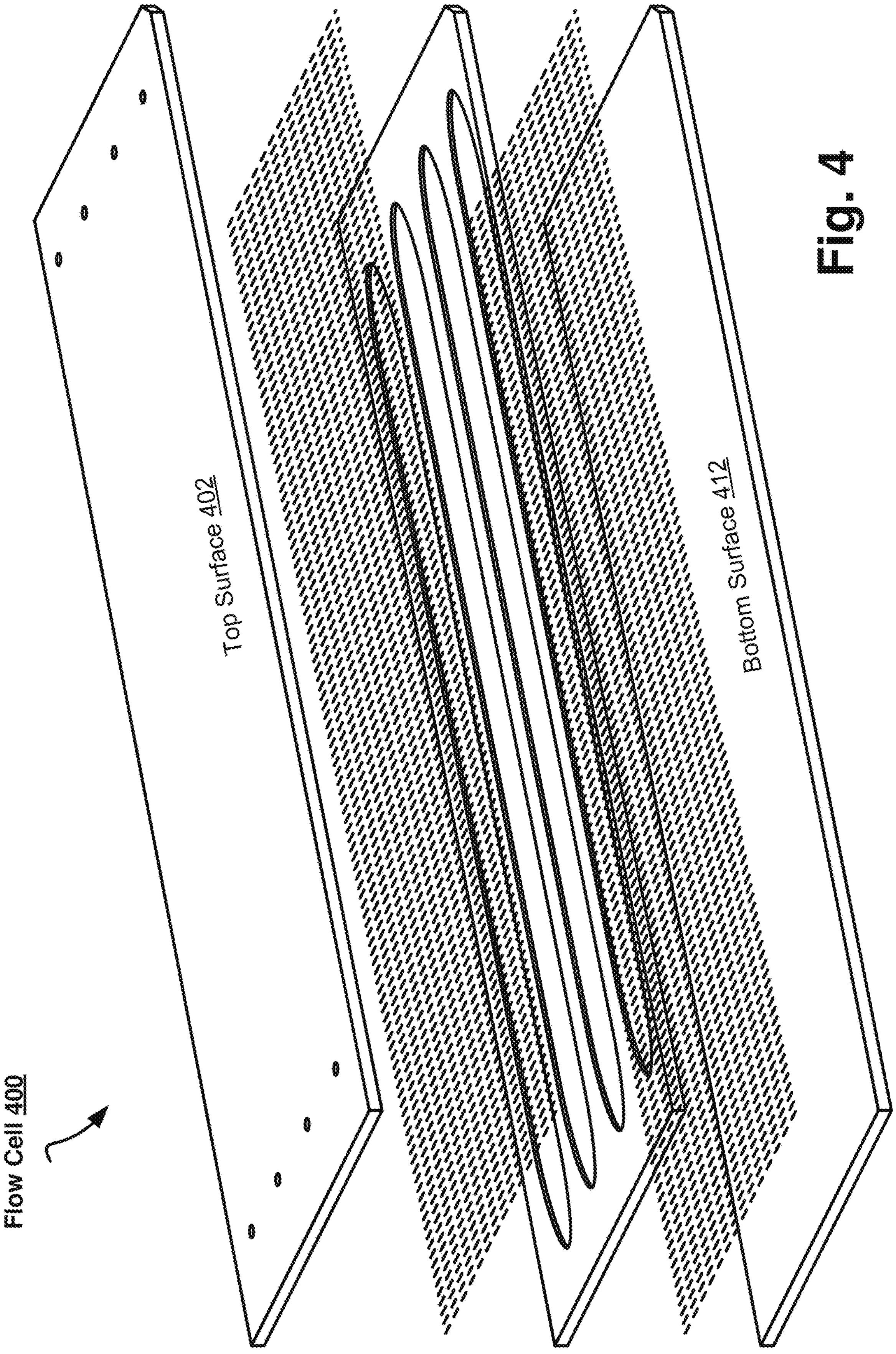
FIG. 4 illustrates an example configuration of a flow cell that can be imaged in accordance with implementations disclosed herein.

FIG. 4 illustrates an example configuration of a flow cell 400 that can be imaged in accordance with implementations disclosed herein. In some implementations, the flow cell 400 is patterned with a hexagonal array of ordered clusters or spots or features that can be simultaneously imaged during an imaging run. In other implementations, the flow cell 400 can be patterned using a rectilinear array, a circular array, an octagonal array, or some other array pattern. The flow cell 400 can have tens, hundreds, thousands, millions, or billions of clusters that are imaged. In a particular implementation, the flow cell 400 can be patterned with millions or billions of wells that are divided into lanes. In this particular implementation, each well of the flow cell 400 can contain at least one cluster.

Surface-Specific Specialist Signal Profilers

In some implementations, the flow cell 400 can be a multi-plane sample comprising multiple planes of clusters that are sampled during an imaging run. Examples of the multiple planes of clusters include a top surface 402 and a bottom surface 412. Accordingly, in one implementation, the flow cell 400 can have two spatial configurations corresponding to the top and bottom surfaces 402 and 412, which in turn result in two sub-populations or classes of the clusters, two subsets of the image data, and two specialist signal profilers.

Figures 6A, 6B:
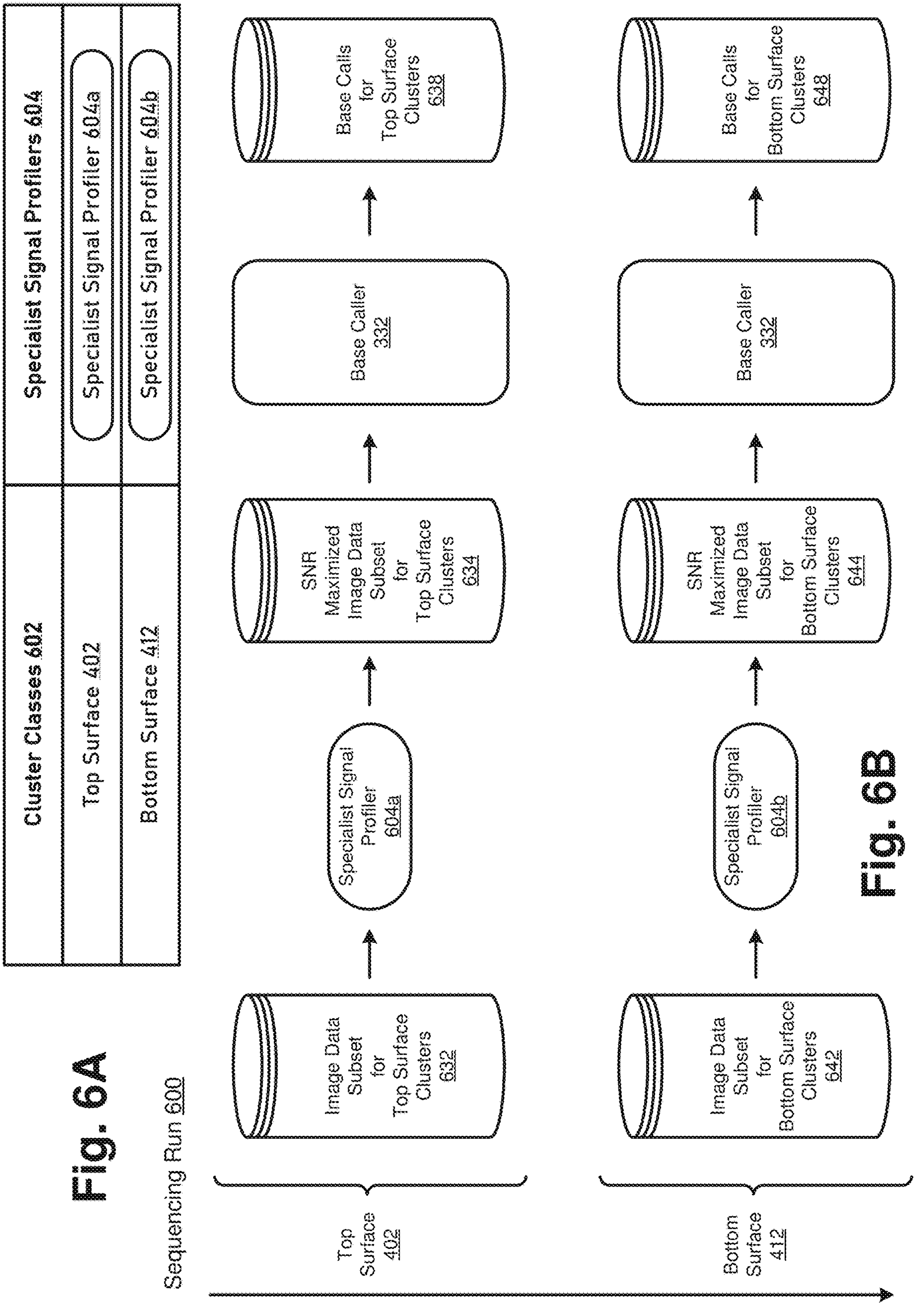
FIG. 6A shows one implementation of training respective surface-specific specialist signal profilers for respective cluster classes during a sequencing run 600.
FIG. 6B shows one implementation of applying the trained surface-specific specialist signal profilers to image data subsets corresponding to the respective cluster classes.

FIG. 6A shows one implementation of training respective surface-specific specialist signal profilers 604 for respective cluster classes 602. The respective cluster classes 602 include groups of clusters respectively located on the top surface 402, and clusters located on the bottom surface 412. What results is a first specialist signal profiler 604*a* configured to maximize the signal-to-noise ratio of intensity data of the clusters located on the top surface 402, and a second specialist signal profiler 604*b* configured to maximize the signal-to-noise ratio of intensity data of the clusters located on the bottom surface 412.

FIG. 6B shows one implementation of applying the trained surface-specific specialist signal profilers 604 to image data subsets 632, 642 corresponding to the respective cluster classes 602 during a sequencing run 600. In one implementation, the flow cell 400 is imaged at the tile-level. So, assuming that the top surface 402 has a first set of 1600 tiles and the bottom surface 412 has a second set of 1600 tiles, a first image data subset 632 includes a first set of 1600 tile images of the first set of 1600 tiles, and a second image data subset 642 includes a second set of 1600 tile images of the second set of 1600 tiles.

The first specialist signal profiler 604*a* is configured to maximize the signal-to-noise ratio of intensity data in the first image data subset 632 to generate a signal-to-noise ratio maximized version 634 of the first image data subset 632. The second specialist signal profiler 604*b* is configured to maximize the signal-to-noise ratio of intensity data in the second image data subset 642 to generate a signal-to-noise ratio maximized version 644 of the second image data subset 642. The base caller 332 processes the signal-to-noise ratio maximized versions 634, 644 and generates base calls 638, 648.

As used herein, the term "maximized version" refers to data produced as output by a specialist signal profiler. The maximized version of an input is an output produced by a specialist signal profiler in response to processing a corresponding input. The maximized version of the input has a signal-to-noise ratio (SNR, S/R) that is greater than the corresponding input processed by the specialist signal profiler. For example, the maximized version of the input (i.e., the output) produced by the specialist signal profiler is corrected by the specialist signal profiler to have less spatial crosstalk and background noise compared to the corresponding input. Similarly, the maximized version of the input (i.e., the output) produced by the specialist signal profiler is corrected by the specialist signal profiler to have less phasing and pre-phasing noise compared to the corresponding input.

Lane-Specific Specialist Signal Profilers

In one implementation, the top surface 402 can be divided or partitioned into a plurality of lanes 508*a*, 508*b*, . . . , 508*l*. In the example illustrated in FIG. 5A, the top surface 402 has eight lanes, although the number of lanes is implementation specific. Accordingly, in one implementation, the flow cell 400 can have sixteen spatial configurations corresponding to eight lanes of the top surface 402 and eight lanes of the bottom surface 412, which in turn result in sixteen sub-populations or classes of the clusters, sixteen subsets of the image data, and sixteen specialist signal profilers.

FIG. 7B shows one implementation of training respective lane-specific specialist signal profilers 714 for respective cluster classes 712. The respective cluster classes 712 include groups of clusters respectively located on the lanes 508*a*, 508*b*, . . . , 508*l*. What results is a first specialist signal profiler 714*a* configured to maximize the signal-to-noise ratio of intensity data of the clusters located on the first lane 508*a*, a second specialist signal profiler 714*b* configured to maximize the signal-to-noise ratio of intensity data of the clusters located on the second lane 508*b*, and so on (continuing to the $1^{th}$ specialist signal profiler 7141 configured to maximize the signal-to-noise ratio of intensity data of the clusters located on the $1^{th}$ lane 508*l*).

Figure 9:
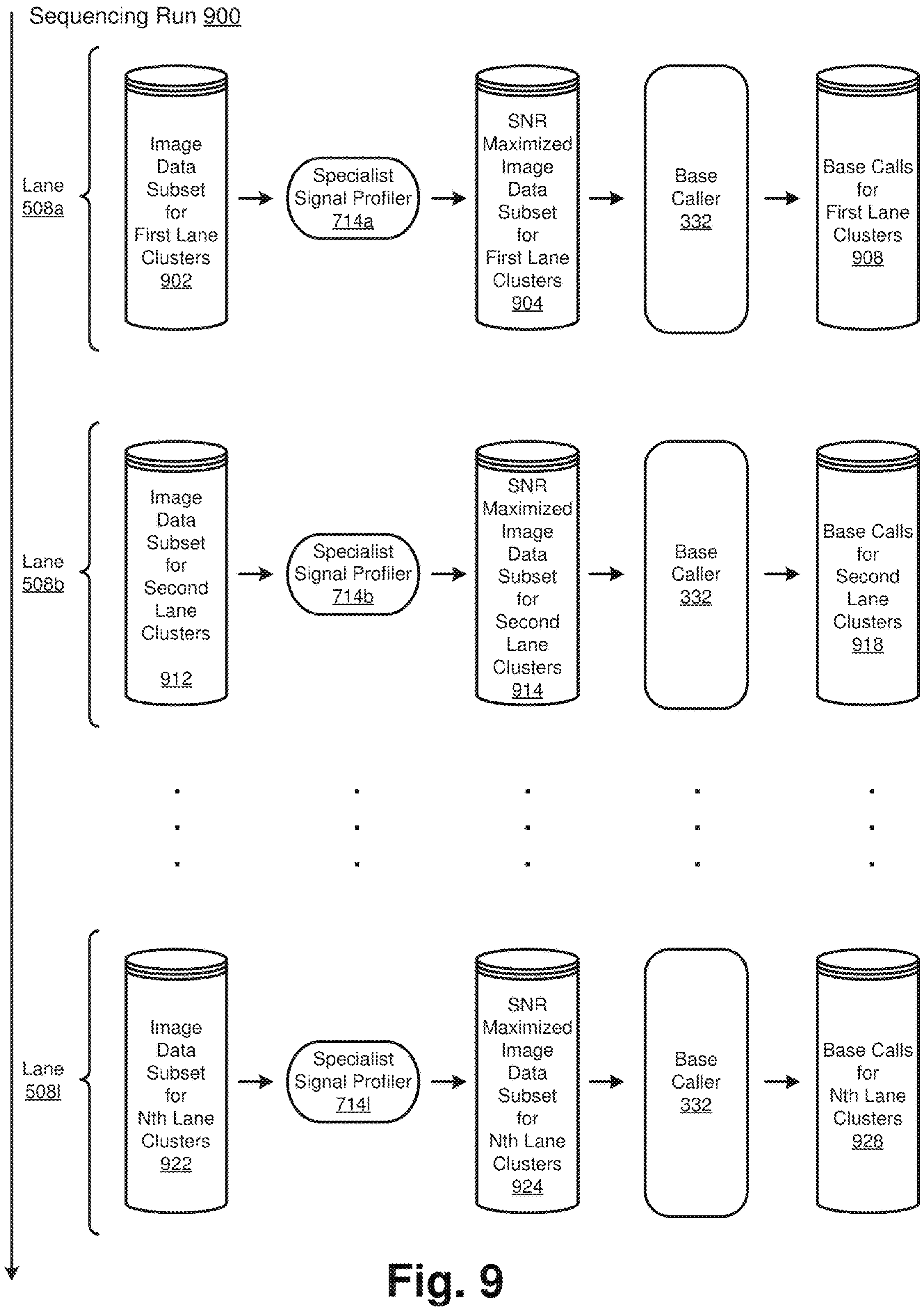
FIG. 9 shows one implementation of applying the trained lane-specific specialist signal profilers to image data subsets corresponding to the respective cluster classes during a sequencing run.

FIG. 9 shows one implementation of applying the trained lane-specific specialist signal profilers 714 to image data subsets 902, 912, . . . , 922 corresponding to the respective cluster classes 712 during a sequencing run 900. In one implementation, the flow cell 400 is imaged at the tile-level.

So, assuming that each lane has 200 tiles, a first image data subset 902 includes a first set of 200 tile images of the 200 tiles on the first lane 508*a*, a second image data subset 912 includes a second set of 200 tile images of the 200 tiles on the second lane 508*b*, and so on (continuing to the $l^{th}$ image data subset 922).

The first specialist signal profiler 714*a* is configured to maximize the signal-to-noise ratio of intensity data in the first image data subset 902 to generate a signal-to-noise ratio maximized version 904 of the first image data subset 902. The second specialist signal profiler 714*b* is configured to maximize the signal-to-noise ratio of intensity data in the second image data subset 912 to generate a signal-to-noise ratio maximized version 914 of the second image data subset 912, and so on (continuing to signal-to-noise ratio maximized version 924 of the $l^{th}$ image data subset 922). The base caller 332 processes the signal-to-noise ratio maximized versions 904, 914, . . . , 924 and generates base calls 908, 918, . . . , 928.

Lane Group-Specific Specialist Signal Profilers

In some implementations, the lanes can be grouped into lane groups 502*a*, 502*b*, and 502*c*. Examples of the lane groups include top peripheral lanes, central lanes, and bottom peripheral lanes. Accordingly, in one implementation, the flow cell 400 can have six spatial configurations corresponding to three lane groups of the top surface 402 and three lane groups of the bottom surface 412, which in turn result in six sub-populations or classes of the clusters, six subsets of the image data, and six specialist signal profilers.

FIG. 7A shows one implementation of training respective lane group-specific specialist signal profilers 704 for respective cluster classes 702. The respective cluster classes 702 include groups of clusters respectively located on the lane groups 502*a*, 502*b*, 502*c*. What results is a first specialist signal profiler 704*a* configured to maximize the signal-to-noise ratio of intensity data of the clusters located on the first lane group 502*a*, a second specialist signal profiler 704*b* configured to maximize the signal-to-noise ratio of intensity data of the clusters located on the second lane group 502*b*, and a third specialist signal profiler 704*c* configured to maximize the signal-to-noise ratio of intensity data of the clusters located on the third lane group 502*c*.

Figure 8:
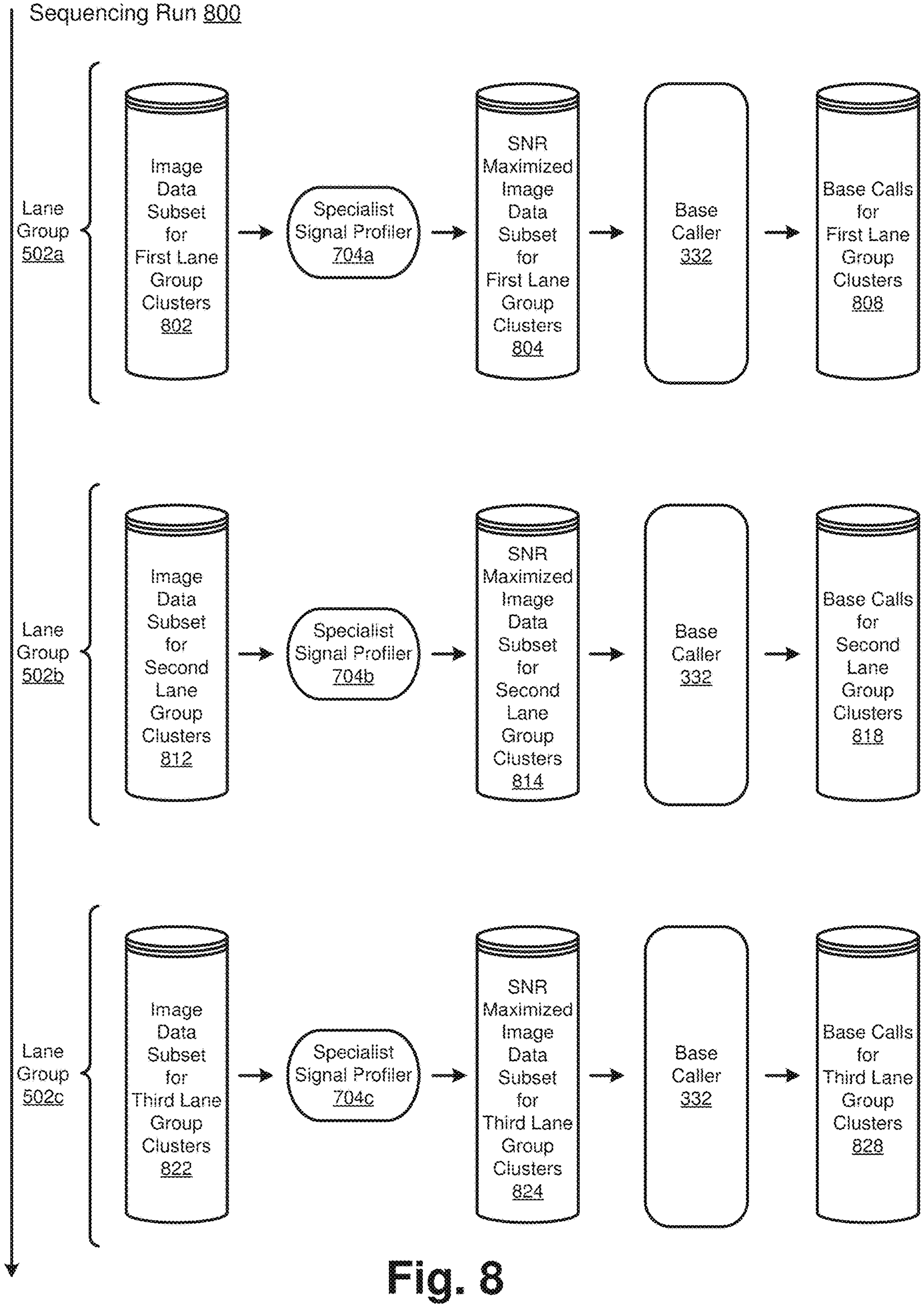
FIG. 8 shows one implementation of applying the trained lane group-specific specialist signal profilers to image data subsets corresponding to the respective cluster classes during a sequencing run.

FIG. 8 shows one implementation of applying the trained lane group-specific specialist signal profilers 704 to image data subsets 802, 812, 822 corresponding to the respective cluster classes 702 during a sequencing run 800. In one implementation, the flow cell 400 is imaged at the tile-level. So, assuming that the first lane group 502*a* has 600 tiles, the second lane group 502*b* has 600 tiles, and the third lane group 502*c* has 400 tiles, a first image data subset 802 includes a first set of 600 tile images of the 600 tiles on the first lane group 502*a*, a second image data subset 812 includes a second set of 600 tile images of the 600 tiles on the second lane group 502*b*, and a third image data subset 822 includes a third set of 400 tile images of the 400 tiles on the third lane group 502*c*.

The first specialist signal profiler 704*a* is configured to maximize the signal-to-noise ratio of intensity data in the first image data subset 802 to generate a signal-to-noise ratio maximized version 804 of the first image data subset 802. The second specialist signal profiler 704*b* is configured to maximize the signal-to-noise ratio of intensity data in the second image data subset 812 to generate a signal-to-noise ratio maximized version 814 of the second image data subset 812. The third specialist signal profiler 704*c* is configured to maximize the signal-to-noise ratio of intensity data in the third image data subset 822 to generate a signal-to-noise ratio maximized version 824 of the third image data subset 822. The base caller 332 processes the signal-to-noise ratio maximized versions 804, 814, 824 and generates base calls 808, 818, 828.

Swath-Specific Specialist Signal Profilers

Figures 5A, 5B, 5C, 5D:
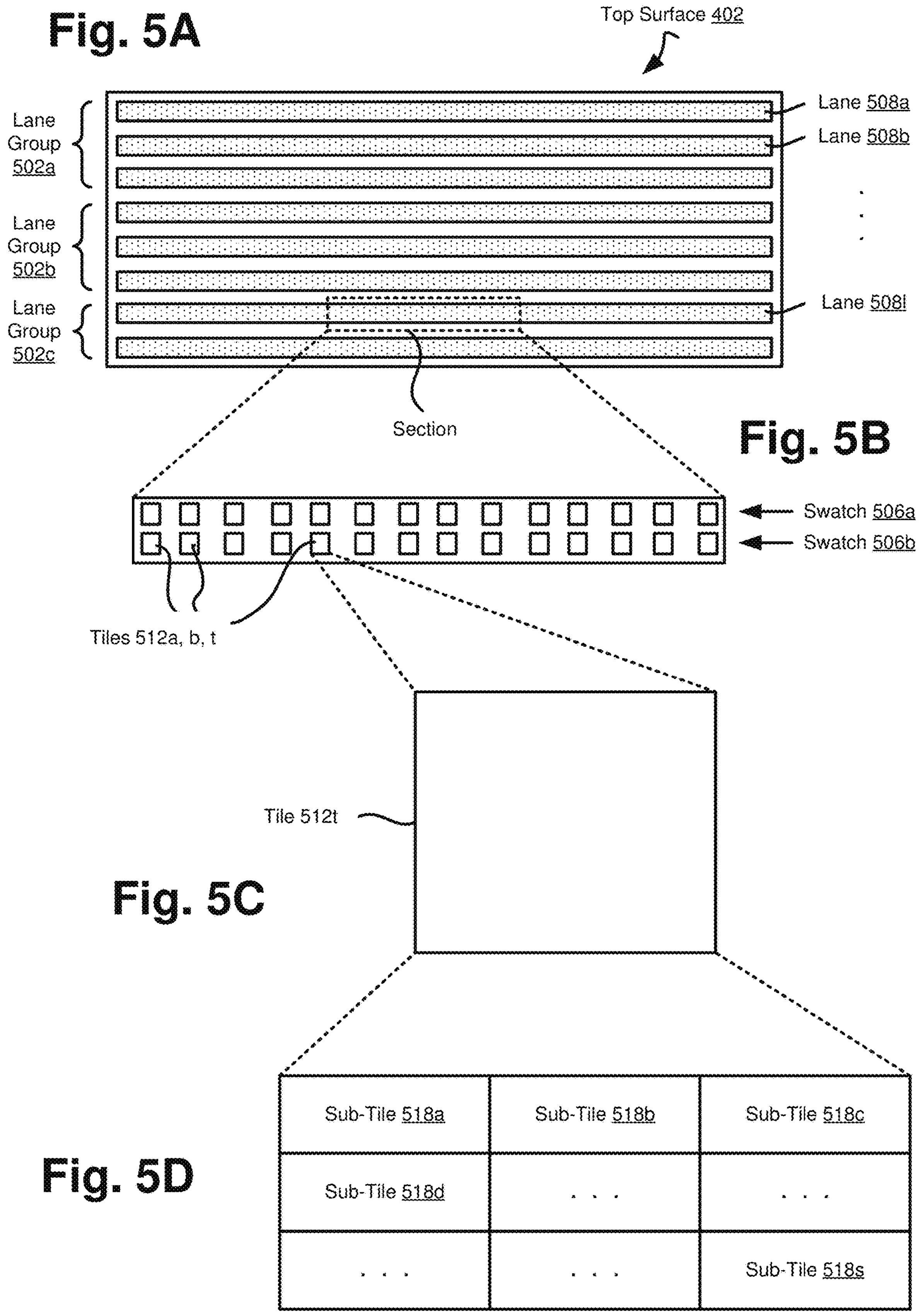
FIG. 5A depicts lanes of a top surface of a flow cell.
FIG. 5B shows swathes of tiles in a lane of a top surface of a flow cell.
FIG. 5C illustrates a tile in a swath of a lane of a top surface of a flow cell.
FIG. 5D portrays sub-tiles in a tile in a swath of a lane of a top surface of a flow cell.

In some implementations, each lane comprises one or more columns/swathes 506*a*, 506*b* of tiles, as shown in FIG. 5B. Accordingly, in one implementation, the flow cell 400 can have thirty-two spatial configurations corresponding to thirty-two swathes of tiles of the top surface 402 and thirty-two swathes of tiles of the bottom surface 412, which in turn result in thirty-two sub-populations or classes of the clusters, thirty-two subsets of the image data, and thirty-two specialist signal profilers.

FIG. 7C shows one implementation of training respective swath-specific specialist signal profilers 724 for respective cluster classes 722. The respective cluster classes 722 include groups of clusters respectively located on the swathes 506*a*, 506*b*. What results is a first specialist signal profiler 724*a* configured to maximize the signal-to-noise ratio of intensity data of the clusters located on the first swath 506*a*, and a second specialist signal profiler 724*b* configured to maximize the signal-to-noise ratio of intensity data of the clusters located on the second swath 506*b*.

Figure 10:
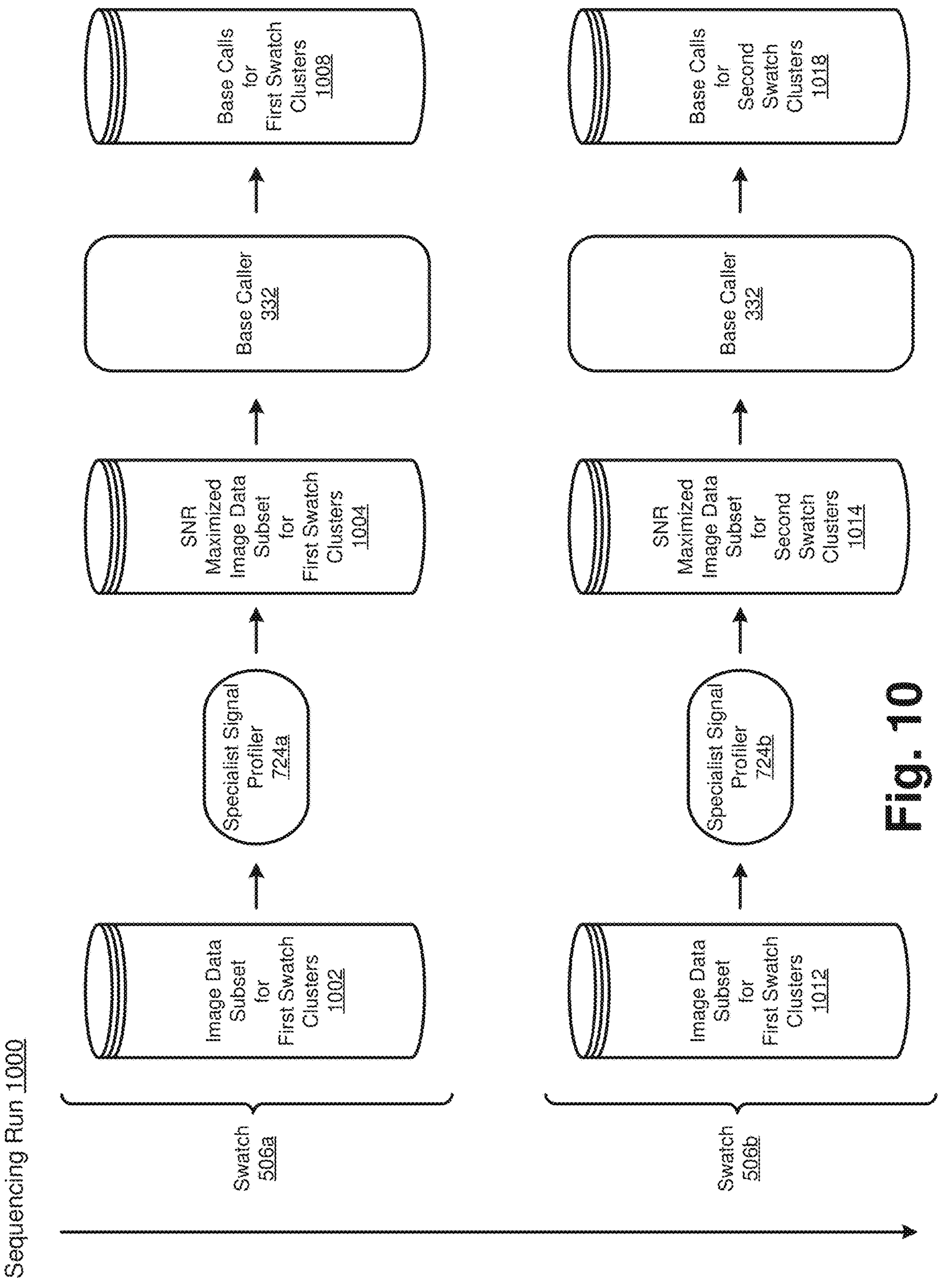
FIG. 10 shows one implementation of applying the trained swath-specific specialist signal profilers to image data subsets corresponding to the respective cluster classes during a sequencing run.

FIG. 10 shows one implementation of applying the trained swath-specific specialist signal profilers 724 to image data subsets 1002, 1012 corresponding to the respective cluster classes 722 during a sequencing run 1000. In one implementation, the flow cell 400 is imaged at the tile-level. So, assuming that the first swath 506*a* has 100 tiles, and the second swath 506*b* has 100 tiles, a first image data subset 1002 includes a first set of 100 tile images of the 100 tiles on the first swath 506*a*, and a second image data subset 1012 includes a second set of 100 tile images of the 100 tiles on the second swath 506*b*.

The first specialist signal profiler 724*a* is configured to maximize the signal-to-noise ratio of intensity data in the first image data subset 1002 to generate a signal-to-noise ratio maximized version 1004 of the first image data subset 1002. The second specialist signal profiler 724*b* is configured to maximize the signal-to-noise ratio of intensity data in the second image data subset 1012 to generate a signal-to-noise ratio maximized version 1014 of the second image data subset 1012. The base caller 332 processes the signal-to-noise ratio maximized versions 1004, 1014 and generates base calls 1008, 1018.

Tile-Specific Specialist Signal Profilers

Each swath comprises a plurality of tiles 512*a*, 512*b*, . . . , 512*t*, as shown in FIG. 5B. The number of tiles within each swath is implementation specific, and in different examples, there can be 50 tiles, 60 tiles, 80 tiles, and so on. Consider, for example, that each swath has 100 tiles. Then, the flow cell 400 will have 200 tiles per lane, resulting in 1600 tiles for the top surface 402 and another 1600 tiles for the bottom surface 412, i.e., a total of 3200 tiles. Accordingly, in one implementation, the flow cell 400 can have 3200 spatial configurations corresponding to the 3200 tiles, which in turn result in 3200 sub-populations or classes of the clusters, 3200 subsets of the image data, and 3200 specialist signal profilers.

FIG. 7D shows one implementation of training respective tile-specific specialist signal profilers 734 for respective cluster classes 732. The respective cluster classes 732 include groups of clusters respectively located on the tiles 512*a*, 512*b*, . . . , 512*t*. What results is a first specialist signal profiler 734*a* configured to maximize the signal-to-noise ratio of intensity data of the clusters located on the first tile 512*a*, a second specialist signal profiler 734*b* configured to maximize the signal-to-noise ratio of intensity data of the clusters located on the second tile 512*b*, and so on (continuing to the $t^{th}$ specialist signal profiler 734*t* configured to maximize the signal-to-noise ratio of intensity data of the clusters located on the $t^{th}$ tile 512*t*).

Figure 11:
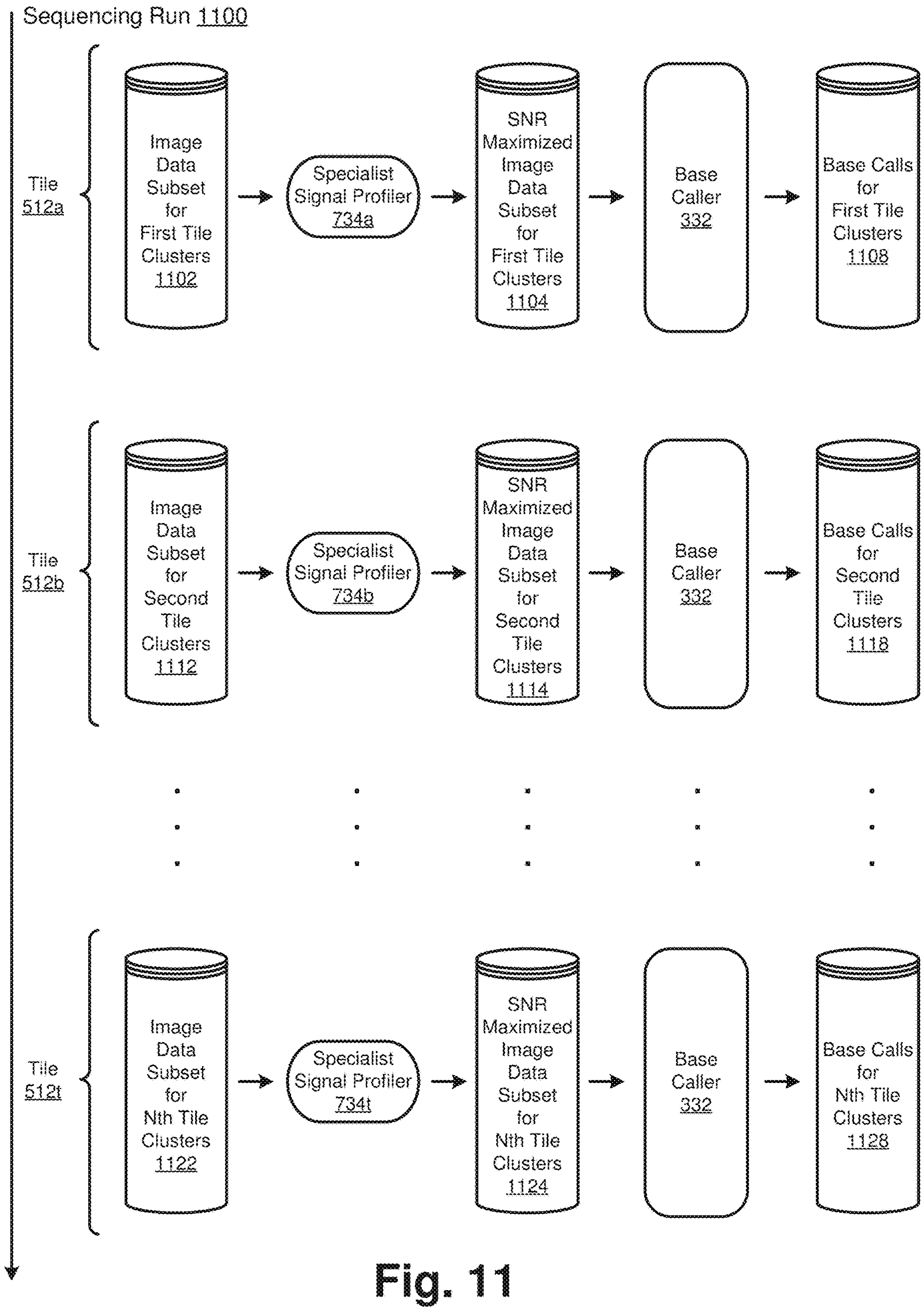
FIG. 11 shows one implementation of applying the trained tile-specific specialist signal profilers to image data subsets corresponding to the respective cluster classes during a sequencing run.

FIG. 11 shows one implementation of applying the trained tile-specific specialist signal profilers 734 to image data subsets 1102, 1112, . . . , 1122 corresponding to the respective cluster classes 732 during a sequencing run 1100. In one implementation, the flow cell 400 is imaged at the tile-level. So, for the tiles 512*a*, 512*b*, . . . , 512*t*, a first image data subset 1102 includes a first tile image of the first tile 512*a*, a second image data subset 1112 includes a second tile image of the second tile 512*b*, and so on (continuing to the $t^{th}$ image data subset 1122 comprising the $t^{th}$ tile image of the $t^{th}$ tile 512*t* (as shown in FIG. 5C)).

The first specialist signal profiler 734*a* is configured to maximize the signal-to-noise ratio of intensity data in the first image data subset 1102 to generate a signal-to-noise ratio maximized version 1104 of the first image data subset 1102. The second specialist signal profiler 734*b* is configured to maximize the signal-to-noise ratio of intensity data in the second image data subset 1112 to generate a signal-to-noise ratio maximized version 1114 of the second image data subset 1112, and so on (continuing to signal-to-noise ratio maximized version 1124 of the $t^{th}$ image data subset 1122). The base caller 332 processes the signal-to-noise ratio maximized versions 1104, 1114, . . . , 1124 and generates base calls 1108, 1118, . . . , 1128.

Sub-Tile-Specific Specialist Signal Profilers

Each tile can be divided into a plurality of sub-tiles 518*a*, 518*b*, . . . , 518*s*, as shown in FIG. 5D. The number of sub-tiles into which a tile can be divided is implementation specific, and in different examples, there can be 10 sub-tiles, 30 sub-tiles, 50 sub-tiles, and so on. Consider, for example, that each tile is divided into 9 sub-tiles. Then, the flow cell 400 will have a total of 28,800 sub-tiles for 3200 tiles. Accordingly, in one implementation, the flow cell 400 can have 28,800 spatial configurations corresponding to the 28,800 tiles, which in turn result in 28,800 sub-populations or classes of the clusters, 28,800 subsets of the image data, and 28,800 specialist signal profilers.

FIG. 7E shows one implementation of training respective sub-tile-specific specialist signal profilers 744 for respective cluster classes 742. The respective cluster classes 742 include groups of clusters respectively located on the sub-tiles 518*a*, 518*b*, 518*c*, 518*d*, . . . , 518*s*. What results is a first specialist signal profiler 744*a* configured to maximize the signal-to-noise ratio of intensity data of the clusters located on the first sub-tile 518*a*, a second specialist signal profiler 744*b* configured to maximize the signal-to-noise ratio of intensity data of the clusters located on the second sub-tile 518*b*, a third specialist signal profiler 744*c* configured to maximize the signal-to-noise ratio of intensity data of the clusters located on the third sub-tile 518*c*, a fourth specialist signal profiler 744*d* configured to maximize the signal-to-noise ratio of intensity data of the clusters located on the fourth sub-tile 518*d*, and so on (continuing to the $s^{th}$ specialist signal profiler 744*s* configured to maximize the signal-to-noise ratio of intensity data of the clusters located on the $s^{th}$ sub-tile 518*s*).

Figure 12:
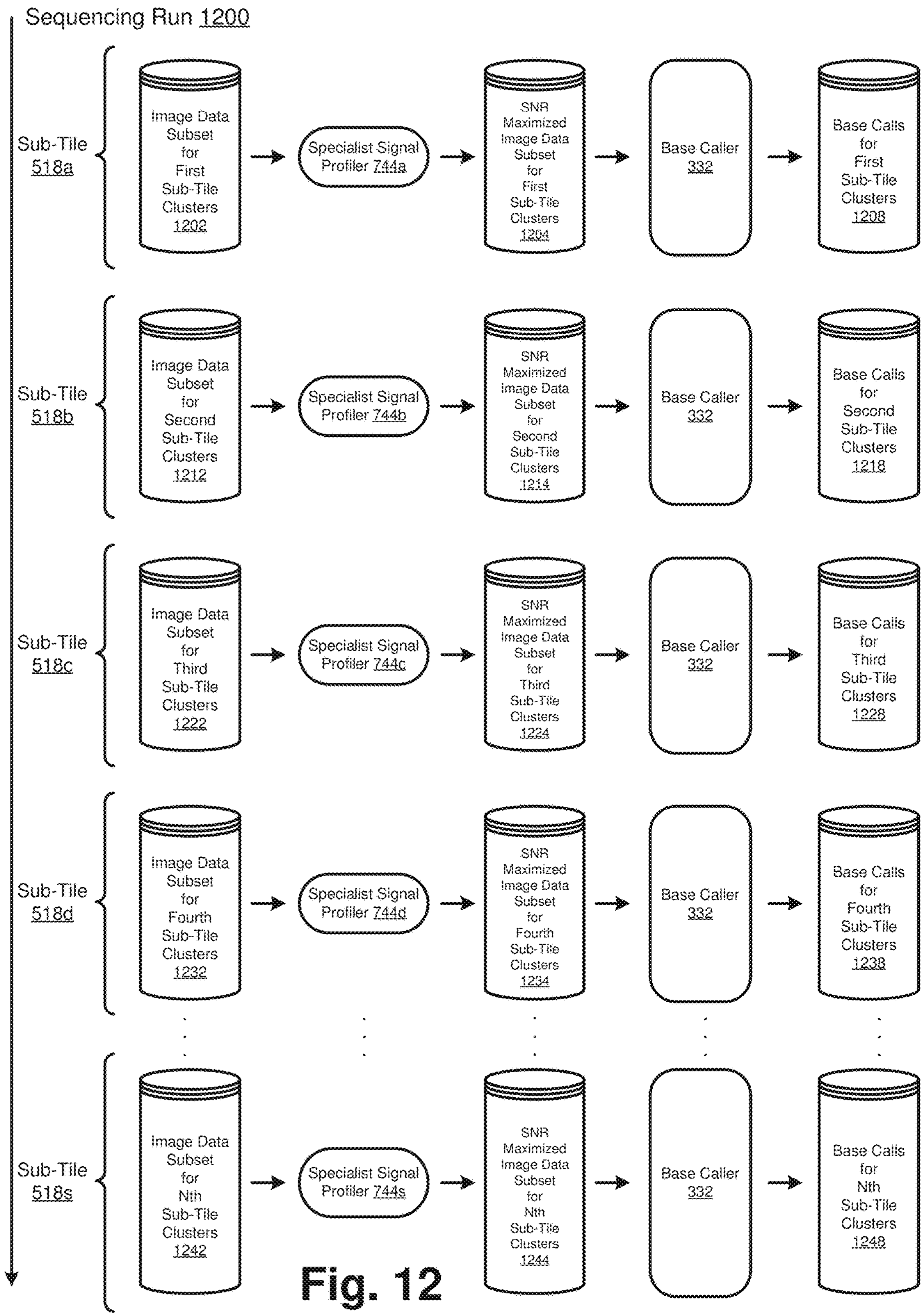
FIG. 12 shows one implementation of applying the trained sub-tile-specific specialist signal profilers to image data subsets corresponding to the respective cluster classes during a sequencing run.

FIG. 12 shows one implementation of applying the trained sub-tile-specific specialist signal profilers 744 to image data subsets 1202, 1212, 1222, 1232, . . . , 1242 corresponding to the respective cluster classes 742 during a sequencing run 1200. In one implementation, the flow cell 400 is imaged at the sub-tile-level. So, for the 518*a*, 518*b*, 518*c*, 518*d*, . . . , 518*s*, a first image data subset 1202 includes a first sub-tile image patch of the first sub-tile 518*a*, a second image data subset 1212 includes a second sub-tile image patch of the second sub-tile 518*b*, a third image data subset 1222 includes a third sub-tile image patch of the third sub-tile 518*c*, a fourth image data subset 1232 includes a fourth sub-tile image patch of the fourth sub-tile 518*d*, and so on (continuing to the $s^{th}$ image data subset 1242 comprising the $s^{th}$ sub-tile image patch of the $s^{th}$ sub-tile 518*s*).

The first specialist signal profiler 744*a* is configured to maximize the signal-to-noise ratio of intensity data in the first image data subset 1202 to generate a signal-to-noise ratio maximized version 1204 of the first image data subset 1202. The second specialist signal profiler 744*b* is configured to maximize the signal-to-noise ratio of intensity data in the second image data subset 1212 to generate a signal-to-noise ratio maximized version 1214 of the second image data subset 1212. The third specialist signal profiler 744*c* is configured to maximize the signal-to-noise ratio of intensity data in the third image data subset 1222 to generate a signal-to-noise ratio maximized version 1224 of the third image data subset 1222. The fourth specialist signal profiler 744*d* is configured to maximize the signal-to-noise ratio of intensity data in the fourth image data subset 1232 to generate a signal-to-noise ratio maximized version 1234 of the fourth image data subset 1232, and so on (continuing to signal-to-noise ratio maximized version 1244 of the $s^{th}$ image data subset 1242). The base caller 332 processes the signal-to-noise ratio maximized versions 1204, 1214, 1224, 1234, . . . , 1244 and generates base calls 1208, 1218, 1228, 1238, . . . , 1248.

Temporal Configuration-Specific Specialist Signal Profilers

Figure 13:
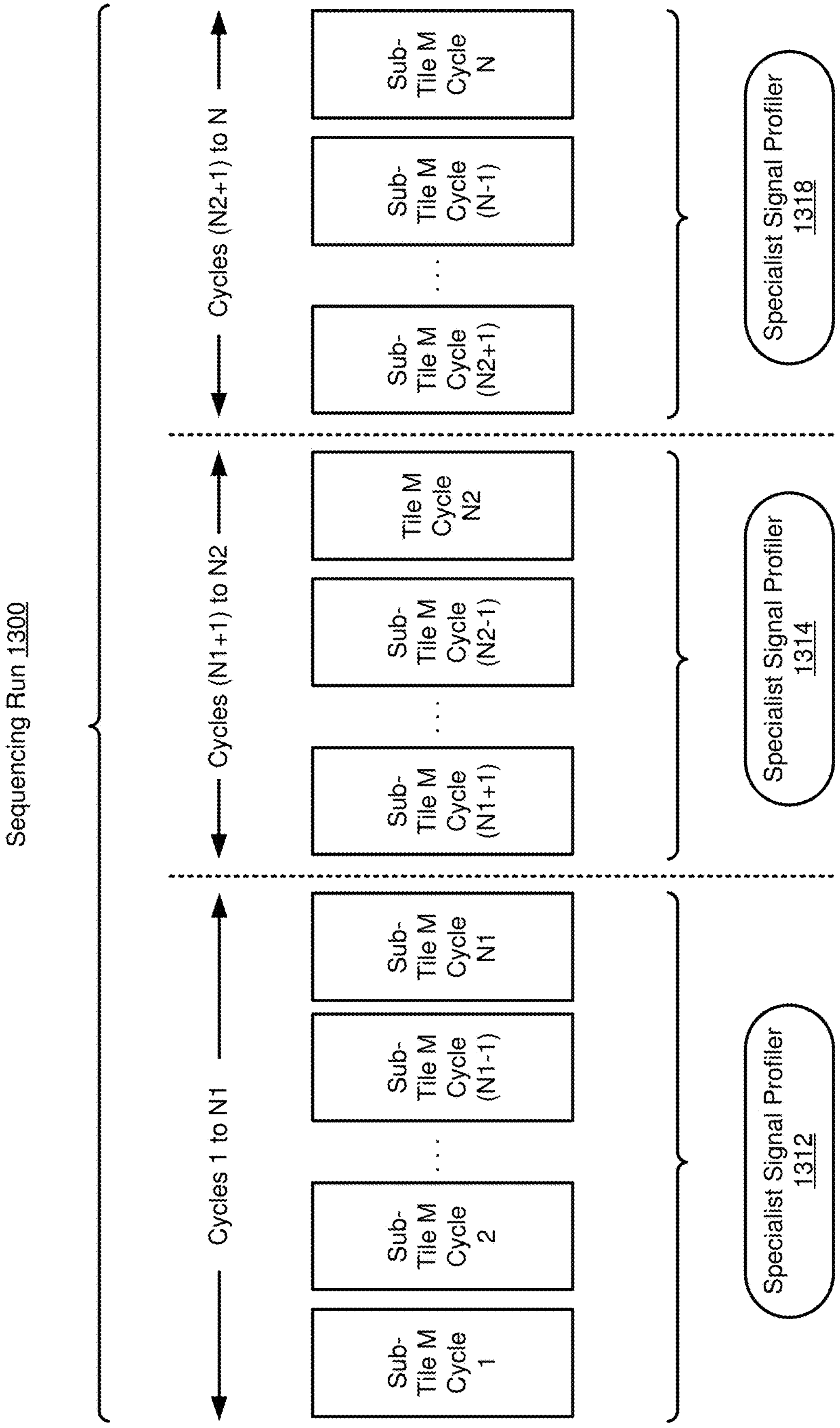
FIG. 13 shows one implementation of respective/separate/different/independent specialist signal profilers for respective sub-series of sequencing cycles of a sequencing run with a total of N sequencing cycles.

FIG. 13 shows one implementation of respective/separate/different/independent specialist signal profilers for respective sub-series of sequencing cycles of a sequencing run 1300 with a total of N sequencing cycles. The first specialist signal profiler 1312 is configured to maximize the signal-to-noise ratio of intensity data of clusters located on sub-tile M and generated during sequencing cycles 1 to N1. The second specialist signal profiler 1314 is configured to maximize the signal-to-noise ratio of intensity data of the clusters located on the sub-tile M and generated during sequencing cycles N1+1 to N2. The third specialist signal profiler 1318 is configured to maximize the signal-to-noise ratio of intensity data of the clusters located on the sub-tile M and generated during sequencing cycles N2+1 to N. Other examples of the temporal configurations include a first read's sequencing cycles (read 1) of a sequencing run, and a second read's sequencing cycles (read 2) of the sequencing run.

Figure 14:
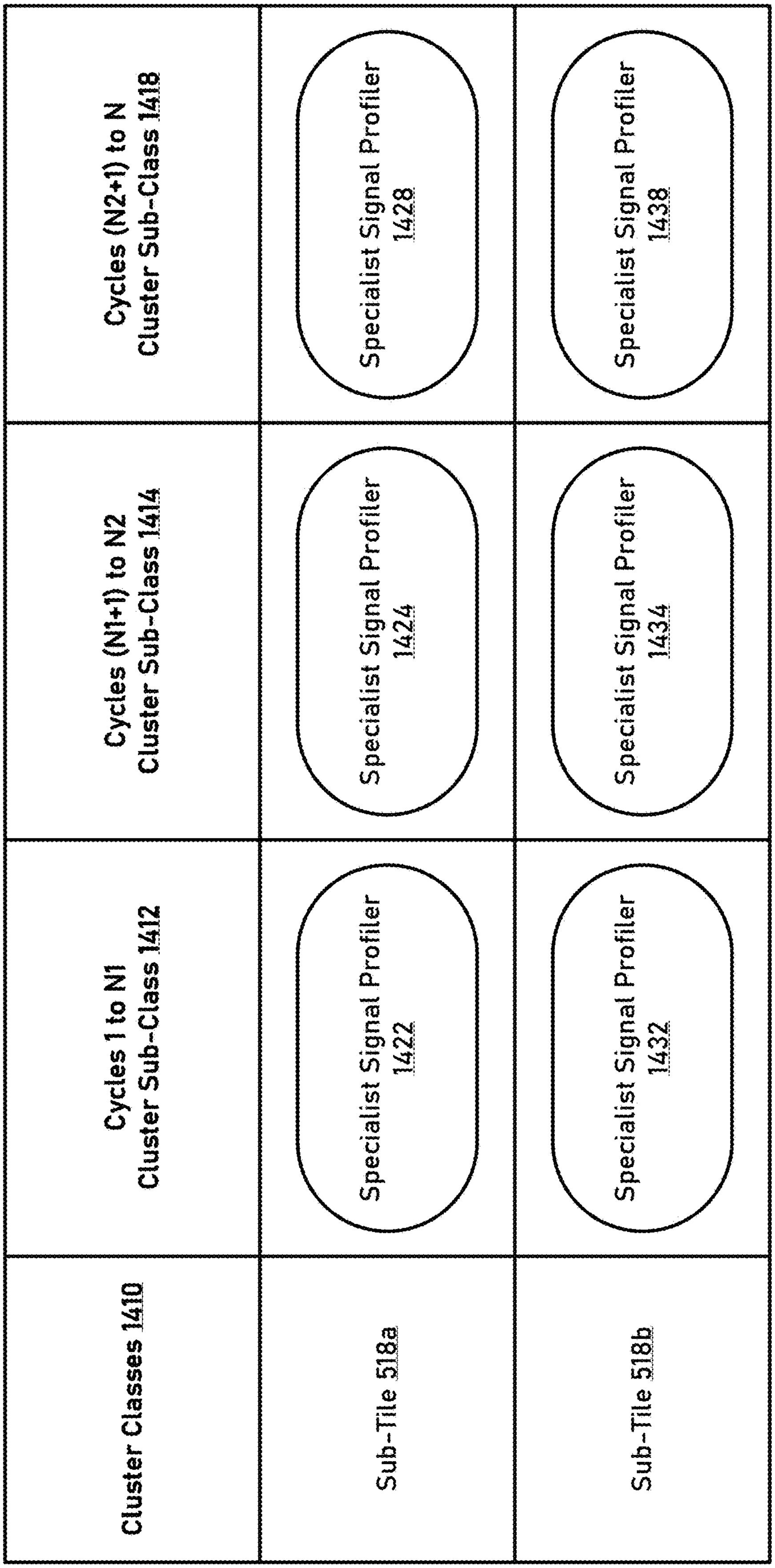
FIG. 14 shows one implementation of respective/separate/different/independent specialist signal profilers for a combination of different spatial configurations (e.g., different sub-tiles) and different temporal configurations (e.g., different sub-series of sequencing cycles).

FIG. 14 shows one implementation of respective/separate/different/independent specialist signal profilers for a combination of different spatial configurations (e.g., different sub-tiles) and different temporal configurations (e.g., different sub-series of sequencing cycles). In one implementation, the cluster classes 1410 are defined by the different spatial configurations (e.g., different sub-tiles). In one implementation, the cluster sub-classes 1412, 1414, and 1418 are defined by different temporal configurations (e.g., different sub-series of sequencing cycles).

The first specialist signal profiler 1422 is configured to maximize the signal-to-noise ratio of intensity data of the clusters located on the sub-tile 518*a* and generated during the sequencing cycles 1 to N1. The second specialist signal profiler 1424 is configured to maximize the signal-to-noise ratio of intensity data of the clusters located on the sub-tile

518*a* and generated during the sequencing cycles N1+1 to N2. The third specialist signal profiler 1428 is configured to maximize the signal-to-noise ratio of intensity data of the clusters located on the sub-tile 518*a* and generated during the sequencing cycles N2+1 to N.

The fourth specialist signal profiler 1432 is configured to maximize the signal-to-noise ratio of intensity data of the clusters located on the sub-tile 518*b* and generated during the sequencing cycles 1 to N1. The fifth specialist signal profiler 1434 is configured to maximize the signal-to-noise ratio of intensity data of the clusters located on the sub-tile 518*b* and generated during the sequencing cycles N1+1 to N2. The sixth specialist signal profiler 1438 is configured to maximize the signal-to-noise ratio of intensity data of the clusters located on the sub-tile 518*b* and generated during the sequencing cycles N2+1 to N.

Cluster/Well-Specific Specialist Signal Profilers

Figure 15:
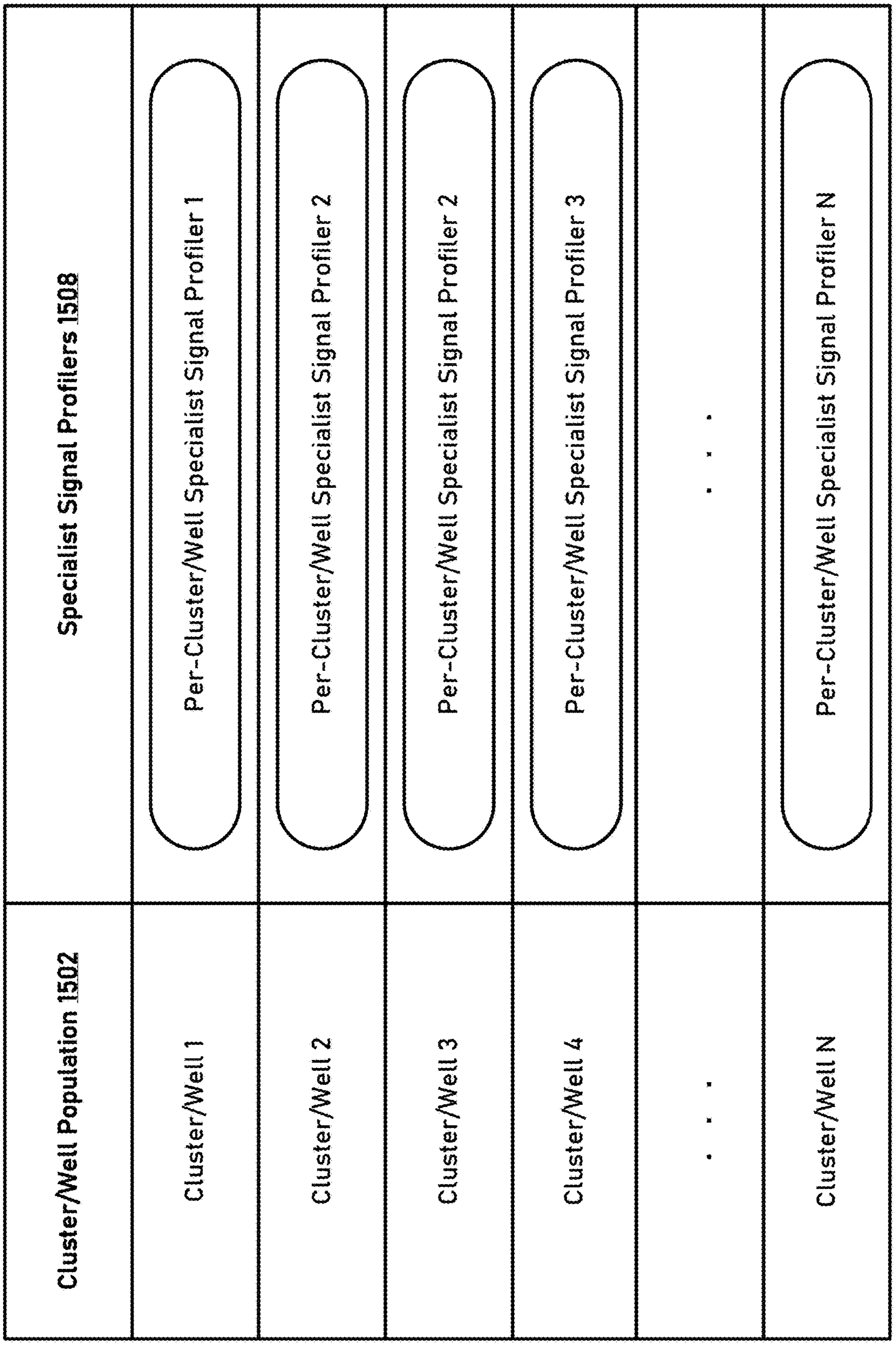
FIG. 15 shows one implementation of respective/separate/different/independent specialist signal profilers for each cluster/well sequenced during a sequencing run.

FIG. 15 shows one implementation of respective/separate/different/independent specialist signal profilers for each cluster/well sequenced during a sequencing run. The clusters/wells on a flow cell can be pre-identified by their location coordinates. These location coordinates of the clusters/wells can be used to train per-cluster/well specialist signal profilers during training on training per-cluster/well intensity data, and to apply the trained per-cluster specialist signal profilers during inference on inference per-cluster/well intensity data based on the location coordinates of the clusters/wells. In FIG. 15, the cluster/well population 1502 has N clusters/wells, and therefore the specialist signal profilers 1508 comprise respective N per-cluster/well specialist signal profilers. In other implementations, different per-cluster/well signal profilers can be trained for different temporal configurations as well, as discussed above.

Offline Training

Figure 16:
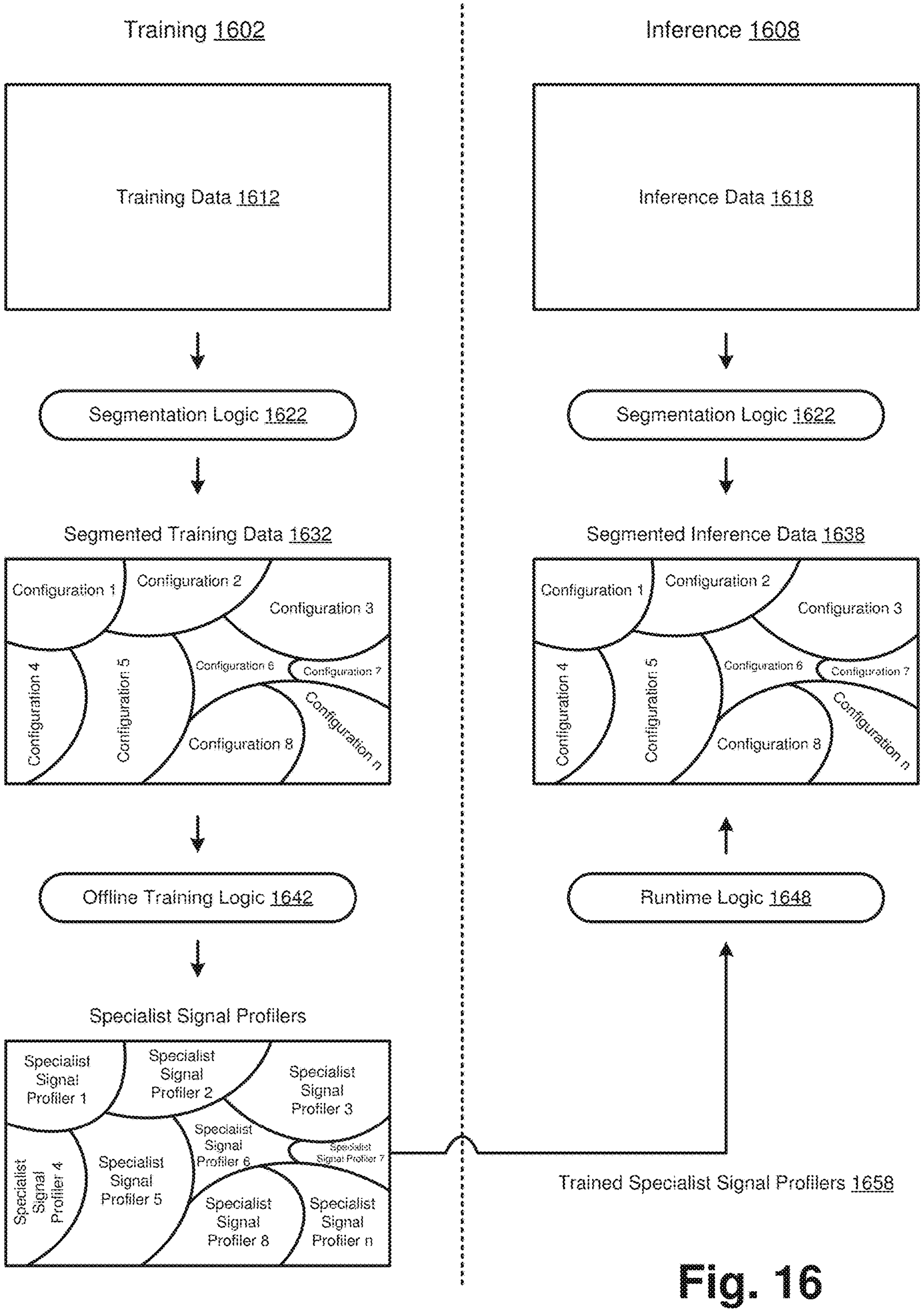
FIG. 16 shows one implementation of offline training of specialist signal profilers on sequenced data from one or more completed/already-executed sequencing runs, and application of the trained specialist signal profilers on sequenced data from an ongoing sequencing run.

FIG. 16 shows one implementation of offline training of specialist signal profilers on sequenced data from one or more completed/already-executed sequencing runs, and application of the trained specialist signal profilers on sequenced data from an ongoing sequencing run. Training data 1612 is generated during a training stage 1602. The training data 1612 includes the sequenced data from the one or more completed/already-executed sequencing runs.

Figure 17:
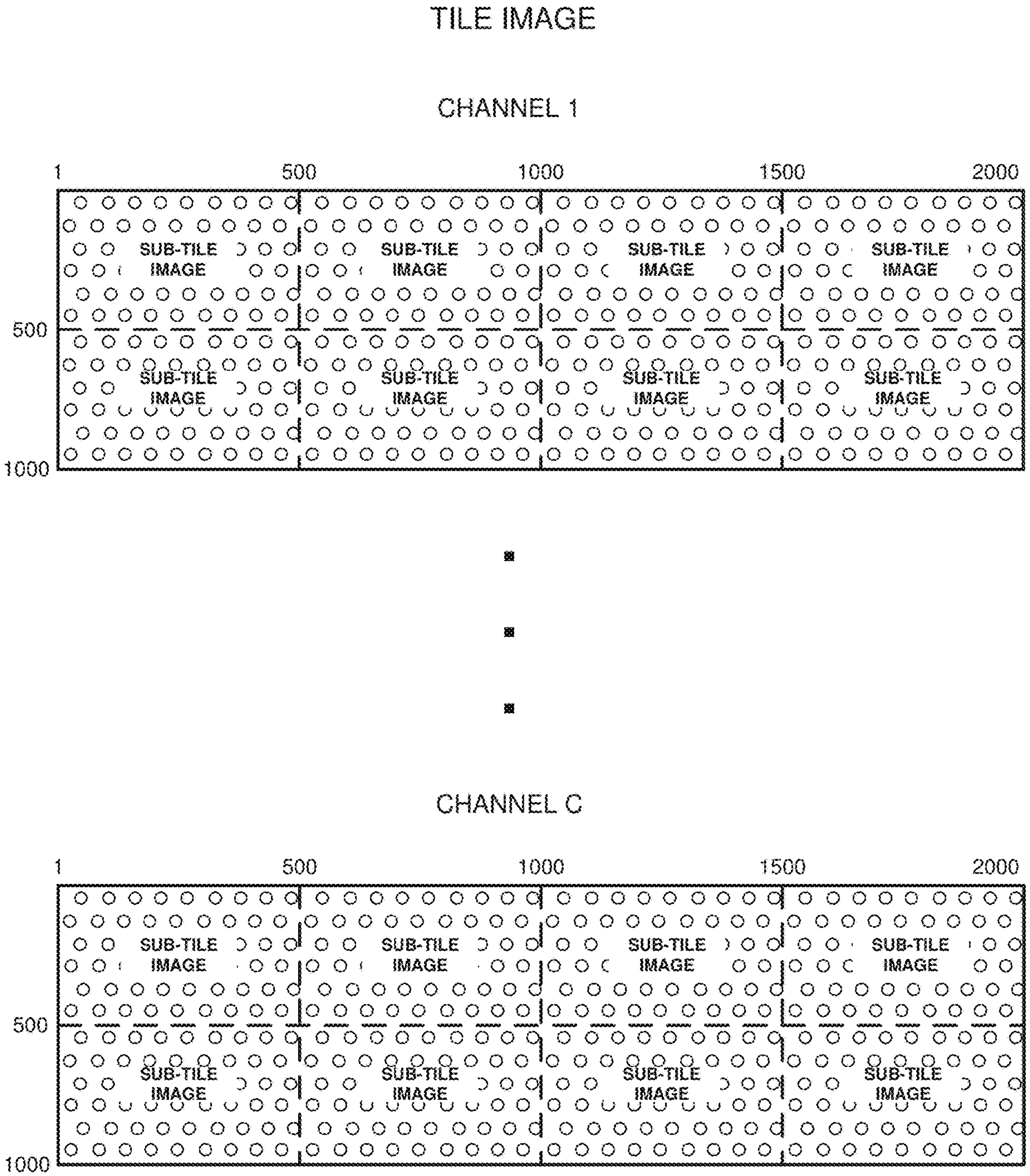
FIG. 17 shows an example tile image partitioned into sub-tiles images.

Segmentation logic 1622 segments the training data 1612 based on one or more configurations selected from different spatial configurations, temporal configurations, signal distribution configurations, or any combination thereof. What results is segmented training data 1632 with configuration-specific training data subsets 1 to N. For example, the training data 1612 can include K images of a tile from K imaging cycles of a completed/already-executed sequencing run, with each tile image having multiple color channels. FIG. 17 shows an example of a tile image with C color channels. In this case, the segmentation logic 1622 logically partitions each tile image in the training data 1612 into sub-tile images by specifying pixel ranges. For example, a first sub-tile image of a tile can range from pixels 1 to 500, a second sub-tile image of the tile can range from pixels 501 to 1000, and so on. The pixel ranges can be defined using fiducial markers, as discussed above.

Offline training logic 1642 trains respective/separate/different/independent specialist signal profilers 1 to N on the respective configuration-specific training data subsets 1 to N. What results is trained specialist signal profilers 1 to N. Returning to the example in FIG. 17, a corresponding specialist signal profiler is trained to maximize the signal-to-noise ratio of each sub-tile image in the training data 1612.

Inference data 1618 is generated during an inference stage 1608. The inference data 1618 includes the sequenced data from the ongoing sequencing run (e.g., the first i cycles of the ongoing sequencing run).

The segmentation logic 1622 segments the inference data 1618 based on the same one or more configurations that were used to segment the training data 1612 during the training stage 1602. What results is segmented inference data 1638 with configuration-specific inference data subsets 1 to N. For example, the inference data 1618 can include K images of a tile from K imaging cycles of the ongoing sequencing run, with each tile image having multiple color channels. Returning to the example in FIG. 17, the segmentation logic 1622 logically partitions each tile image in the inference data 1618 into sub-tile images by specifying the same pixel ranges used to partition the training data 1612.

Runtime logic 1648 applies the respective trained specialist signal profilers 1 to N 1658 on the respective configuration-specific inference data subsets 1 to N. Returning to the example in FIG. 17, a corresponding trained specialist signal profiler is applied to maximize the signal-to-noise ratio of each sub-tile image in the segmented inference data 1638.

Online Training

Figure 18:
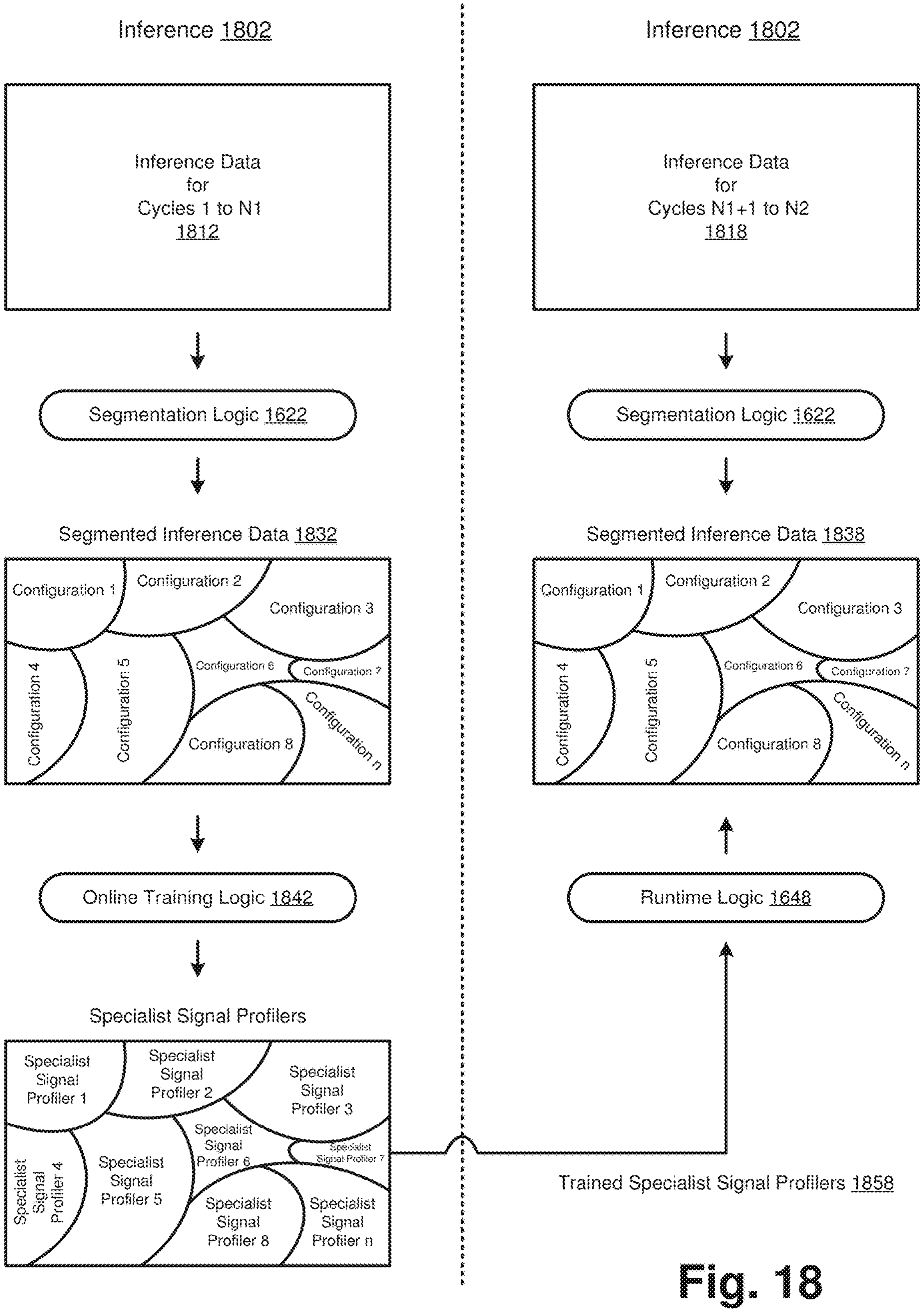
FIG. 18 shows one implementation of online training of specialist signal profilers on sequenced data from earlier sequencing cycles of an ongoing sequencing run, and application of the trained specialist signal profilers on sequenced data from later sequencing cycles of the ongoing sequencing run.

FIG. 18 shows one implementation of online training of specialist signal profilers on sequenced data from earlier sequencing cycles of an ongoing sequencing run, and application of the trained specialist signal profilers on sequenced data from later sequencing cycles of the ongoing sequencing run. Inference data 1802 is generated during an inference stage 1802. The inference data 1812 includes the sequenced data from the earlier sequencing cycles (e.g., cycles 1 to N1) of the ongoing sequencing run.

Segmentation logic 1622 segments the inference data 1812 based on one or more configurations selected from different spatial configurations, temporal configurations, signal distribution configurations, or any combination thereof. What results is segmented inference data 1832 with configuration-specific training data subsets 1 to N. For example, the inference data 1812 can include N1 images of a tile from the N1 earlier sequencing cycles of the ongoing sequencing run, with each tile image having multiple color channels. FIG. 17 shows an example of a tile image with C color channels. In this case, the segmentation logic 1622 logically partitions each tile image in the inference data 1812 into sub-tile images by specifying pixel ranges. For example, a first sub-tile image of a tile can range from pixels 1 to 500, a second sub-tile image of the tile can range from pixels 501 to 1000, and so on. The pixel ranges can be defined using fiducial markers, as discussed above.

Offline training logic 1842 trains respective/separate/different/independent specialist signal profilers 1 to N on the respective configuration-specific training data subsets 1 to N. What results is trained specialist signal profilers 1 to N. Returning to the example in FIG. 17, a corresponding specialist signal profiler is trained to maximize the signal-to-noise ratio of each sub-tile image in the inference data 1812.

Inference data 1818 is also generated during the inference stage 1802. The inference data 1818 includes the sequenced data from the later sequencing cycles (e.g., cycles N1+1 to N2) of the ongoing sequencing run.

The segmentation logic 1622 segments the inference data 1818 based on the same one or more configurations that were used to segment the inference data 1812 during the earlier sequencing cycles (e.g., cycles 1 to N1) of the ongoing sequencing run. What results is segmented inference data 1838 with configuration-specific inference data subsets 1 to N. For example, the inference data 1818 can include N2 images of a tile from the N2 later sequencing cycles of the ongoing sequencing run, with each tile image having multiple color channels. Returning to the example in FIG. 17, the segmentation logic 1622 logically partitions each tile image in the inference data 1818 into sub-tile images by specifying the same pixel ranges used to partition the inference data 1812.

Runtime logic 1648 applies the respective trained specialist signal profilers 1 to N 1858 on the respective configuration-specific inference data subsets 1 to N. Returning to the example in FIG. 17, a corresponding trained specialist signal profiler is applied to maximize the signal-to-noise ratio of each sub-tile image in the segmented inference data 1838.

In some implementations, the training process is iteratively repeated where the respective trained specialist signal profilers 1 to N 1858 are retrained/further trained on the segmented inference data 1838 from the later sequencing cycles (e.g., cycles N1+1 to N2) of the ongoing sequencing run, and applied on segmented inference data from even later sequencing cycles (e.g., cycles N2+1 to N3) of the ongoing sequencing run.

A control logic (not shown) can iterate, at each successive sequencing cycle of the ongoing sequencing run, or at successive subseries of sequencing cycles of the ongoing sequencing run (e.g., every ten or twenty sequencing cycles) (i) the segmentation of a current batch of image data based on one or more configurations selected from different spatial configurations, temporal configurations, signal distribution configurations, or any combination thereof, (ii) the retraining of the respective trained specialist signal profilers 1 to N on the segmented current batch of image data, (iii) segmentation of a next batch of image data on the same basis as the current batch of image data, and (iv) the application of the respective retrained specialist signal profilers 1 to N to the segmented next batch of image data.

Signal Distribution Configuration-Specific Specialist Signal Profilers

FIG. 19 shows one implementation of training respective/separate/different/independent specialist signal profilers for respective signal distributions observed in sequenced data. In some implementations, the respective signal distributions can be observed in sequenced data from an offline/already-executed sequencing run. In other implementations, the respective signal distributions can be also observed in sequenced data from an online/ongoing sequencing run (e.g., observed in the first ten sequencing cycles of the ongoing sequencing run).

Figure 20:
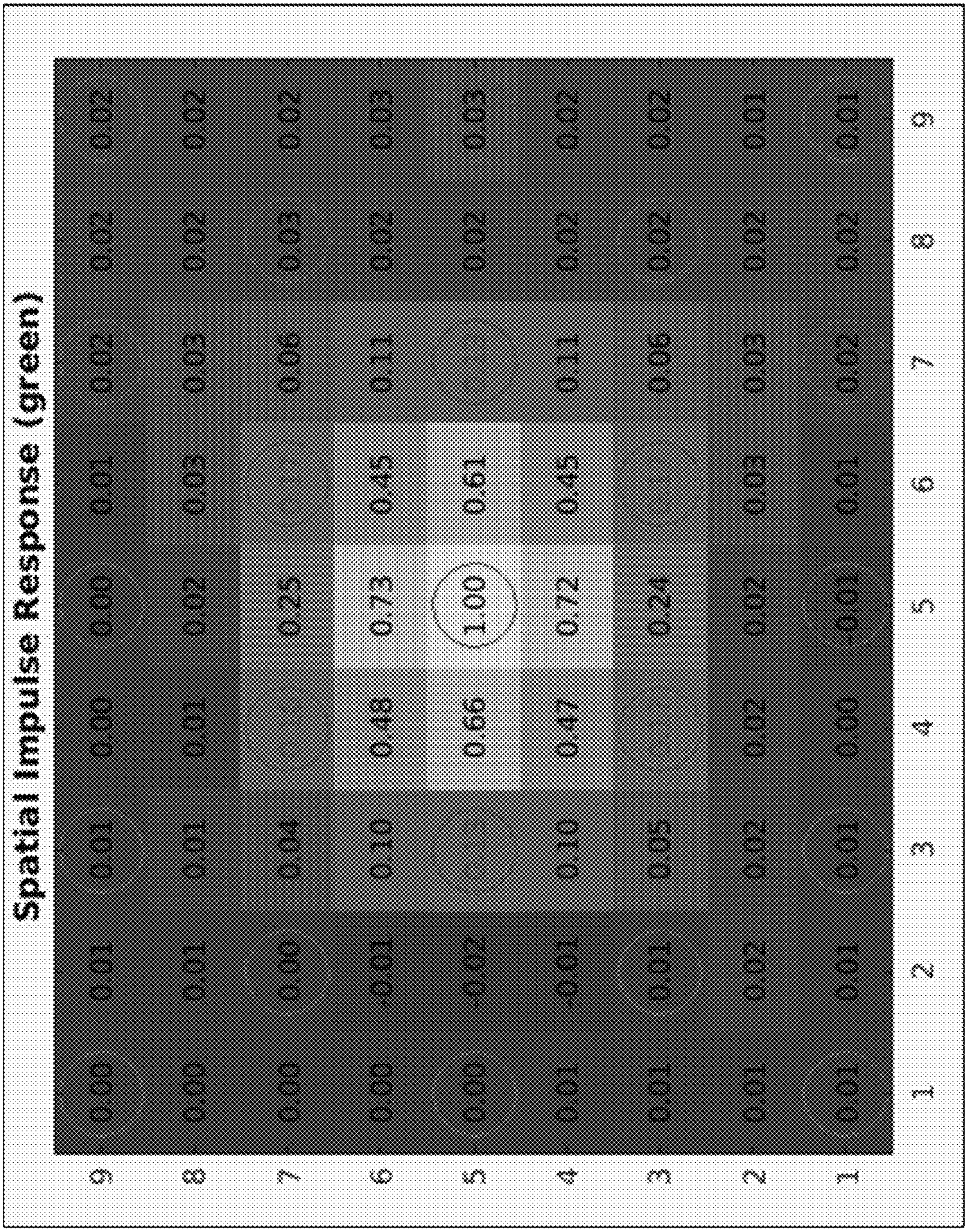
FIG. 20 shows one example of a signal distribution/signal profile/cluster intensity profile.

FIG. 20 shows one example of a signal distribution/signal profile/cluster intensity profile. The cluster intensity profile depicted in FIG. 20 follows an attenuation pattern in which the cluster signal is strongest at a cluster center and attenuates as it propagates away from the cluster center. Subpopulations/groups/sets of clusters 1904 in a cluster population can have similar signal distributions. Those clusters that share same or similar signal distributions can be bucketed together (e.g., by grouping/addressing clusters by their location coordinates), such that a specialist signal profiler can be trained for a corresponding cluster group/set exhibiting a corresponding signal distribution. Unlike spatial grouping where spatially contiguous clusters are grouped, signal distribution-based grouping can group non-contiguous clusters. For example, edge clusters on opposite edges of a tile can have similar signal distributions, and can be grouped in a what that their intensity data is corrected by a same specialist signal profiler (e.g., by grouping/addressing clusters by their location coordinates).

As used herein, the phrase "similar signal distribution" refers to those signal distributions that share substantially overlapping signal patterns. For example, two signal patters of similar shape (e.g., trapezoids) but of different shape sizes (e.g., one bigger trapezoid and one smaller trapezoid) can be considered to have similar signal distributions. Similarly, two signal patterns with a common centroid or centroids within a range of, for example, one to five units in each dimension, can be considered to have similar signal distributions.

In FIG. 19, respective/separate/different/independent specialist signal profilers 1 to N 1908 are trained to maximize the signal-to-noise ratio of respective signal distributions 1 to N 1902 corresponding to respective cluster sets 1 to N 1904. Of course, different signal distributions can be observed at different sequencing cycles, and therefore different specialist signal profilers can be trained for and configured for application at different temporal stages of an ongoing sequencing run.

As used herein, the phrase "different temporal stages of an ongoing sequencing run" refers to different sequencing cycles or different sequencing cycle groups of the ongoing sequencing run. For example, if the sequencing run has 150 sequencing cycles, then each successive sequencing cycle can be considered a different temporal stage, or groups of sequencing cycles like cycles 1-20, cycles 20-40, cycles 40-70, and so on can be considered different temporal stages.

Processing Pipeline

Figure 21:
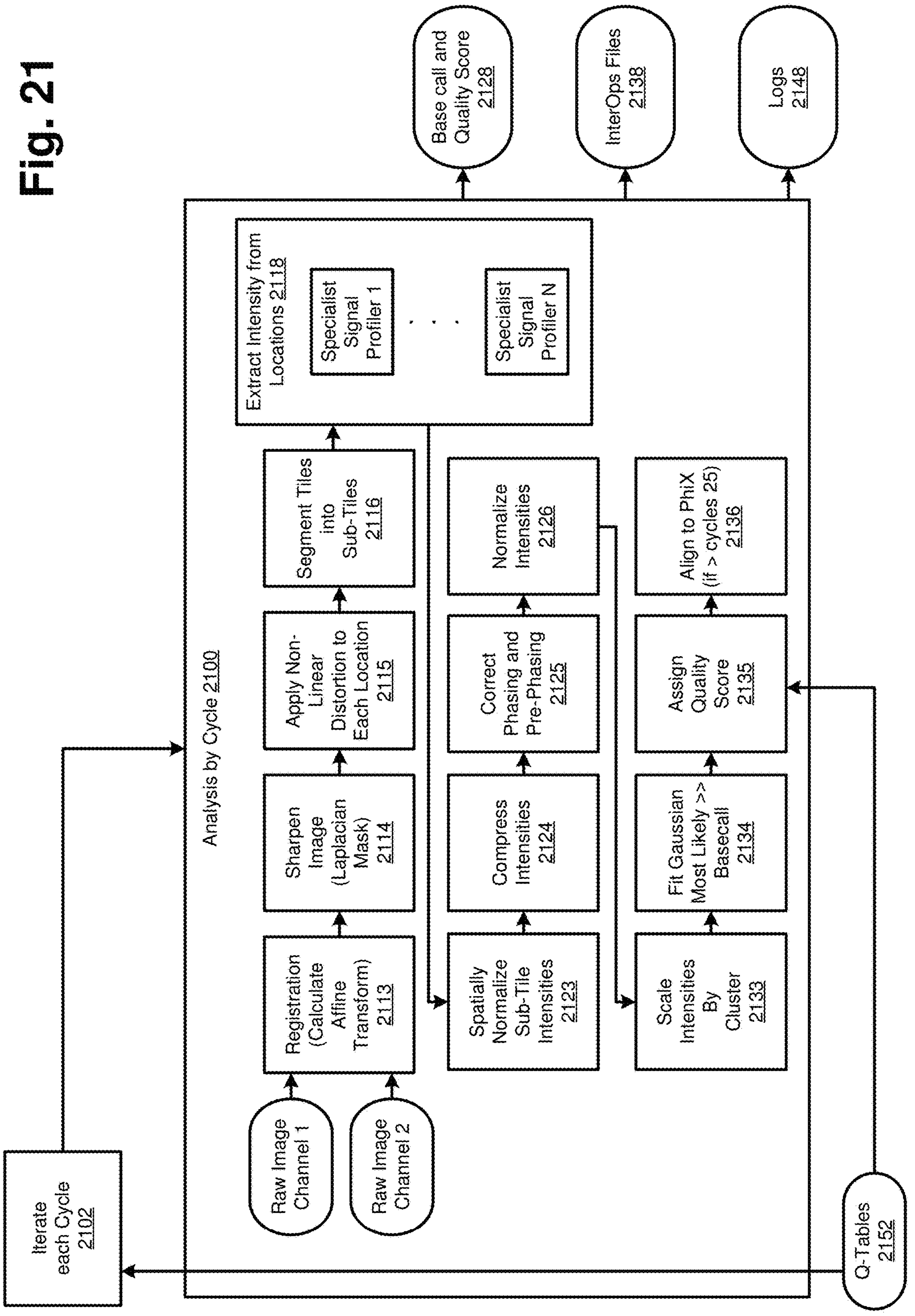
FIG. 21 shows one implementation of a processing pipeline that implements the technology disclosed.

FIG. 21 shows one implementation of a processing pipeline that implements the technology disclosed. The processing pipeline can be implemented by the real time analysis module 225. The processing pipeline is executed on a cycle-by-cycle basis 2100, and iterated 2102 for each new cycle, according to one implementation. In one implementation, the input to the processing pipeline is tile images having a first (green color) channel and a second (blue color) channel.

At operation 2113, a template image is produced that identifies locations of clusters on a tile using sequencing images from some number of initial sequencing cycles called template cycles. The template image is used as a reference for subsequent registration and intensity extraction steps. The template image is generated by detecting and merging bright spots in each sequencing image of the template cycles, which in turn involves sharpening a sequencing image 2114 (e.g., using the Laplacian convolution), determining an "on" threshold by a spatially segregated Otsu approach, and subsequent five-pixel local maximum detection with subpixel location interpolation. The phrase "on threshold" can refer to an intensity value that exceeds a preset value, for example, 200 or 320, such that the intensity value is detected to be more than a background intensity value or a noise intensity value.

The processing pipeline then registers a current sequencing image against the template image. This is achieved by using image correlation to align the current sequencing image to the template image on a sub-region, or by using non-linear transformations (e.g., a full six-parameter linear affine transformation).

At operation 2115, the processing pipeline applies a non-linear distortion to each spot to account for, for example, optical distortions caused by the geometry of the optical lens. The non-linear distortion can be applied as channel-dependent coefficients of third order polynomials.

At operation 2116, the processing pipeline segments the tile images into sub-tile images based on one or more configurations selected from different spatial configurations, temporal configurations, signal distribution configurations, or any combination thereof.

At operation 2118, intensity is extracted from the segmented sub-tile images using the corresponding specialist signal profilers 1 to N.

At operation 2123, the sub-tile intensities are spatially normalized, for example, by making the $90^{th}$ percentiles of their extracted intensities are equal.

At operation 2124, the sub-tile intensities are compressed.

At operation 2125, the processing pipeline applies empirical phasing correction to compensate noise in the image data caused by phasing and pre-phasing errors.

At operation 2126, the processing pipeline spatially normalizes the extracted signal intensities to account for variation in illumination across the sampled imaged. For example, intensity values can be normalized such that a 5th and 95th percentiles have values of 0 and 1, respectively. The normalized signal intensities for the image (e.g., normalized intensities for each channel) can be used to calculate mean chastity for the plurality of spots in the image.

At operation 2133, the processing pipeline scale the intensities on a cluster-by-cluster basis to account for variation in brightness of clusters.

At operation 2134, the processing pipeline uses the expectation maximization (EM) algorithm to produce base calls, as discussed above.

At operation 2135, the processing pipeline assigns quality scores to the called bases using quality tables (Q-Tables) 2152.

At operation 2136, the processing pipeline aligns the called bases to a reference genome (e.g., of the PhiX bacteria) to compute a mismatch rate.

The processing pipeline generates certain outputs, such as base call and quality score 2128, inter-operation (InterOp) files 2138 (binary reporting files for sequencing analysis view), and logs 2148 (e.g., error logs, general event logs, processing event logs, warning event logs).

Other Configurations

Other examples of configurations covered by this disclosure include segmenting sequencing data and training corresponding specialist signal profilers by library type, sample type, indexing type (first index read v/s second index read), read type (forward read v/s reverse read), physical properties of the sample, noise type (e.g., bubble), and reagent type.

Figure 33:
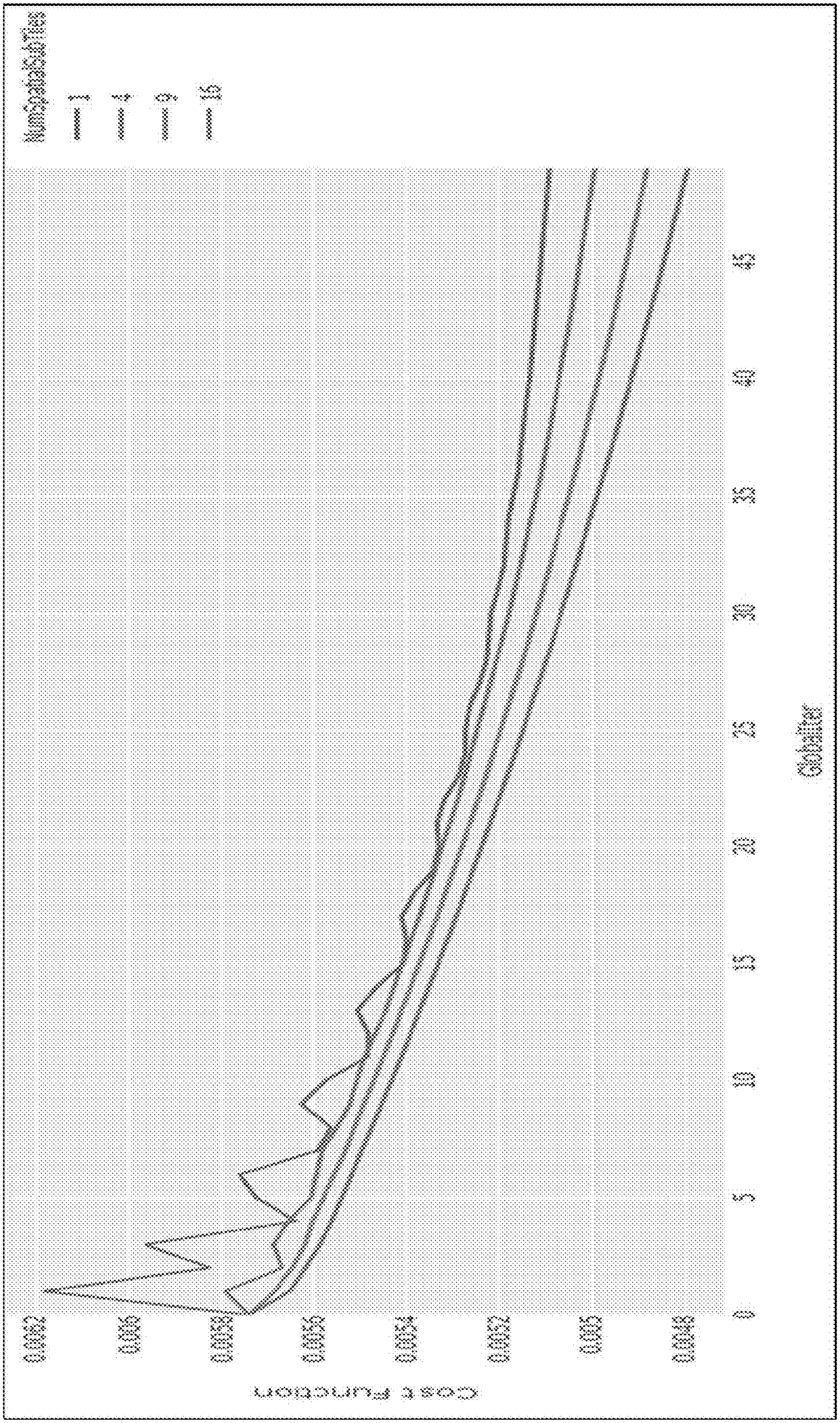
FIG. 33 shows how a cost function for a specialist signal profiler improves with each iteration of gradient descent.

Performance Results—Technical Effects and Advantages as Objective Indicia of Non-Obviousness and Inventiveness FIG. 33 shows how a cost function for a specialist signal profiler improves with each iteration of gradient descent. A cost function (or loss function) measures the performance of a model on a given data. In FIG. 33, the different colored lines correspond to a number of sub-tiles into which a tile is partitioned, such that for each sub-tile, the specialist signal profiler is adapted/trained/configured/updated independently. As the number of sub-tiles increases from 1 to 16 (4×4 sub-tiles), the number of fitting parameters in the specialist signal profiler also increases. As a result, the cost function is lower. The cost function is the sum of square of Euclidean distance between well intensity and base call centroid for a sample of wells (clusters). Improving this cost function improves base calling accuracy as well.

Figure 34:
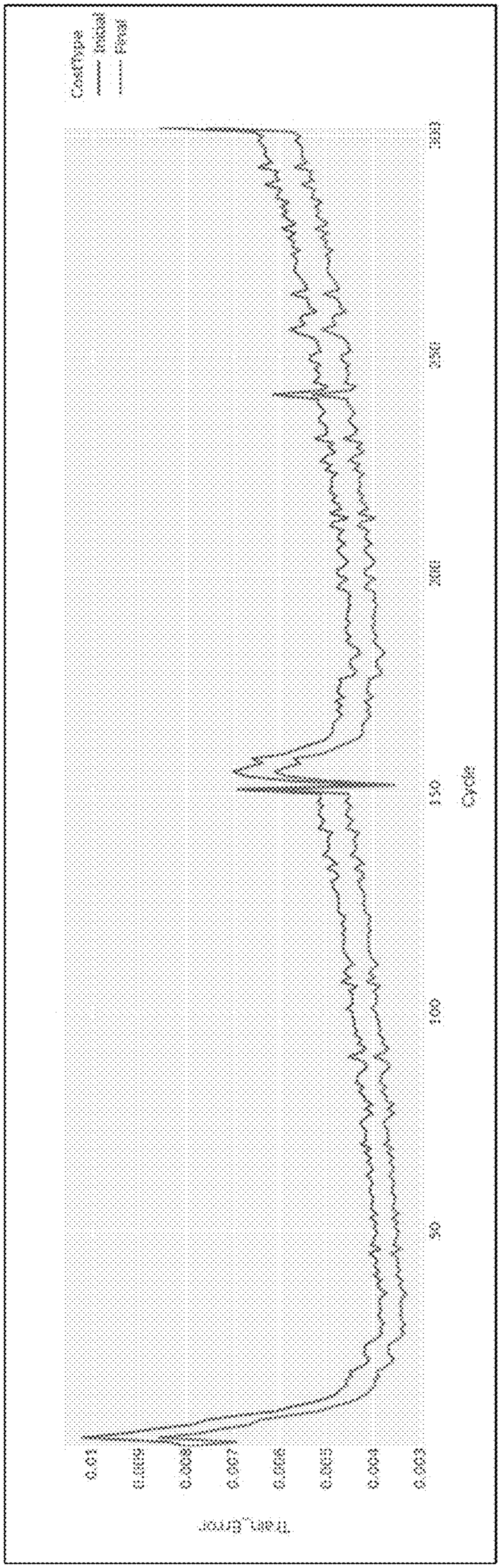
FIG. 34 is a plot that shows initial and final values of the cost function of FIG. 33 when the specialist signal profiler is adapted/trained/configured/updated at each sequencing cycle.

FIG. 34 is a plot that shows initial and final values of the cost function of FIG. 33 when the specialist signal profiler is adapted/trained/configured/updated at each sequencing cycle. At each successive sequencing cycle, we started with a same initial specialist signal profiler and adapted the specialist signal profiler using gradient descent. The plot shows that it is possible to adapt/train/configure/update the specialist signal profiler at any sequencing cycle.

Figures 35A, 35B:
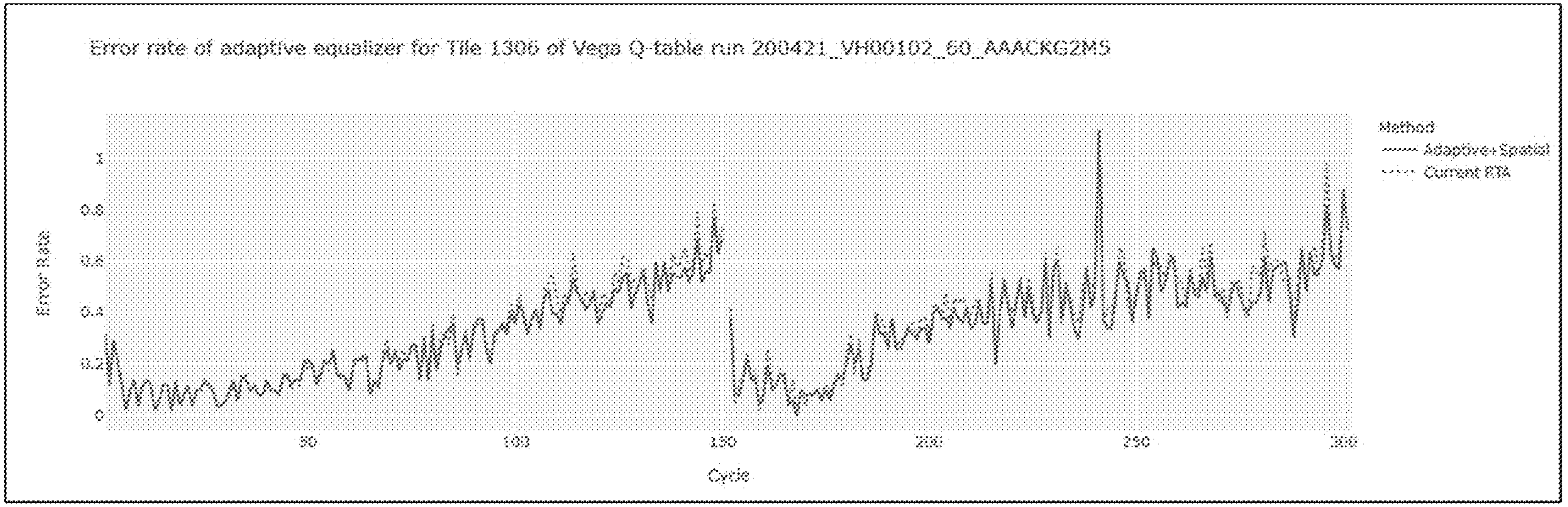
FIGS. 35A and 35B show the improvement in primary analysis metrics for a sequencing run when we adapt/train/configure/update the specialist signal profiler.

FIGS. 35A and 35B show the improvement in primary analysis metrics for a sequencing run when we adapt/train/configure/update the specialist signal profiler. In this case, mean PhiX error rate improved from 0.3520% to 0.3316%.

Figures 36A, 36B:
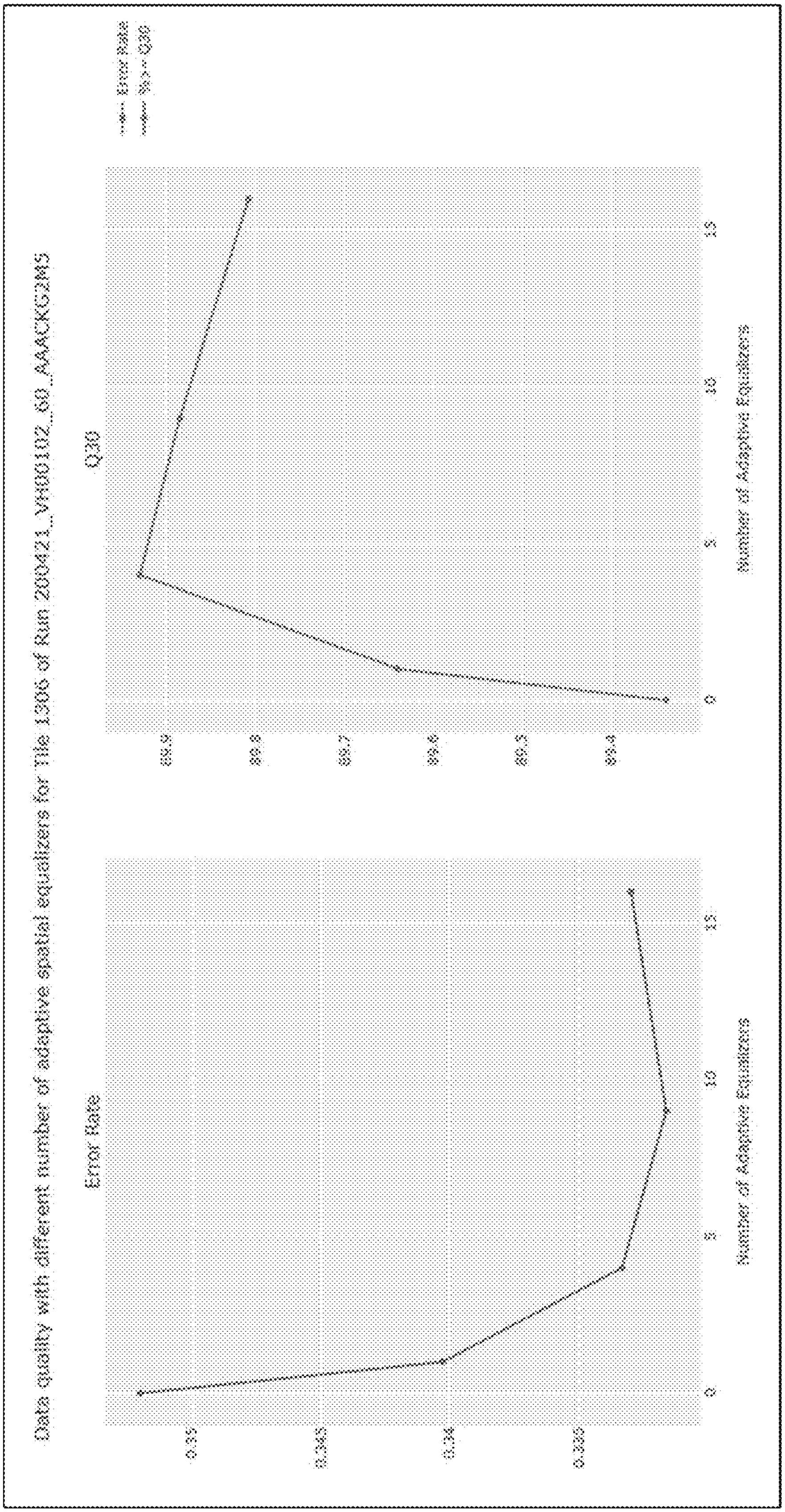
FIGS. 36A and 36B show two plots that assess a number of sub-tiles into which a sequencing tile can be partitioned for adaptive equalization of respective specialist signal profilers.

FIGS. 36A and 36B show two plots that assess a number of sub-tiles into which a sequencing tile can be partitioned for adaptive equalization of respective specialist signal profilers. For each sub-tile, a separate specialist signal profiler is adapted/trained/configured/updated using wells from a corresponding sub-tile. Using more sub-tiles allows us to model spatially varying phenomena within a tile more accurately which is why the error rate and Q30 improve significantly as we increase the number of sub-tiles from 1 to 9. However, the number of wells available to adapt the model decreases as the sub-tile gets smaller. That is why there is a tradeoff in picking the right number of sub-tiles. In this particular case, increasing the number of sub-tiles from 9 to 16 degrades error rate and Q30 slightly.

Computer System

Figure 37:
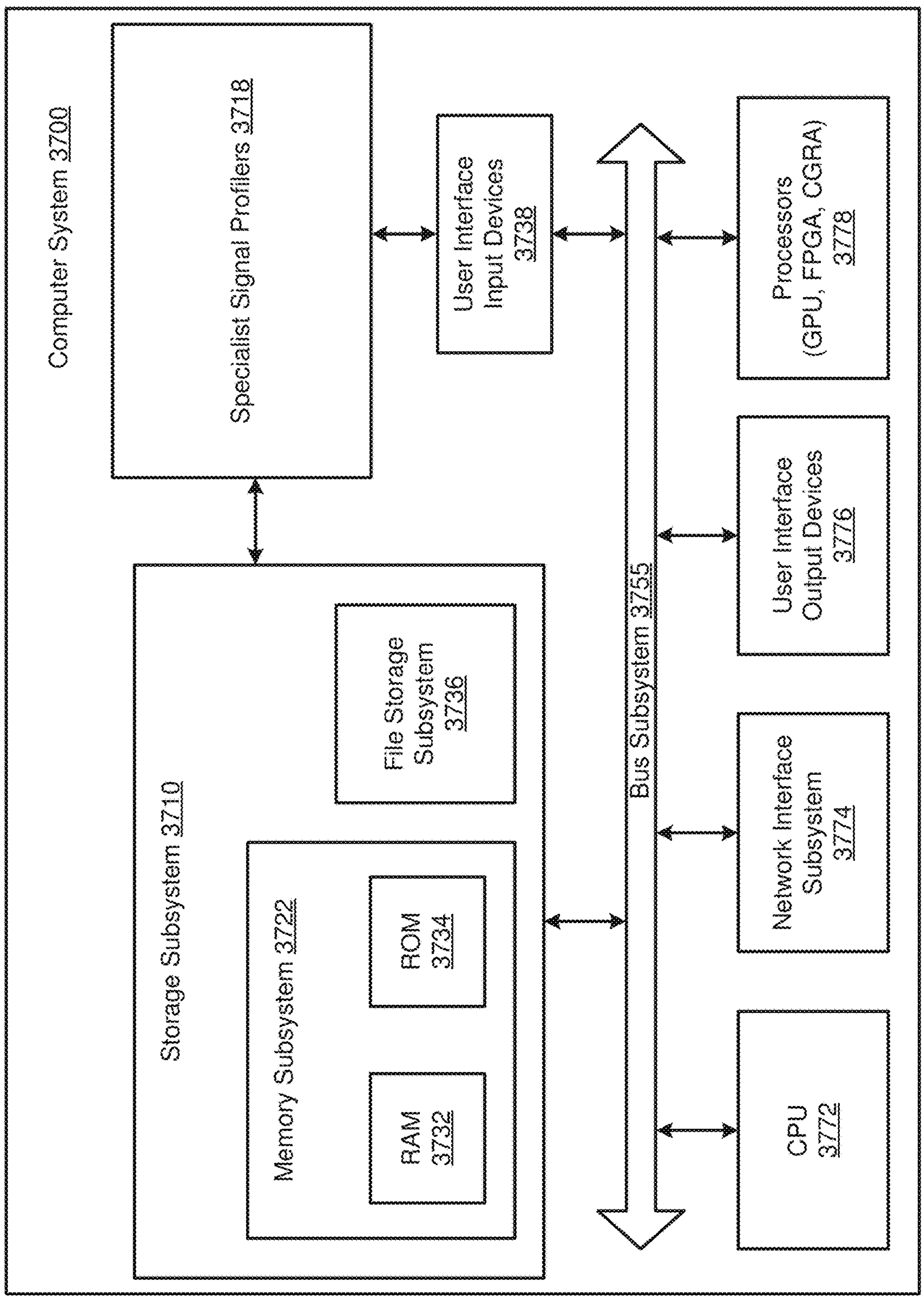
FIG. 37 shows an example computer system that can be used to implement the technology disclosed.

FIG. 37 shows an example computer system 3700 that can be used to implement the technology disclosed. Computer system 3700 includes at least one central processing unit (CPU) 3772 that communicates with a number of peripheral devices via bus subsystem 3755. These peripheral devices can include a storage subsystem 3710 including, for example, memory devices and a file storage subsystem 3736, user interface input devices 3738, user interface output devices 3776, and a network interface subsystem 3774. The input and output devices allow user interaction with computer system 3700. Network interface subsystem 3774 provides an interface to outside networks, including an interface to corresponding interface devices in other computer systems.

In one implementation, specialist signal profilers 3718 are communicably linked to the storage subsystem 3710 and the user interface input devices 3738.

User interface input devices 3738 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 3700.

User interface output devices 3776 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 3700 to the user or to another machine or computer system.

Storage subsystem 3710 stores programming and data constructs that provide the functionality of some or all of the modules and methods described herein. These software modules are generally executed by processors 3778.

Processors 3778 can be graphics processing units (GPUs), field-programmable gate arrays (FPGAs), application-specific integrated circuits (ASICs), and/or coarse-grained reconfigurable architectures (CGRAs). Processors 3778 can be hosted by a deep learning cloud platform such as Google Cloud Platform™, Xilinx™, and Cirrascale™. Examples of processors 3778 include Google's Tensor Processing Unit (TPU)™, rackmount solutions like GX4 Rackmount Series™, GX37 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 3722 used in the storage subsystem 3710 can include a number of memories including a main random access memory (RAM) 3732 for storage of instructions and data during program execution and a read only memory (ROM) 3734 in which fixed instructions are stored. A file storage subsystem 3736 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 3736 in the storage subsystem 3710, or in other machines accessible by the processor.

Bus subsystem 3755 provides a mechanism for letting the various components and subsystems of computer system 3700 communicate with each other as intended. Although bus subsystem 3755 is shown schematically as a single bus, alternative implementations of the bus subsystem can use multiple busses.

Computer system 3700 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 3700 depicted in FIG. 37 is intended only as a specific example for purposes of illustrating the preferred implementations of the present invention. Many other configurations of computer system 3700 are possible having more or less components than the computer system depicted in FIG. 37.

Neural Network-Based Base Caller

The following discussion focuses on a neural network-based base caller described herein that can be used in conjunction with the specialist signal profilers. First, the input to the neural network-based base caller is described, in accordance with one implementation. Then, examples of the structure and form of the neural network-based base caller are provided. Finally, the output of the neural network-based base caller is described, in accordance with one implementation.

A data flow logic provides the sequencing images to the neural network-based base caller for base calling. The neural network-based base caller accesses the sequencing images on a patch-by-patch basis (or a tile-by-tile basis). Each of the patches is a sub-grid (or sub-array) of pixelated units in the grid of pixelated units that forms the sequencing images. The patches have dimensions q×r of the sub-grid of pixelated units, where q (width) and r (height) are any numbers ranging from 1 and 10000 (e.g., 3×3, 5×5, 7×7, 10×10, 15×15, 25×25, 64×64, 78×78, 115×115). In some implementations, q and r are the same. In other implementations, q and r are different. In some implementations, the patches extracted from a sequencing image are of the same size. In other implementations, the patches are of different sizes. In some implementations, the patches can have overlapping pixelated units (e.g., on the edges).

Sequencing produces m sequencing images per sequencing cycle for corresponding m image channels. That is, each of the sequencing images has one or more image (or intensity) channels (analogous to the red, green, blue (RGB) channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4. In other implementations, the images can be in blue and violet color channels instead of or in addition to the red and green channels.

Consider, for example, that a sequencing run is implemented using two different image channels: a blue channel and a green channel. Then, at each sequencing cycle, the sequencing run produces a blue image and a green image. This way, for a series of k sequencing cycles of the sequencing run, a sequence of k pairs of blue and green images is produced as output and stored as the sequencing images. Accordingly, a sequence of k pairs of blue and green image patches is generated for the patch-level processing by the neural network-based base caller.

The input image data to the neural network-based base caller for a single iteration of base calling (or a single instance of forward pass or a single forward traversal) comprises data for a sliding window of multiple sequencing cycles. The sliding window can include, for example, a current sequencing cycle, one or more preceding sequencing cycles, and one or more successive sequencing cycles.

In one implementation, the input image data comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle.

In another implementation, the input image data comprises data for five sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a first right flanking/context/next/successive/subsequent (time t+1), and (iv) data for a second right flanking/context/next/successive/subsequent (time t+2) sequencing cycle.

In yet another implementation, the input image data comprises data for seven sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a third left flanking/context/previous/preceding/prior (time t−3) sequencing cycle, (iv) data for a first right flanking/context/next/successive/subsequent (time t+1), (v) data for a second right flanking/context/next/successive/subsequent (time t+2) sequencing cycle, and (vi) data for a third right flanking/ context/next/successive/subsequent (time t+3) sequencing cycle. In other implementations, the input image data comprises data for a single sequencing cycle. In yet other implementations, the input image data comprises data for 10, 15, 20, 30, 58, 75, 92, 130, 168, 175, 209, 225, 230, 275, 318, 325, 330, 525, or 625 sequencing cycles.

The neural network-based base caller processes the image patches through its convolution layers and produces an alternative representation, according to one implementation. The alternative representation is then used by an output layer (e.g., a softmax layer) for generating a base call for either just the current (time t) sequencing cycle or each of the sequencing cycles, i.e., the current (time t) sequencing cycle, the first and second preceding (time t−1, time t−2) sequencing cycles, and the first and second succeeding (time t+1, time t+2) sequencing cycles. The resulting base calls form the sequencing reads.

In one implementation, the neural network-based base caller outputs a base call for a single target cluster for a particular sequencing cycle. In another implementation, the neural network-based base caller outputs a base call for each target cluster in a plurality of target clusters for the particular sequencing cycle. In yet another implementation, the neural network-based base caller outputs a base call for each target cluster in a plurality of target clusters for each sequencing cycle in a plurality of sequencing cycles, thereby producing a base call sequence for each target cluster.

In one implementation, the neural network-based base caller is a multilayer perceptron (MVLP). In another implementation, the neural network-based base caller is a feed-forward neural network. In yet another implementation, the neural network-based base caller is a fully-connected neural network. In a further implementation, the neural network-based base caller is a fully convolution neural network. In yet further implementation, the neural network-based base caller is a semantic segmentation neural network. In yet another further implementation, the neural network-based base caller is a generative adversarial network (GAN).

In one implementation, the neural network-based base caller is a convolution neural network (CNN) with a plurality of convolution layers. In another implementation, the neural network-based base caller is a recurrent neural network (RNN) such as a long short-term memory network (LSTM), bi-directional LSTM (Bi-LSTM), or a gated recurrent unit (GRU). In yet another implementation, the neural network-based base caller includes both a CNN and an RNN.

In yet other implementations, the neural network-based base caller can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The neural network-based base caller can use one or more loss functions such as logistic regression/log loss, multi-class cross-entropy/softmax loss, binary cross-entropy loss, mean-squared error loss, L1 loss, L2 loss, smooth L1 loss, and Huber loss. The neural network-based base caller can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The neural network-based base caller can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The neural network-based base caller is trained using backpropagation-based gradient update techniques. Example gradient descent techniques that can be used for training the neural network-based base caller include stochastic gradient descent, batch gradient descent, and mini-batch gradient descent. Some examples of gradient descent optimization algorithms that can be used to train the neural network-based base caller are Momentum, Nesterov accelerated gradient, Adagrad, Adadelta, RMSprop, Adam, AdaMax, Nadam, and AMSGrad.

In one implementation, the neural network-based base caller uses a specialized architecture to segregate processing of data for different sequencing cycles. The motivation for using the specialized architecture is described first. As discussed above, the neural network-based base caller processes image patches for a current sequencing cycle, one or more preceding sequencing cycles, and one or more successive sequencing cycles. Data for additional sequencing cycles provides sequence-specific context. The neural network-based base caller learns the sequence-specific context during training and base calls them. Furthermore, data for pre and post sequencing cycles provides second order contribution of pre-phasing and phasing signals to the current sequencing cycle.

However, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers (or spatial logic) use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input image data comprises (i) current image patch for a current (time t) sequencing cycle to be base called, (ii) previous image patch for a previous (time t−1) sequencing cycle, and (iii) next image patch for a next (time t+1) sequencing cycle. The specialized architecture then initiates three separate convolution pipelines, namely, a current convolution pipeline, a previous convolution pipeline, and a next convolution pipeline. The current data processing pipeline receives as input the current image patch for the current (time t) sequencing cycle and independently processes it through a plurality of spatial convolution layers to produce a so-called "current spatially convolved representation" as the output of a final spatial convolution layer. The previous convolution pipeline receives as input the previous image patch for the previous (time t−1) sequencing cycle and independently processes it through the plurality of spatial convolution layers to produce a so-called "previous spatially convolved representation" as the output of the final spatial convolution layer. The next convolution pipeline receives as input the next image patch for the next (time t+1) sequencing cycle and independently processes it through the plurality of spatial convolution layers to produce a so-called "next spatially convolved representation" as the output of the final spatial convolution layer.

In some implementations, the current, previous, and next convolution pipelines are executed in parallel. In some implementations, the spatial convolution layers are part of a spatial convolution network (or subnetwork) within the specialized architecture.

The neural network-based base caller further comprises temporal convolution layers (or temporal logic) that mix information between sequencing cycles, i.e., inter-cycles. The temporal convolution layers receive their inputs from the spatial convolution network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolution network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolution network (or subnetwork) within the specialized architecture. The temporal convolution network receives its inputs from the spatial convolution network. In one implementation, a first temporal convolution layer of the temporal convolution network groupwise combines the spatially convolved representations between the sequencing cycles. In another implementation, subsequent temporal convolution layers of the temporal convolution network combine successive outputs of previous temporal convolution layers. The output of the final temporal convolution layer is fed to an output layer that produces an output. The output is used to base call one or more clusters at one or more sequencing cycles.

Additional details about the neural network-based base caller can be found in U.S. Provisional Patent Application No. 62/821,766, titled "ARTIFICIAL INTELLIGENCE-BASED SEQUENCING,", filed on Mar. 21, 2019, which is incorporated herein by reference.

What we claim is:

1. A system, comprising:
- a sequencing instrument;
- at least one processor; and
- a non-transitory computer-readable medium comprising instructions thereon that, when executed by the at least one processor, cause the system to:
  - capture, by one or more light detectors of the sequencing instrument at imaging events of sequencing cycles of a sequencing run, per-cycle sequencing image sets comprising signals from analytes;
  - store a plurality of specialist signal profilers, wherein each specialist signal profiler in the plurality of specialist signal profilers is a different specialist signal profiler separately trained (i) to maximize signal-to-noise ratio of sequenced signals in a particular signal profile (ii) using intensity data segmented according to different spatial configurations of locations of the analytes on a biosensor or different signal distribution configurations of signal profiles encoded in the intensity data; and
- execute a base calling operation by:
  - applying respective specialist signal profilers from among the stored plurality of specialist signal profilers to sequenced signals in respective signal profiles of particular intensity data, from the per-cycle sequencing image sets, segmented according to the different spatial configurations or the different signal distribution configurations; and
  - generating respective base calls for particular analytes using respective noise-corrected intensity data output by the respective specialist signal profilers.

2. The system of claim 1, wherein each specialist signal profiler comprises at least one specialist coefficient set trained to increase the signal-to-noise ratio of a particular segment of intensity data.

3. The system of claim 1, wherein the different spatial configurations include analytes being located on different surfaces of a biosensor on which the base calling operation is executed.

4. The system of claim 3, wherein the different surfaces include a top surface and a bottom surface.

5. The system of claim 4, wherein the different spatial configurations include analytes being located on different lanes of the biosensor.

6. The system of claim 5, wherein the different spatial configurations include analytes being located on different lane groups of the biosensor.

7. The system of claim 6, wherein the different lane groups include top peripheral lanes, central lanes, and bottom peripheral lanes.

8. The system of claim 6, wherein the different lane groups include edge lanes and non-edge lanes.

9. The system of claim 4, wherein the different spatial configurations include analytes being located on different swathes of different lanes of the biosensor.

10. The system of claim 9, wherein the different swathes include top peripheral swathes, central swathes, and bottom peripheral swathes.

11. The system of claim 9, wherein the different swathes include edge swathes and central swathes.

12. The system of claim 9, wherein the different spatial configurations include analytes being located on different tiles of the different swathes of the different lanes of the biosensor.

13. The system of claim 12, wherein the different spatial configurations include analytes being located on different tile groups of the biosensor.

14. The system of claim 13, wherein the different tile groups include edge tiles, central tiles, and near-edge tiles.

15. The system of claim 12, wherein the different spatial configurations include analytes being located on different sub-tiles of the different tiles of the different swathes of the different lanes of the biosensor.

16. The system of claim 3, wherein the different spatial configurations include analytes being located on different sections of the biosensor.

17. The system of claim 16, wherein the different sections include a top-right section, a top-central section, a top-left section, middle-right section, central section, middle-left section, bottom-left section, bottom-central section, and bottom-left section.

18. The system of claim 1, further comprising instructions that, when executed by the at least one processor, cause the system to generate the respective noise-corrected intensity data by applying the respective specialist signal profilers to intensity data from the per-cycle sequencing image sets from a plurality of sequencing cycles.

19. The system of claim 1, wherein the plurality of specialist signal profilers comprise specialist signal profilers separately trained using intensity data segmented according to different combinations of the different spatial configurations.

20. The system of claim 1, wherein the different signal distribution configurations comprise base-wise signal distributions for signals of one or more of the analytes.

21. The system of claim 20, wherein the intensity data segmented according to the different spatial configurations of the locations of the analytes contribute to creation of the respective signal profiles of the particular intensity data during the base calling operation.

22. The system of claim 1, wherein each specialist signal profiler is configured with channel-specific equalizers, wherein each channel-specific equalizer has a plurality of convolution kernels.

23. The system of claim 22, further comprising instructions that, when executed by the at least one processor, cause the system to iteratively train the respective specialist signal profilers during the base calling operation.

24. The system of claim 23, further comprising instructions that, when executed by the at least one processor, cause the system to:

implement, for a current training iteration, expectation maximization that iteratively maximizes a likelihood of channel-wise observing base-wise signal centroids and signal distributions that best fit sequenced signals detected so far during the base calling operation;

channel-wise determine signal-to-noise ratio-maximized sequenced signals in response to applying the respective specialist signal profilers to the sequenced signals;

call bases based on the signal-to-noise ratio-maximized sequenced signals;

channel-wise determine base calling errors based on comparing the signal-to-noise ratio-maximized sequenced signals against signal centroids of the called bases; and channel-wise update coefficients of convolution kernels of the respective specialist signal profilers based on the base calling errors.

25. The system of claim 1, wherein the analytes correspond to wells and wherein the biosensor is a patterned biosensor.

26. The system of claim 1, wherein the plurality of specialist signal profilers are trained using intensity data from at least one sequencing cycle of at least one previous sequencing run.

27. The system of claim 1, further comprising instructions that, when executed by the at least one processor, cause the system to execute the base calling operation by applying the respective specialist signal profilers to particular intensity data from a plurality of sequencing cycles of the sequencing run.

28. The system of claim 1, further comprising instructions that, when executed by the at least one processor, cause the system to modify intensity data from the per-cycle sequencing image sets by applying the respective specialist signal profilers to the sequenced signals.

29. A system, comprising:

a sequencing instrument;

at least one processor; and a non-transitory computer-readable medium comprising instructions thereon that, when executed by the at least one processor, cause the system to:

capture, by one or more light detectors of the sequencing instrument at imaging events of sequencing cycles of a sequencing run, per-cycle sequencing image sets comprising signals from analytes:

fit a plurality of signal distributions on initially sequenced signals detected during initial sequencing cycles of the sequencing run;

separately train respective specialist signal profilers in a plurality of specialist signal profilers (i) to maximize signal-to-noise ratio of respective signal distributions in the plurality of signal distributions (ii) using intensity data of the initially sequenced signals segmented according to the plurality of signal distributions;

store the trained respective specialist signal profilers in memory; and execute a base calling operation by:

uniquely mapping subsequently sequenced signals detected during subsequent sequencing cycles of the sequence run to the respective signal distributions;

applying the trained respective specialist signal profilers stored in memory to the subsequently sequenced signals segmented based on the unique mapping to the respective signal distributions; and generating base calls for the subsequent sequencing cycles using respective noise-corrected intensity data output by the trained respective specialist signal profilers.

30. The system of claim 29, wherein at least some signal distributions in the plurality of signal distributions correspond to different spatial configurations of locations of the analytes on a biosensor or different signal distribution configurations of signal profiles encoded in the intensity data.

31. A system, comprising:

a sequencing instrument;

at least one processor; and a non-transitory computer-readable medium comprising instructions thereon that, when executed by the at least one processor, cause the system to:

capture, by one or more light detectors of the sequencing instrument at imaging events of sequencing cycles of a sequencing run, per-cycle sequencing image sets comprising signals from a population of analytes;

process initially sequenced signals detected during initial sequencing cycles of the sequencing run on an analyte-by-analyte basis, to fit respective signal profiles for respective analytes in the population of analytes;

separately train respective specialist signal profilers in a plurality of specialist signal profilers (i) to maximize signal-to-noise ratio of the respective signal profiles fitted for the respective analytes (ii) using intensity data of the initially sequenced signals segmented according to the respective signal profiles;

store the trained respective specialist signal profilers in memory;

uniquely map subsequently sequenced signals detected during subsequent sequencing cycles of the sequence run to the respective signal profiles on the analyte-by-analyte basis;

apply the trained respective specialist signal profilers stored in memory to the subsequently sequenced signals segmented based on the unique mapping to the respective signal profiles; and generate base calls for the subsequent sequencing cycles on the analyte-by-analyte basis using respective noise-corrected intensity data output by the trained respective specialist signal profilers.

* * * * *